US009234250B2

(12) United States Patent
Eickhoff et al.

(10) Patent No.: US 9,234,250 B2
(45) Date of Patent: *Jan. 12, 2016

(54) CONTROL NUCLEIC ACIDS FOR MULTIPLE PARAMETERS

(71) Applicant: Roche Molecular Systems, Inc., Pleasanton, CA (US)

(72) Inventors: Meike Eickhoff, Rotkreuz (CH); Ellen H. Fiss, Albany, CA (US); Joachim Glaubitz, Sins (CH); Niclas Hitziger, Lucerne (CH); Stephen G. Will, Oakland, CA (US); Dirk Zimmermann, Zug (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/079,155

(22) Filed: Nov. 13, 2013

(65) Prior Publication Data

US 2014/0154669 A1 Jun. 5, 2014

Related U.S. Application Data

(63) Continuation of application No. 13/192,317, filed on Jul. 27, 2011, now Pat. No. 8,609,340.

(60) Provisional application No. 61/368,979, filed on Jul. 29, 2010.

(51) Int. Cl.
*C12Q 1/68* (2006.01)
*C12Q 1/70* (2006.01)

(52) U.S. Cl.
CPC .............. *C12Q 1/703* (2013.01); *C12Q 1/6851* (2013.01); *C12Q 1/706* (2013.01); *C12Q 1/707* (2013.01); *C12Q 1/708* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,562,568 B1 | 5/2003 | Kleiber et al. | |
| 2003/0054372 A1* | 3/2003 | Jaeger | 435/6 |
| 2006/0110724 A1* | 5/2006 | Burkhardt et al. | 435/5 |
| 2009/0148891 A1 | 6/2009 | Bauer et al. | |
| 2009/0280539 A1 | 11/2009 | Bauer et al. | |
| 2010/0041040 A1 | 2/2010 | Babiel et al. | |
| 2011/0003309 A1* | 1/2011 | Detmer et al. | 435/6 |
| 2012/0045751 A1 | 2/2012 | Boyle et al. | |

FOREIGN PATENT DOCUMENTS

| | | |
|---|---|---|
| EP | 10175533 | 11/2010 |
| EP | 10175545 | 11/2010 |
| EP | 10175538 | 1/2011 |
| EP | 14150845.7 | 7/2014 |
| WO | 0137291 A1 | 5/2001 |
| WO | 2009117537 A1 | 9/2009 |
| WO | PCTEP2011062959 | 10/2011 |

OTHER PUBLICATIONS

Gokler (Triggering Reverse Transcriptase Activity of Taq DNA Polymerase, Letters to Roboklon, Jun. 22, 2009).*
Drosten et al. (TaqMan 5'-Nuclease Human Immunodeficiency Virus Type 1 PCR Assay with Phage-Packaged Competitive Internal Control for High-Throughput Blood Donor Screening, Journal of Clinical Microbiology Dec. 2001;39(12):4302-4308).*
Randall et al. (Development and evaluation of internal amplification controls for use in a real-time duplex PCR assay for detection of *Campylobacter coli* and *Campylobacter jejuni*, J Med Microbiol. Feb. 2010;59(Pt 2):172-8. Epub Oct. 15, 2009).*
Dingle et al. (Stable and Noncompetitive RNA Internal Control for Routine Clinical Diagnostic Reverse Transcription—PCR, J Clin Microbiol. Mar. 2004;42(3):1003-11).*
Watzinger et al. (Real-Time Quantitative PCR Assays for Detection and Monitoring of Pathogenic Human Viruses in Immunosuppressed Pediatric Patients, Journal of Clinical Microbiology, Nov. 2004, p. 5189-5198).*
Pasloske et al. (Armored RNA Technology for Production of Ribonuclease- Resistant Viral RNA Controls and Standards, J Clin Microbiol. Dec. 1998;36(12):3590-4).*
Deer et al. (A versatile internal control for use as DNA in real-time PCR and as RNA in real-time reverse transcription PCR assays, Lett Appl Microbiol. Apr. 2010;50(4):366-72. Epub Jan. 22, 2010).*
Hoorfar et al. (Practical Considerations in Design of Internal Amplification Controls for Diagnostic PCR Assays, J Clin Microbiol. May 2004;42(5):1863-8).*
Ivanov et al. (Development of Noncompetitive Exogenous Internal Amplification Control for Real-Time PCR Based on UFA Method, Mol Gen Mikrobiol Virusol. Sep. 1, 2009;(3):8-13).*
Bioneer (Accu Power CycleScript RT premix (dT20), attached, Jan. 13, 2008).*
Baskaran et al., 1996, "Uniform Amplification of a Mixture of Deoxyribonucleic Acids with Varying GC Content", Genome Methods, 6:633-638.
Burns et al., 2008, "Modelling the limit of detection in real-time quantitative PCR," Eur Food Res Technol, 226:1513-1524.
Edwards et al., 1994, "Multiplex PCR: Advantages, Development, and Applications, in PCR Methods and Applications", Cold Spring Harbor Lab Press.
Hoorfar et al., 2004, "Practical Considerations in Design of Internal Amplification Controls for Diagnostic PCR Assays", Journal of Clinical Microbiology, 1863-1868.
Huang et al., 2008, "A Novel Real-Time Multiplex Reverse Transcriptase-Polymerase Chain Reaction for the Detection of HIV-1 RNA by Using Dual-Specific Armored RNA as Internal Control", Intervirology, 51:42-49.

(Continued)

*Primary Examiner* — Stephanie K Mummert
*Assistant Examiner* — Aaron Priest
(74) *Attorney, Agent, or Firm* — Jeffery P. Bernhardt

(57) ABSTRACT

Methods are provided for the amplification of at least a first and a second target nucleic acid that may be present in at least one fluid sample using an internal control nucleic acid for qualitative and/or quantitative purposes.

14 Claims, 19 Drawing Sheets

(56) References Cited

OTHER PUBLICATIONS

Meng et al., 2001, "Automated Multiplex Assay System for Simultaneous Detection of Hepatitis B Virus DNA, Hepatitis C Virus RNA, and Human Immunodeficiency Virus Type 1 RNA," Journal of Clinical Microbiology, 2937-2945.
Pasloske et al., 1998, "Armored RNA Technology for Production of Ribonuclease-Resistant Viral RNA Controls and Standards", Journal of Clinical Microbiology, 3590-3594.
Quan et al., 2008, "Rapid sequence-based diagnosis of viral infection", Antiviral Research, 79:1-5.
Weissensteiner, et al., 2004, "Optimizing PCR with the Aid of Experimental Design, in PCR Technology", Current Innovations, Second Edition, 65-75.
Wittwer et al., 2001, "Real-Time Multiplex PCR Assays", Methods 25, 430-442.
Zimmermann et al., 1996, "Technical Aspects of Quantitative Competitive PCR", Bio Techniques, 21:268-279.
Hoorfar, J., et al., 2004, "Practical Considerations in Design of Internal Amplification Controls for Diagnostic PCR Assays", Journal of Clinical Microbiology, 42(5)1863-1868.
Quan, Phenix-Lan, et al., 2008, "Rapid sequence-based diagnosis of viral infection", Antiviral Research, 79:1-5.
Stoecher, Markus, et al., 2003, "A convenient approach to the generation of multiple internal control DNA for a panel of real-time PCR assays", Journal of Virological Methods, 108:1-8.
Swanson, Priscilla, et al., 2006, "Performance of the automated Abbott RealTime(TM) HIV-1 assay on a genetically diverse panel of specimens from London: Comparison to Versant HIV-1 RNA 3.0, Amplicor HIV-1 Monitor v1.5, and LCx(R) HIV RNA Quantiative assays", Journal of Virological Methods, 137:184-192.
Watzinger, F., et al., 2004, "Real-Time Quantitative PCR Assays for Detection and Monitoring of Pathogenic Human Viruses in Immunosuppressed Pediatric Patients", 42(11):5189-5198.
Erali, Maria, et al., 2000, "Performance Characteristics of the Cobas Amplicor Hepatitis C Virus Monitor Test, Version 2.0", American Journal of Clinical Pathology, 114:180-187.
Huang, Jie, et al., 2008, "A Novel Real-Time Multiplex Reverse Transcriptase-Polymerase Chain Reaction for the Detection of HIV-1 RNA by Using Dual-Specific Armored RNA as Internal Control", Intervirology, 51:41-49.
Konnick, Eric Q., et al., 2002, "Performance Characteristics of the Cobas Amplicor Hepatitis C Virus (HCV) Monitor, Version 2.0, International Unit Assay and the National Genetics Institute HCV Superquant Assay", Journal of Clinical Microbiology, 40(3):768-773.
Meng, Q., et al., 2001, "Automated Multiplex Assay System for Simultaneous Detection of Hepatitis B Virus DNA, Hepatitis C Virus RNA, and Human Immunodeficiency Virus Type 1 RNA", Journal of Clinical Microbiology, 39 (8):2937-2945.
Phan, T.G., et al., 2005, "A novel RT-multiplex PCR for enteroviruses, hepatitis A and E viruses and influenza A virus among infants and children with diarrhea in Vietnam", Archives of Virology, 150:1175-1185.
Qiagen: Product Profile, "artus Herpes Virus LC-PCR Kits".
Roche Molecular Systems, Inc., 2009, "cobas TM TaqScreen MPX Test for use on the cobas s 201 system", 1-60, XP007915685.
Rohayem, Jacques, et al., 2004, "A simple and rapid single-step multiplex RT-PCR to detect Norovirus Astrovirus and Adenovirus in clinical stool samples", Journal of Virological Methods, 118:49-59.
Schoenbrunner, Nancy J., et al., 2006, "Chimeric Thermostable DNA Polymerases with Reverse Transcriptase and Attenuated 3'-5' Exonuclease Activity", Biochemistry, 45:12786-12795.
Singh, Vinay K., et al., 2001, "Simultaneous amplification of DNA and RNA virus using multiplex PCR system", Clinica Chimica Acta, 308:179-181.
Smith, Caitlin, 2010, "Adventures with Multiplex Real-Time PCR", Internet Citation retrieved Oct. 18, 2010, URL:http://www.biocompare.com/Articles/FeaturedArticle/1146/Adventures-with-Multiplex-Real-Time-PCR.html, 1-2.
Stoecher, Markus, et al., 2004, "Internal Control DNA for PCR Assays Introduced into Lambda Phage Particles Exhibits Nuclease Resistance", Clinical Chemistry, 50(11):2163-2166.
Swanson, Priscilla, et al., 2006, "Performance of automated Abbott RealTime TM HIV-1 assay on a genetically diverse panel of specimens from London: Comparison to Versant HIV-1 RNA 3.0, Amplicor HIV-1 Monitor v1.5, and LCx HIV RNA Quantitative assays", Journal of Virological Methods, 137:184-192.
Vandoorn, R., et al., 2009, "Accurate Quantification of Microorganisms in PCR-Inhibiting Environmental DNA Extracts by a Novel Internal Amplification Control Approach Using Biotrove OpenArrays", Applied and Environmental Microbiology, 75(22):7253-7260.
Watzinger, F., et al., 2004, "Real-Time Quantitative PCR Assays for Detection and Monitoring of Pathogenic Human Viruses in Immunosuppressed Pediatric Patients", Journal of Clinical Microbiology, 42(11):5189-5198.
Welzel, Tania M., et al., 2006, "Real-Time PCR Assay for Detection and Quantification of Hepatitis B Virus Genotypes A to G", Journal of Clinical Microbiology, 44(9):3325-3333.
N.A. Lister et al., "Validation of Roche COBAS Amplicor Assay for Detection of *Chlamydia trachomatis* in Rectal and Pharyngeal Specimens by an omp1 PCR Assay", J. Clinical Microbiology, vol. 42, No. 1, Jan. 1, 2004, p. 239-241.
S.J. De Martino et al. "Detection of *Chlamydia trachomatis* DNA using MagNA Pure DNA extraction and Cobas Amplicor CT/NG amplification", Clinical Microbiology and Infection, vol. 12, No. 6, Jun. 1, 2006, p. 576-579.
N. DiDomenico et al., "COBAS Amplicor TM: fully automated RNA and DNA amplification and detection system for routine diagnostic PCR" Clinical Chemistry 42:12, 1915-1923 (1996).

\* cited by examiner

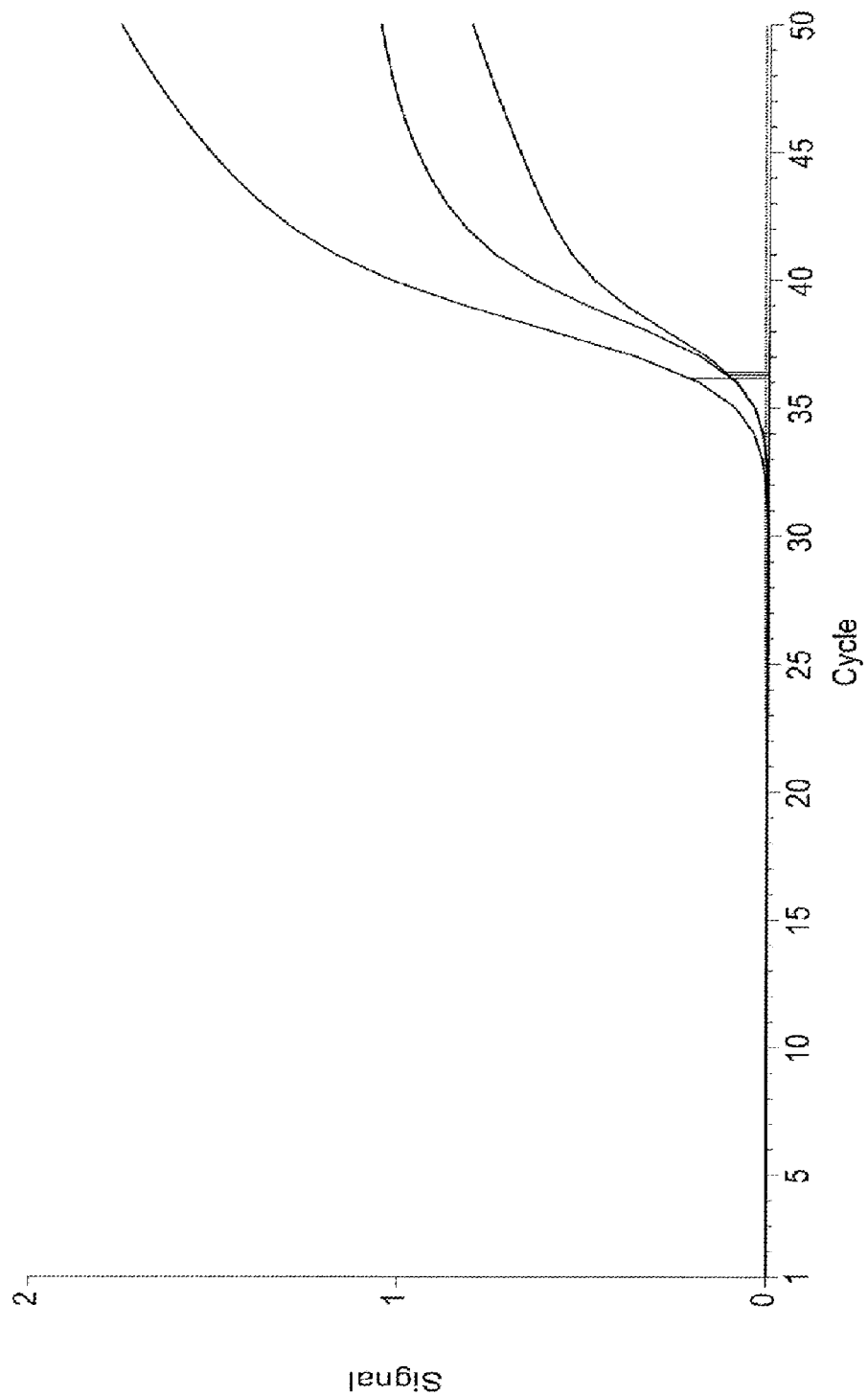

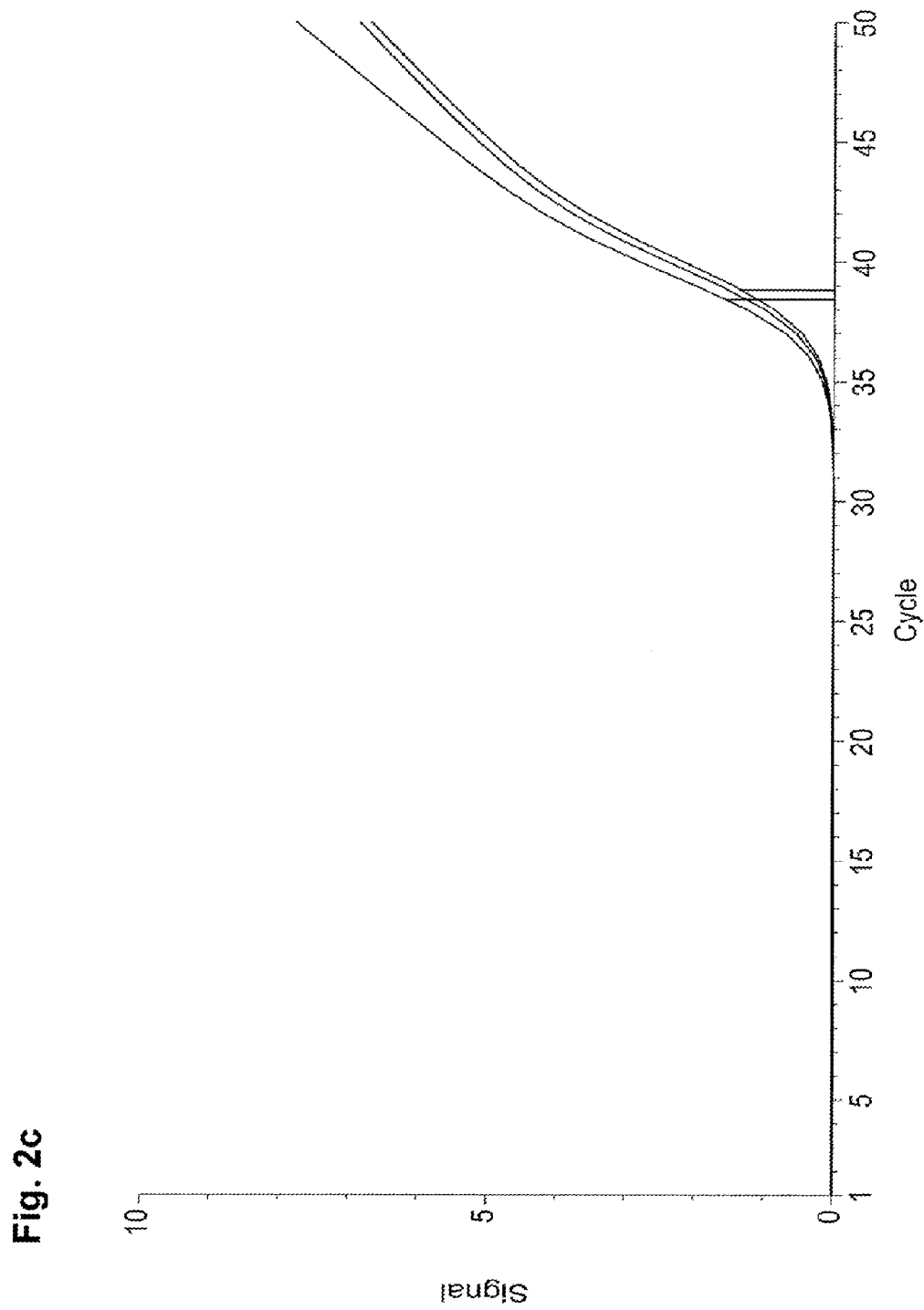

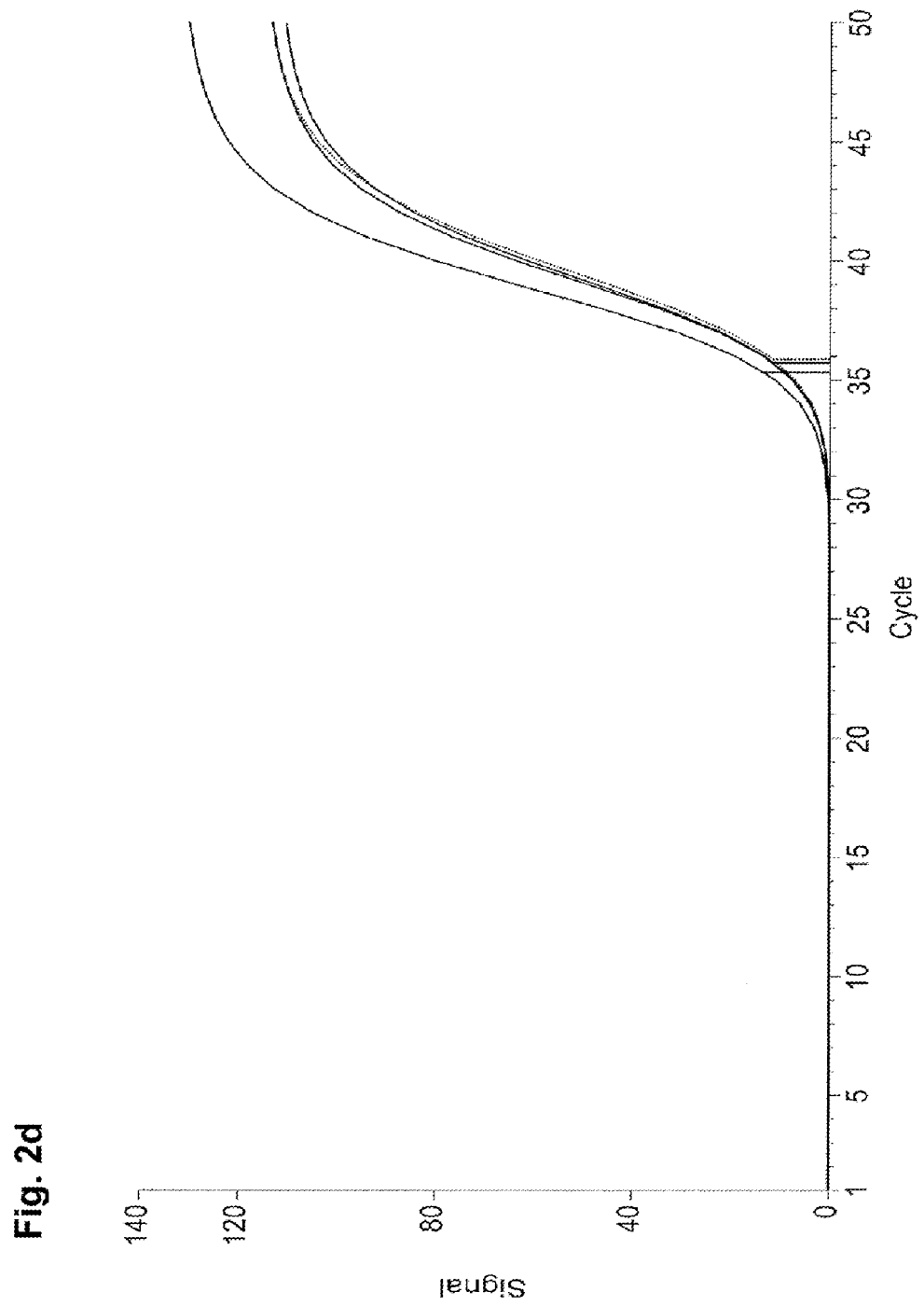

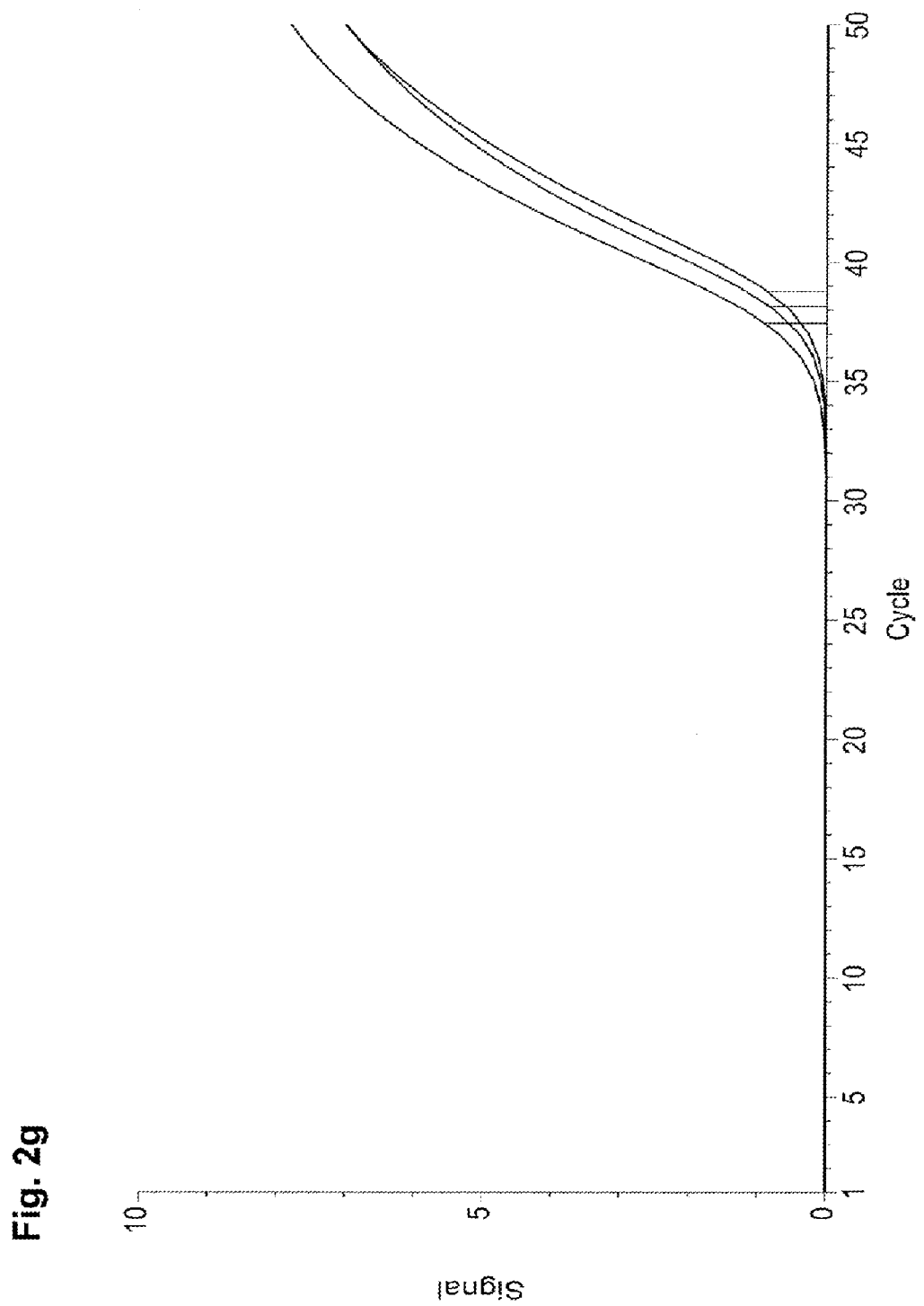

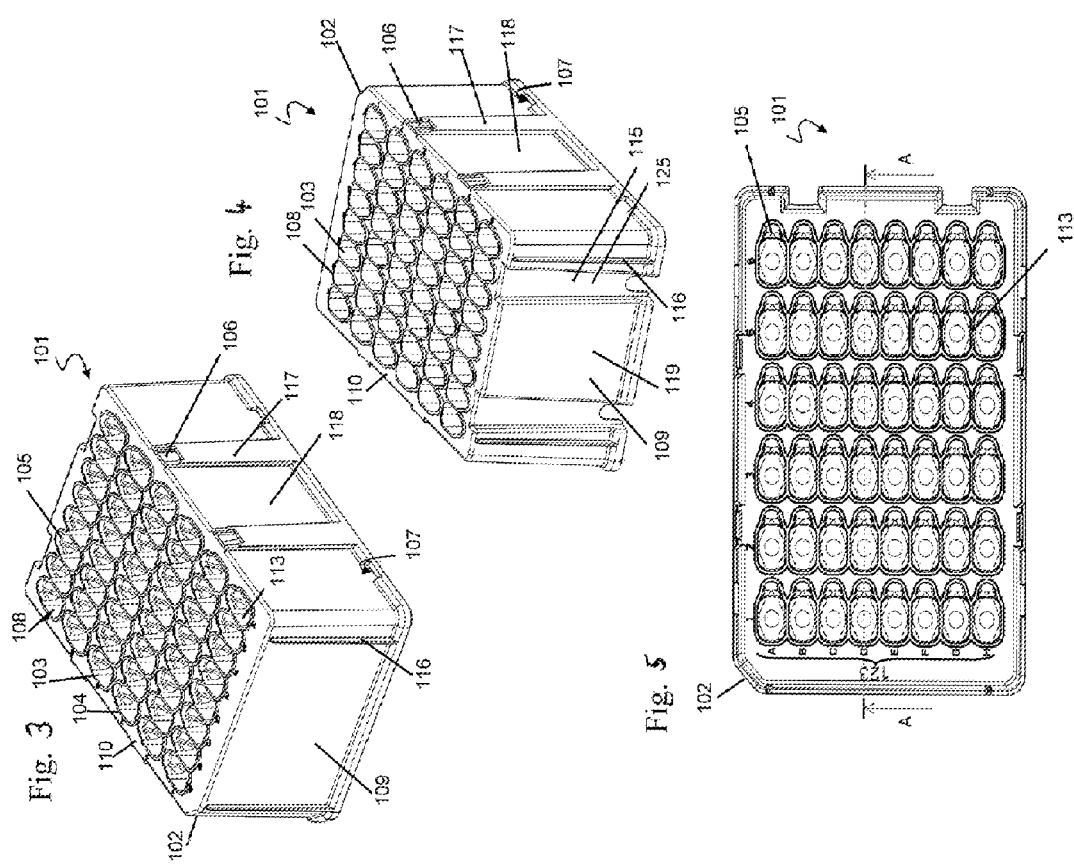

CONTROL NUCLEIC ACIDS FOR MULTIPLE PARAMETERS

CROSS REFERENCE TO RELATED APPLICATIONS

The present application claims the benefit of U.S. Provisional Application No. 61/368,979 filed on Jul. 29, 2010. The entire disclosure of the above-referenced prior application is hereby incorporated herein by reference in its entirety. The present application is a continuation of U.S. Non-provisional application Ser. No. 13/192,317 filed on Jul. 27, 2011 (issued as U.S. Pat. No. 8,609,340 on Dec. 17, 2013), which claims the benefit of U.S. Provisional Application No. 61/368,979 filed on Jul. 29, 2010.

FIELD OF THE INVENTION

The present invention belongs to the field of in-vitro diagnostics. Within this field, it particularly concerns the amplification of at least a first and a second target nucleic acid that may be present in at least one fluid sample using an internal control nucleic acid for qualitative and/or quantitative purposes.

BACKGROUND OF THE INVENTION

In the field of molecular diagnostics, the amplification of nucleic acids from numerous sources has been of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis-B (HBV) and/or C Virus (HCV). Furthermore, said amplification techniques are suitable for bacterial targets such as mycobacteria, or the analysis of oncology markers.

The most prominent and widely-used amplification technique is Polymerase Chain Reaction (PCR). Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification.

Automated systems for PCR-based analysis often make use of real-time detection of product amplification during the PCR process in the same reaction vessel. Key to such methods is the use of modified oligonucleotides carrying reporter groups or labels.

It has been shown that amplification and detection of more than one target nucleic acid in the same vessel is possible. This method is commonly termed "multiplex" amplification and requires different labels for distinction if real-time detection is performed.

It is mostly desirable or even mandatory in the field of clinical nucleic acid diagnostics to control the respective amplification using control nucleic acids with a known sequence, for qualitative (performance control) and/or quantitative (determination of the quantity of a target nucleic using the control as a reference) purposes. Given the diversity especially of diagnostic targets, comprising prokaryotic, eukaryotic as well as viral nucleic acids, and given the diversity between different types of nucleic acids such as RNA and DNA, control nucleic acids are usually designed in a specific manner. In brief, these controls usually resemble the target nucleic acid for which they serve as control in order to mimic their properties during the process. This circumstance applies for both qualitative and quantitative assays. In case multiple parameters are to be detected in a single or in parallel experiments, usually different controls resembling different target nucleic acids are employed, such as e.g. in Swanson et al. (J. Clin. Microbiol., (2004), 42, pp. 1863-1868). Stocher et al. (J. Virol. Meth. (2003), 108, pp. 1-8) discloses a control nucleic acid in which multiple virus-specific competitive controls are comprised on the same DNA molecule.

The present invention provides a controlled amplification method using a different approach that displays various advantages.

SUMMARY OF THE INVENTION

The present invention provides a process for isolating and simultaneously amplifying at least a first and a second target nucleic acid that may be present in one or more samples, the process comprising the steps of:
  a) adding an internal control nucleic acid to each of the one or more samples;
  b) combining a solid support material and the one or more samples in one or more vessels for a period of time, under conditions sufficient to permit nucleic acids comprising the target nucleic acids and the internal control nucleic acid to be immobilized on the solid support material;
  c) isolating the solid support material from the other material present in the samples in a separation station;
  d) purifying the target nucleic acids in the separation station and washing the solid support material one or more times with a wash buffer;
  e) contacting the purified target nucleic acids and the purified internal control nucleic acid with one or more amplification reagents, comprising at least one distinct set of primers for each of the target nucleic acids and for the internal control nucleic acid in at least two reaction vessels, wherein at least a first reaction vessel comprises at least the first target nucleic acid, and at least a second reaction vessel comprises at least the second target nucleic acid, and wherein the second target nucleic acid is absent from the first reaction vessel;
  f) incubating in the reaction vessels the purified target nucleic acids and the purified internal control nucleic acid with the one or more amplification reagents for a period of time, under conditions sufficient for an amplification reaction indicative of the presence or absence of the target nucleic acids to occur; and
  g) detecting and measuring signals generated by the amplification products of the target nucleic acids and being proportional to the concentration of the target nucleic acids, and detecting and measuring a signal generated by the internal control nucleic acid;
wherein the conditions for amplification and detection in steps d) to g) are identical for the at least first and second purified target nucleic acids and the internal control nucleic acid, and wherein the sequence of the internal control nucleic acid is identical for the at least first and second purified target nucleic acids.

The invention further provides wherein the presence of an amplification product of the internal control nucleic acid is indicative of an amplification occurring in the reaction mixture even in the absence of amplification products for one or more of the target nucleic acids, in an embodiment further comprising the following step:
  h) determining the quantity of one or more of the target nucleic acids.

The invention further provides a process wherein the amplification reagents comprise a polymerase with reverse transcriptase activity, the process further comprising between step e) and step f) the step of incubating in the reaction vessels the purified nucleic acids with the one or more amplification reagents for a period of time and under conditions suitable for transcription of RNA by the polymerase with reverse transcriptase activity to occur.

The invention provides an embodiment wherein the internal control nucleic acid is DNA, wherein the internal control nucleic acid is RNA, and further, wherein the internal control nucleic acid is an armored nucleic acid. Further, the invention provides wherein the sequence of the internal control nucleic acid is different from the sequences of the other nucleic acids present in the one or more samples, wherein the sequence of the internal control nucleic acid is derived from a naturally occurring genome, wherein the sequence of the internal control nucleic acid is scrambled, wherein the internal control nucleic acid has a melting temperature from 50° C. to 90° C., and wherein the internal control nucleic acid has a length of up to 500 bases. Further provided is the process wherein the sequence of the internal control nucleic acid has a GC content of 30% to 70%, wherein the internal control nucleic acid has a concentration between LOD and 20×LOD, and wherein the internal control nucleic acid has a concentration between 20×LOD and 5000×LOD. In another embodiment, the more than one internal control nucleic acid is added in step a), but only one of the internal control nucleic acids is amplified in step f).

DESCRIPTION OF THE INVENTION

The present invention provides a method for the controlled amplification of at least a first and a second target nucleic acid that may be present in a fluid sample.

In a first aspect, the invention relates to a process for isolating and simultaneously amplifying at least a first and a second target nucleic acid that may be present in one or more fluid samples, said process comprising the automated steps of:

a. adding an internal control nucleic acid to each of said fluid samples
b. combining together a solid support material and said one or more fluid samples in one or more vessels for a period of time and under conditions sufficient to permit nucleic acids comprising the target nucleic acids and the internal control nucleic acid to be immobilized on the solid support material
c. isolating the solid support material from the other material present in the fluid samples in a separation station
d. purifying the nucleic acids in said separation station and washing the solid support material one or more times with a wash buffer
e. contacting the purified target nucleic acids and the purified internal control nucleic acid with one or more amplification reagents comprising at least one distinct set of primers for each of said target nucleic acids and for said internal control nucleic acid in at least two reaction vessels, wherein at least a first reaction vessel comprises at least said first target nucleic acid and at least a second reaction vessel comprises at least said second target nucleic acid and wherein the second target nucleic acid is absent from the first reaction vessel
f. incubating in said reaction vessel said purified target nucleic acids and said purified internal control nucleic acid with said one or more amplification reagents for a period of time and under conditions sufficient for an amplification reaction indicative of the presence or absence of said target nucleic acids to occur
g. detecting and measuring signals generated by the amplification products of said target nucleic acids and being proportional to the concentration of said target nucleic acids, and detecting and measuring a signal generated by said internal control nucleic acid, wherein the conditions for amplification and detection in steps d. to g. are identical for said at least first and second purified target nucleic acids and said internal control nucleic acid, and wherein the sequence of said internal control nucleic acid is identical for said at least first and second purified target nucleic acids.

The present invention allows for the development of simultaneous assays on a plurality of parameters and/or nucleic acid types while using the same internal control nucleic acid sequence for said different parameters and/or nucleic acid types. Therefore, it contributes to reducing the overall complexity of the corresponding experiments on various levels: For instance, only one internal control nucleic acid sequence has to be designed and added to the respective amplification mixes, thus saving the time and costs for designing and synthesizing or buying multiple control nucleic acid sequences. The assay or assays can be streamlined, and the risk of handling errors is reduced. In addition, the more different control nucleic acid sequences are employed in one assay or parallel assays carried out simultaneously under the same conditions, the more complex it may result to adjust the respective conditions. Moreover, with a single control suitable for a plurality of nucleic acids, said control can be dispensed from a single source e.g. into different vessels containing said different target nucleic acids. Within the scope of the invention, the single control nucleic acid sequence may also serve as a qualitative and as a quantitative control.

As a further advantage of the method described above, the testing of a particular biological sample for other nucleic acids in possible subsequent experiments need not involve another sample preparation procedure with the addition of a different internal control nucleic acid, since the control used in the invention can be used to control the amplification of different nucleic acids. Thus, once an internal control nucleic acid has been added, other parameters may be tested in the same sample under the same conditions.

The internal control nucleic acid can be competitive, non-competitive or partially competitive.

A competitive internal control nucleic acid carries essentially the same primer binding sites as the target and thus competes for the same primers with the target. While this principle allows a good mimicry of the respective target nucleic acid due to their similar structure, it can lower the amplification efficiency with regard to the target nucleic acid or acids and thus lead to a less sensitive assay.

A non-competitive internal control nucleic acid has different primer binding sites than the target and thus binds to different primers. Advantages of such a setup comprise, among others, the fact that the single amplification events of the different nucleic acids in the reaction mixture can take place independently from each other without any competition effects. Thus, no adverse effects occur regarding the limit of detection of the assay as can be the case in a competitive setup.

Finally, in an amplification using a partially competitive setup the respective control nucleic acids and at least one of the target nucleic acids compete for the same primers, while at least one other target nucleic acid binds to different primers.

The fact that the method described above involves a distinct set of primers for each of said target nucleic acids and for said internal control nucleic acid renders the method considerably flexible. In this non-competitive setup it is not necessary to introduce target-specific binding sites into the control nucleic acid as in the case of a competitive setup, and the drawbacks of a competitive setup as mentioned above are avoided. In a non-competitive setup, the internal control nucleic acid has a sequence different from any target sequences, in order not to compete for their primers and/or probes. For example, the sequence of the internal control nucleic acid can be different from the other nucleic acid sequences in the fluid sample. As an example, if the fluid sample is derived from a human, the internal control nucleic acid may not have a sequence which also endogenously occurs within humans. The difference in sequence should thus be at least significant enough to not allow the binding of primers and/or probes to the respective endogenous nucleic acid or acids under stringent conditions and thus render the setup competitive. In order to avoid such interference, the sequence of the internal control nucleic acid used in the invention can be derived from a source different from the origin of the fluid sample. For example, it is derived from a naturally occurring genome, for example a plant genome, or from a grape genome. In an embodiment, a nucleic acid derived from a naturally occurring genome is scrambled. As known in the art, "scrambling" means introducing base mutations in a sequence to a certain extent. For example, the sequence of the internal control nucleic acid used in the invention is substantially altered with respect to the naturally occurring gene it is derived from.

The process comprising the automated steps mentioned above also displays various additional advantages:

It has been a challenge in the prior art that the number of different target nucleic acids in a multiplex assay carried out in a single reaction vessel is limited by the number of appropriate labels. In a real-time PCR assay, for example, the potential overlap of fluorochrome spectra has a great impact on assay performance (risk of false positive results, lower precision etc.) Therefore, the respective fluorophores have to be carefully selected and spectrally well separated in order to assure the desired performance of a diagnostic test. Typically, the number of different usable fluorophores corresponds to a single-digit number of PCR instrument fluorescence channels.

In contrast, in the process described supra, the internally controlled amplification of at least a first and a second target nucleic acid takes place in at least two different reaction vessels, allowing for the simultaneous amplification of a higher number of different target nucleic acids, since signals in different reaction vessels can be detected independently from each other. Still, within the scope of the present invention are embodiments wherein in one or more of the multiple reaction vessels multiplex reactions are performed, thereby multiplying the number of targets that may be amplified simultaneously and under the same conditions. In such embodiments, the internal control nucleic acid serves as a control for the different target nucleic acids within a vessel as well as different target nucleic acids in different vessel.

Thus, one aspect of the invention relates to the process described supra, wherein at least two target nucleic acids are amplified in the same reaction vessel.

For example, it may be preferred to amplify the first, but not the second target nucleic acid in the first reaction vessel and only the second, but not the first target nucleic acid in the second reaction vessel, e.g. depending on the sample and/or the target nucleic acid or acids in question.

Therefore, a further embodiment of the invention is the process described above, wherein the first target nucleic acid is absent from the second reaction vessel.

Especially if a fluid sample is suspected to contain target nucleic acids from different organisms, or even the different organisms as such, or if it is not clear which of the different nucleic acids or organisms may be present in said sample, an advantageous embodiment of the invention is the process described above, wherein the first target nucleic acid and the second target nucleic acid are from different organisms.

A further aspect of the invention is the process described above, wherein the first and/or the second target nucleic acid is a non-viral nucleic acid.

Also, an aspect of the invention is the process described supra, wherein the first and/or the second target nucleic acid is a bacterial nucleic acid.

As described before, the method described above is useful for qualitatively or quantitatively controlling the amplification of at least a first and a second target nucleic acid.

Qualitative detection of a nucleic acid in a biological sample is crucial e.g. for recognizing an infection of an individual. Thereby, one important requirement for an assay for detection of a microbial infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the respective target nucleic acid, the qualitative internal control reaction has to perform reactive within given settings, i.e. the qualitative internal control must be detected, otherwise the test itself is considered to be inoperative. However, in a qualitative setup, said qualitative internal control does not necessarily have to be detected in case of a positive result. For qualitative tests, it is especially important that the sensitivity of the reaction is guaranteed and therefore strictly controlled As a consequence, the concentration of the qualitative internal control must be relatively low so that even in a situation e.g. of slight inhibition the qualitative internal control is not be detected and therefore the test is invalidated.

Thus, an aspect of the invention is the process described above, wherein the presence of an amplification product of said internal control nucleic acid is indicative of an amplification occurring in the reaction mixture even in the absence of amplification products for one or more of said target nucleic acids.

On the other hand and in addition to mere detection of the presence or absence of a nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success. For a quantitative assay, it is necessary to introduce a quantitative standard nucleic acid serving as a reference for determining the absolute quantity of a target nucleic acid. Quantitation can be effectuated either by referencing to an external calibration or by implementing an internal quantitative standard.

In the case of an external calibration, standard curves are created in separate reactions using known amounts of identical or comparable nucleic acids. The absolute quantity of a target nucleic acid is subsequently determined by comparison of the result obtained with the analyzed sample with said standard function. External calibration, however, has the disadvantage that a possible extraction procedure, its varied efficacy, and the possible and often not predictable presence of agents inhibiting the amplification and/or detection reaction are not reflected in the control.

This circumstance applies to any sample-related effects. Therefore, it might be the case that a sample is judged as negative due to an unsuccessful extraction procedure or other sample-based factors, whereas the target nucleic acid to be detected and quantified is actually present in the sample.

For these and other reasons, an internal control nucleic acid added to the test reaction itself is of advantage. When serving as a quantitative standard, said internal control nucleic acid has at least the following two functions in a quantitative test:
i) It monitors the validity of the reaction.
ii) It serves as reference in titer calculation thus compensating for effects of inhibition and controlling the preparation and amplification processes to allow a more accurate quantitation.

Therefore, in contrast to the qualitative internal control nucleic acid in a qualitative test which must be positive only in a target-negative reaction, the quantitative control nucleic acid in a quantitative test has two functions: reaction control and reaction calibration. Therefore it must be positive and valid both in target-negative and target-positive reactions.

It further has to be suited to provide a reliable reference value for the calculation of high nucleic acid concentrations. Thus, the concentration of an internal quantitative control nucleic acid needs to be relatively high.

Therefore, an aspect of the invention is the process described above, further comprising the following step:
h. determining the quantity of one or more of said target nucleic acids.

The internally controlled process described above requires considerably less hands-on time and testing is much simpler to perform than real-time PCR methods used in the prior art. The process offers a major advantage e.g. in the field of clinical virology as it permits parallel amplification of several viruses in parallel experiments. The process is particularly useful in the management of post-transplant patients, in whom frequent viral monitoring is required. Thereby said process facilitates cost-effective diagnosis and contributes to a decrease in the use of antiviral agents and in viral complications and hospitalizations. This equally applies to the field of clinical microbiology. In general, efficiencies will be gained in faster turnaround time and improved testing flexibility. Consequently, this leads to a decrease in the number of tests requested on a patient to make a diagnosis, and potentially shorter hospital stays (e.g. if a diagnosis can be provided sooner, patients requiring antimicrobial therapy will receive it sooner and thus recover earlier). In addition, patients show less morbidity and therefore cause fewer costs related to supportive therapy (e.g., intensive care related to a delay in diagnosis of sepsis). Providing a negative result sooner can have important implications for the overprescription of antibiotics. For example, if a test result obtained by the process according to the invention is able to rule out the pathogen more quickly than with a standard real-time PCR method, then the clinician will not be forced to use empirical antibiotics. Alternatively, if empirical antibiotics are used, the duration of the respective treatment can be shortened.

With respect to designing a specific test based on the process according to the invention, the skilled artisan will particularly, but not only, benefit from the following advantages:
a reduction in software complexity (leading to a reduced risk of programming errors)
focusing of assay development efforts on the chemistry optimization instead of the chemistry plus the instrument control parameters
much more reliable system since a single process is always used and the hardware can be optimally designed to perform this protocol
the skilled artisan performing the internally controlled process described above is provided with the flexibility to run multiple different assays in parallel as part of the same process
cost reduction.

In the sense of the invention, "purification", "isolation" or "extraction" of nucleic acids relate to the following: Before nucleic acids may be analyzed in a diagnostic assay e.g. by amplification, they typically have to be purified, isolated or extracted from biological samples containing complex mixtures of different components. Often, for the first steps, processes are used which allow the enrichment of the nucleic acids. To release the contents of cells or viral particles, they may be treated with enzymes or with chemicals to dissolve, degrade or denature the cellular walls or viral particles. This process is commonly referred to as lysis. The resulting solution containing such lysed material is referred to as lysate. A problem often encountered during lysis is that other enzymes degrading the component of interest, e.g. deoxyribonucleases or ribonucleases degrading nucleic acids, come into contact with the component of interest during the lysis procedure. These degrading enzymes may also be present outside the cells or may have been spatially separated in different cellular compartments prior to lysis. As the lysis takes place, the component of interest becomes exposed to said degrading enzymes. Other components released during this process may e.g. be endotoxins belonging to the family of lipopolysaccharides which are toxic to cells and can cause problems for products intended to be used in human or animal therapy.

There is a variety of means to tackle the above-mentioned problem. It is common to use chaotropic agents such as guanidinium thiocyanate or anionic, cationic, zwitterionic or non-ionic detergents when nucleic acids are intended to be set free. It is also an advantage to use proteases which rapidly degrade the previously described enzymes or unwanted proteins. However, this may produce another problem as said substances or enzymes can interfere with reagents or components in subsequent steps.

Enzymes which can be advantageously used in such lysis or sample preparation processes mentioned above are enzymes which cleave the amide linkages in protein substrates and which are classified as proteases, or (interchangeably) peptidases (see Walsh, 1979, Enzymatic Reaction Mechanisms. W. H. Freeman and Company, San Francisco, Chapter 3). Proteases used in the prior art comprise alkaline proteases (WO 98/04730) or acid proteases (U.S. Pat. No. 5,386,024). A protease which has been widely used for sample preparation in the isolation of nucleic acids in the prior art is proteinase K from *Tritirachium album* (see e.g. Sambrook J. et al., Molecular Cloning: A Laboratory Manual, Cold Spring Harbor Laboratory Press, Cold Spring Harbor, N.Y., 1989) which is active around neutral pH and belongs to a family of proteases known to the person skilled in the art as subtilisins. Especially advantageous for the use in lysis or sample preparation processes mentioned above is the enzyme esperase, a robust protease that retains its activity at both high alkalinity and at high temperatures (EP 1 201 753).

In the sample preparation steps following the lysis step, the component of interest is further enriched. If the non-proteinaceous components of interest are e.g. nucleic acids, they are normally extracted from the complex lysis mixtures before they are used in a probe-based assay.

There are several methods for the purification of nucleic acids:
sequence-dependent or biospecific methods as e.g.:
  affinity chromatography
  hybridization to immobilized probes
sequence-independent or physico-chemical methods as e.g.:
  liquid-liquid extraction with e.g. phenol-chloroform
  precipitation with e.g. pure ethanol
  extraction with filter paper
  extraction with micelle-forming agents as cetyl-trimethyl-ammonium-bromide
  binding to immobilized, intercalating dyes, e.g. acridine derivatives
  adsorption to silica gel or diatomic earths
  adsorption to magnetic glass particles (MGP) or organo-silane particles under chaotropic conditions Particularly interesting for purification purposes is the adsorption of nucleic acids to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface may be preferred because, among other reasons, the nucleic acids do not have to be modified, and even native nucleic acids can be bound. These processes are described in detail by various documents. In Vogelstein B. et al., Proc. Natl. Acad. USA 76 (1979) 615-9, for instance, a procedure for binding nucleic acids from agarose gels in the presence of sodium iodide to ground flint glass is proposed. The purification of plasmid DNA from bacteria on glass dust in the presence of sodium perchlorate is described in Marko M. A. et al., Anal. Biochem. 121 (1982) 382-387. In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi R. et al., Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. The use of magnetic particles to immobilize nucleic acids after precipitation by adding salt and ethanol is more advantageous and described e.g. in Alderton R. P. et al., S., Anal. Biochem. 201 (1992) 166-169 and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic, porous glass is also commercially available that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. Magnetic glass particles and methods using them are described in WO 01/37291. Particularly useful for the nucleic acid isolation in the context of the invention is the method according to R. Boom et al. (J Clin Microbiol. 28 (1990), 495-503).

The term "solid support material" comprises any of the solid materials mentioned above in connection with the immobilization of nucleic acids, e.g. magnetic glass particles, glass fibers, glass fiber filters, filter paper etc., while the solid support material is not limited to these materials.

Thus, an aspect of the invention is the process described above, wherein the solid support material comprises one or more of the materials selected from silica, metal, metal oxides, plastic, polymers and nucleic acids. In an embodiment of the invention, the solid support material is magnetic glass particles.

"Immobilize", in the context of the invention, means to capture objects such as e.g. nucleic acids in a reversible or irreversible manner. Particularly, "immobilized on the solid support material", means that the object or objects are associated with the solid support material for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture probes, wherein nucleic acids are bound to essentially complementary nucleic acids attached to a solid support by base-pairing. In the latter case, such specific immobilization leads to the predominant binding of target nucleic acids.

After the purification or isolation of the nucleic acids including the target nucleic acids from their natural surroundings, analysis may be performed e.g. via the simultaneous amplification described supra.

"Simultaneously", in the sense of the invention, means that two actions, such as amplifying a first and a second or more nucleic acids, are performed at the same time and under the same physical conditions. In one embodiment, simultaneous amplification of the at least first and second target nucleic acids is performed in one vessel. In another embodiment, simultaneous amplification is performed with at least one nucleic acid in one vessel and at least a second nucleic acid in a second vessel, at the same time and under the same physical conditions, particularly with respect to temperature and incubation time wherein the internal control nucleic acid mentioned above is present each of said vessels.

The "first target nucleic acid" and the "second target nucleic acid" are different nucleic acids.

A "fluid sample" is any fluid material that can be subjected to a diagnostic assay targeting nucleic acids and may be derived from a biological source. For example, said fluid sample is derived from a human and is a body liquid. In an embodiment of the invention, the fluid sample is human blood, urine, sputum, sweat, swab, pipettable stool, or spinal fluid.

The term "reaction vessel" comprises, but is not limited to, tubes or the wells of plates such as microwell, deepwell or other types of multiwell plates, in which a reaction for the analysis of the fluid sample such as e.g. reverse transcription or a polymerase chain reaction takes place. The outer limits or walls of such vessels are chemically inert such that they do not interfere with the analytical reaction taking place within. For example, the isolation of the nucleic acids as described above is also carried out in a multiwell plate.

In this context, multiwell plates in analytical systems allow parallel separation and analyzing or storage of multiple samples. Multiwell plates may be optimized for maximal liquid uptake, or for maximal heat transfer. A multiwell plate for use in the context of the present invention can be optimized for incubating or separating an analyte in an automated analyzer. For example, the multiwell plate is constructed and arranged to contact a magnetic device and/or a heating device.

Said multiwell plate, which is interchangeably termed "processing plate" in the context of the invention, comprises:

a top surface comprising multiple vessels with openings at the top arranged in rows. The vessels comprise an upper part, a center part and a bottom part. The upper part is joined to the top surface of the multiwell plate and comprises two longer and two shorter sides. The center part has a substantially rectangular cross-section with two longer sides and two shorter sides;

two opposing shorter and two opposing longer side walls and a base, wherein said base comprises an opening constructed and arranged to place the multiwell plate in contact with said magnetic device and/or a heating device.

In an embodiment of the multiwell plate, adjacent vessels within one row are joined on the longer side of said almost rectangular shape.

For example, the multiwell plate comprises a continuous space which is located between adjacent rows of vessels. Said continuous space is constructed and arranged to accommodate a plate-shaped magnetic device. In an embodiment, the bottom part of the vessels comprises a spherical bottom. In an embodiment, the bottom part of said vessels comprises a conical part located between said central part and said spherical bottom.

In an embodiment, the top surface comprises ribs, wherein said ribs surround the openings of the vessels. For example, one shorter side of said upper part of the vessels comprises a recess, said recess comprising a bent surface extending from the rib to the inside of the vessel.

Furthermore, in an embodiment, the vessels comprise a rounded inside shape.

For fixation to the processing or incubation stations, the base may comprises a rim comprising recesses. Latch clips on a station of an analyzer can engage with said recesses to fix the plate on a station.

In an embodiment, the vessels comprise an essentially constant wall thickness.

For example, the processing plate (101) in the context of the present invention is a 1-component plate. Its top surface (110) comprises multiple vessels (103) (FIG. 5, FIG. 6). Each vessel has an opening (108) at the top and is closed at the bottom end (112). The top surface (110) comprises ribs (104) which are may be elevated relative to the top surface (110) and surround the openings (108) of the vessels (103). This prevents contamination of the contents of the vessels (103) with droplets of liquid that may fall onto the top surface (110) of the plate (101). Views of an exemplary process plate are shown in FIGS. 3 to 8.

The footprint of the processing plate (101) may comprise a length and width of the base corresponding to ANSI SBS footprint format. For example, the length is 127.76 mm+/− 0.25 mm, and the width is 85.48 mm+/−0.25 mm. Thus, the plate (101) has two opposing shorter side walls (109) and two opposing longer side walls (118). The processing plate (101) comprises form locking elements (106) for interacting with a handler (500, FIG. 12). The processing plate (101) can be gripped, transported and positioned quickly and safely at high speed while maintaining the correct orientation and position. For example, the form locking elements (106) for gripping are located within the upper central part, for example the upper central third of the processing plate (101). This has the advantage that a potential distortion of the processing plate (101) has only a minor effect on the fault locking elements (106) and that the handling of the plate (101) is more robust.

The processing plate (101) may comprise hardware-identifiers (102) and (115). The hardware identifiers (102) and (115) are unique for the processing plate (101) and different from hardware identifiers of other consumables used in the same system. The hardware identifiers (102, 115) may comprise ridges (119) and/or recesses (125) on the side walls of the consumables, wherein said pattern of ridges (119) and/or recesses (125) is unique for a specific type of consumable, for example the processing plate (101). This unique pattern is also referred to herein as a unique "surface geometry". The hardware-identifiers (102, 115) ensure that the user can only load the processing plate (101) into the appropriate stacker position of an analytical instrument in the proper orientation. On the sides of processing plate (101), guiding elements (116) and (117) are comprised (FIG. 3, FIG. 4). They prevent canting of the processing plate (101). The guiding elements (116, 117) allow the user to load the processing plates (101) with guiding elements (116, 117) as a stack into an analytical instrument which is then transferred vertically within the instrument in a stacker without canting of the plates.

The center part (120) of the vessels (103) has an almost rectangular cross section (FIG. 6, FIG. 7). They are separated along the longer side (118) of the almost rectangular shape by a common wall (113) (FIG. 3). The row of vessels (103) formed thereby has the advantage that despite the limited space available, they have a large volume, for example 4 ml. Another advantage is that because of the essentially constant wall thickness, the production is very economical. A further advantage is that the vessels (103) strengthen each other and, thus, a high stability of the shape can be obtained.

Between the rows of vessels (103), a continuous space (121) is located (FIG. 6, FIG. 7). The space (121) can accommodate magnets (202, 203) or heating devices (128) (FIG. 11). These magnets (202, 203) and heating devices (128) are for example solid devices. Thus, magnetic particles (216) comprised in liquids (215) which can be held in the vessels (103) can be separated from the liquid (215) by exerting a magnetic field on the vessels (103) when the magnets (202, 203) are brought into proximity of the vessels (103). Or the contents of the vessels (103) can be incubated at an elevated, controlled temperature when the processing plate (101) is placed on the heating device (128). Since the magnets (202, 203) or heating devices (128) can be solid, a high energy density can be achieved. The almost rectangular shape of the central part (120) of the vessels (103) (FIG. 10) also optimizes the contact between the vessel wall (109) and a flat shaped magnet (202) or heating device (128) by optimizing the contact surface between vessel (103) and magnet (202) or heating device (128) and thus enhancing energy transfer into the vessel (103).

In the area of the conical bottom (111) of the vessels, the space (121) is even more pronounced and can accommodate further magnets (203). The combination of the large magnets (202) in the upper area and the smaller magnets (203) in the conical area of the vessels allows separation of magnetic particles (216) in larger or small volumes of liquid (215). The small magnets (203), thus, make it easier to sequester the magnetic particles (216) during eluate pipetting. This makes it possible to pipette the eluate with minimal loss by reducing the dead volume of the magnetic particle (216) pellet. Furthermore, the presence of magnetic particles (216) in the transferred eluate is minimized.

At the upper end of the vessels (103), one of the shorter side walls (109) of the vessel (103) comprises an reagent inlet channel (105) which extends to the circumferential rib (104) (FIGS. 3, 4, 7). The reagents are pipetted onto the reagent inlet channel (105) and drain off the channel (105) into the vessel (103). Thus, contact between the pipet needle or tip (3, 4) and liquid contained in the vessel is prevented. Furthermore, splashes resulting from liquid being directly dispensed into another liquid (215) contained in the vessels (103), which may cause contamination of the pipet needle or tip (3, 4) or neighboring vessels (103) is prevented. Sequential pipetting onto the reagent inlet channel (105) of small volumes of reagents followed by the largest volume of another reagent ensures that the reagents which are only added in small amounts are drained completely into the vessel (103). Thus, pipetting of small volumes of reagents is possible without loss of accuracy of the test to be performed.

On the inside, on the bottom of the vessels (111, 112), the shape becomes conical (111) and ends with a spherical bottom (112) (FIG. 6. FIG. 7). The inside shape of the vessel (114), including the rectangular center part (120), is rounded. The combination of spherical bottom (112), rounded inside shape (114), conical part (111) and refined surface of the vessels (103) leads to favorable fluidics which facilitate an effective separation and purification of analytes in the processing plate (101).

The spherical bottom (112) allows an essentially complete use of the separated eluate and a reduction of dead-volume which reduces the carryover of reagents or sample cross-contamination.

The rim on the base (129) of the processing plate (101) comprises recesses (107) for engagement with latch clips (124) on the processing station (201) or heating device (128) or analytical instrument (126) (FIG. 5, FIG. 9). The engagement of the latch clips (124) with the recesses (107) allows positioning and fixation of the processing plate (101) on the processing station (201). The presence of the recesses (107) allows the latch force to act on the processing plate (101) almost vertically to the base (129). Thus, only small forces acting sideways can occur. This reduces the occurrence of strain, and, thus, the deformation of the processing plate (101). The vertical latch forces can also neutralize any deformations of the processing plate (101) leading to a more precise positioning of the spherical bottoms (111) within the processing station (201). In general, the precise interface between the processing plate (101) and the processing station (201) or heating device (128) within an analyzer reduces dead-volumes and also reduces the risk of sample cross-contamination.

A "separation station" is a device or a component of an analytical system allowing for the isolation of the solid support material from the other material present in the fluid sample. Such a separation station can e.g. comprise, but is not limited to, a centrifuge, a rack with filter tubes, a magnet, or other suitable components. In an embodiment of the invention, the separation station comprises one or more magnets. For example, one or more magnets are used for the separation of magnetic particles, for example magnetic glass particles, as a solid support. If, for example, the fluid sample and the solid support material are combined together in the wells of a multiwell plate, then one or more magnets comprised by the separation station can e.g. be contacted with the fluid sample itself by introducing the magnets into the wells, or said one or more magnets can be brought close to the outer walls of the wells in order to attract the magnetic particles and subsequently separate them from the surrounding liquid.

In an embodiment, the separation station is a device that comprises a multiwell plate comprising vessels with an opening at the top surface of the multiwell plate and a closed bottom. The vessels comprise an upper part, a center part and a bottom part, wherein the upper part is joined to the top surface of the multiwell plate and may comprise two longer and two shorter sides. The center part has a substantially rectangular cross-section with two longer sides, wherein said vessels are aligned in rows. A continuous space is located between two adjacent rows for selectively contacting at least one magnet mounted on a fixture with the side walls in at least two Z-positions. The device further comprises a magnetic separation station comprising at least one fixture. The fixture comprises at least one magnet generating a magnetic field. A moving mechanism is present which vertically moves said at least one fixture comprising at least one magnet at least between first and second positions with respect to the vessels of the multiwell plate. For example, said at least two Z-positions of the vessels comprise the side walls and the bottom part of said vessels. The magnetic field of said at least one magnet may draw the magnetic particles to an inner surface of the vessel adjacent to said at least one magnet when said at least one magnet is in said first position. The effect of said magnetic field is less when said at least one magnet is in said second position than when said at least one magnet is in said first position. For example, the fixture comprising said at least one magnet comprises a frame. The vessels have features as described above in the context of multiwell plate/processing plate. One such feature is that at least a part of said vessels has a substantially rectangular cross-section orthogonal to the axis of said vessels.

In said first position, said at least one magnet is adjacent to said part of said vessels. Adjacent is understood to mean either in close proximity such as to exert a magnetic field on the contents of the vessel, or in physical contact with the vessel.

The separation station comprises a frame to receive the multiwell plate, and latch-clips to attach the multiwell plate. For example, the separation station comprises two types of magnets. This embodiment is further described below.

A second embodiment is described below, which comprises a spring which exerts a pressure on the frame comprising the magnets such that the magnets are pressed against the vessels of the multiwell plate.

The first magnets may be constructed and arranged to interact with vessels of a multiwell plate for exerting a magnetic field on a large volume of liquid comprising magnetic particles held in said vessels. Said second magnets may be constructed and arranged to interact with vessels of a multiwell plate for exerting a magnetic field on a small volume of liquid comprising magnetic particles held in said vessels. Said first and second magnets can be moved to different Z-positions.

Useful in the context of the present invention and said separation station is further a method of isolating and purifying a nucleic acid. The method comprises the steps of binding a nucleic acid to magnetic particles in a vessel of a multiwell plate. The vessel comprises an upper opening, a central part and a bottom part. The bound material is then separated from unbound material contained in a liquid when the major part of the liquid is located above the section where the conical part of the vessel is replaced by the central part with the rectangular shape, by moving a magnet from a second position to a first position and, in said first position, applying a magnetic field to the central part and, optionally, additionally applying a magnetic field to the bottom part of said vessel. The magnetic particles can optionally be washed with a washing solution. A small volume of liquid, wherein the major part of the liquid is located below the section where the conical part of the vessel is replaced by the central part with the rectangular shape is separated from said magnetic particles by selectively applying a magnetic field to the bottom part of said vessel.

Useful in the context of the present invention is also a magnetic separation station for separating a nucleic acid bound to magnetic particles, said separation station comprising first magnets which are constructed and arranged to interact with vessels of a multiwell plate for exerting a magnetic field on a large volume of liquid comprising magnetic particles held in said vessels, and second magnets constructed and arranged to interact with vessels of a multiwell plate for exerting a magnetic field on a small volume of liquid comprising magnetic particles held in said vessels, and wherein said first and second magnets can be moved to different Z-positions. Embodiments of the magnetic separation station are described herein.

A first embodiment of a separation station (201) useful for the present invention is described below. The first embodiment of said separation station (201) comprises at least two types of magnets (202, 203). The first, long type of magnet (202) is constructed and arranged to fit into the space (121) of the processing plate (101). Magnet (202), thus, exerts a magnetic field on the liquid (215) in the vessel (103) to sequester magnetic particles (216) on the inside of the vessel wall. This allows separation of the magnetic particles (216) and any material bound thereto and the liquid (215) inside the vessel (103) when a large volume of liquid (215) is present. Magnet (202) has an elongated structure and is constructed and arranged to interact with the essentially rectangular central part (120) of the vessel. Thus, magnet (202) is used when the major part of the liquid (215) is located above the section where the conical part (111) of the vessel (103) is replaced by the central part (120) with the rectangular shape. As shown in FIG. 10, the construction of the magnets (202) comprises fixtures (204, 204a) comprising magnets (202) which fit into the space (121) between the rows of vessels (103) in the processing plate (101). Another embodiment of magnets (202) comprises magnets (202) arranged on fixtures (204, 204a). The magnets (203) of the separation station (201) are smaller, and can interact with the conical part (111) of the vessel (103). This is shown in FIG. 10. Magnets (203) are arranged on a base (205) which can be moved into the space (121) of the processing plate (101). Each magnet (202, 203) is constructed to interact with two vessels (103) in two adjacent rows. In an embodiment, the processing plate (101) has 6 rows of 8 vessels (103). A separation station (201) which can interact with the processing plate (101) has three fixtures (204, 204a) comprising magnets (202) and four bases (205) comprising magnets (203). An embodiment is also included wherein the separation station has four magnetic fixtures (204, 204a) comprising magnets (202) and three magnetic bases (205) comprising magnets (203).

The magnets (202, 203) are movable. The separation station (201) comprises a mechanism to move the fixtures (204, 204a) and the bases (205). All fixtures (204, 204a) are interconnected by a base (217) and are, thus, moved coordinately. All magnets (203) are joined to one base (218) and are, thus, moved coordinately. The mechanism for moving the magnetic plates (202) and (203) is constructed and arranged to move the two types of magnetic plates (202, 203) to a total of four end positions:

In FIG. 10 a-c, the magnets (203) are located in proximity of the conical part of the vessels (103) of the processing plate (101). This is the uppermost position of magnets (203), and is the separation position. In this Figure, the magnets (202) are located in the lowermost position. They are not involved in separation when they are in this position.

In an embodiment shown in FIG. 10, the base (217) of magnets (202) is connected to a positioning wheel (206). The base (217) comprises a bottom end (207) which is flexibly in contact with a connecting element (208) by a moving element (209). Said moving element is constructed and arranged to move the connecting element (208) along a rail (212) from one side to the other. Said moving element (209) is fixed to the connecting element (208) with a pin (220). Said connecting element (208) is fixed to the positioning wheel (206) by screw (210). Connecting element (208) is also connected to axis (211). Said connecting element (208) is a rectangular plate. As the positioning wheel (206) moves eccentrically, around an axis (211), such that the screw (210) moves from a point above the eccentric axis to a point below the eccentric axis, moving element (209) and the bottom end (207) of the base (204) with the magnets (202) attached thereto are moved from the uppermost position to the lowermost position. The base (218) is mounted on a bottom part (219) and is connected, at its lower end, with pin (213) to a moving element (214), which can be a wheel, which interacts with the positioning wheel (206). When the positioning wheel (206) rotates around the axis (211), wheel (214) moves along positioning wheel (206). If the wheel (214) is located on a section of positioning wheel (206) where the distance from the axis (211) is short, the magnets (203) are in their lowermost position. When wheel (214) is located on a section of positioning wheel (206) where the distance from the axis (211) is at a maximum, the magnets (203) are in their uppermost position. Thus, in an embodiment of the first embodiment of the separation station, the location of the magnets (203) is controlled by the shape of the positioning wheel (206). When moving element (209) moves along the central, rounded upper or lower part (212a) of rail (212), the small type of magnets (203) are moved up and down. When the moving element (209) is located on the side (212b) of bottom end (207) and moves up or down, the magnets (202) are moved up- or downwards. The positioning wheel can be rotated by any motor (224).

In an embodiment, a spring (225) is attached to the base (222) of the separation station and the base (218) of magnets (203) to ensure that magnets (203) are moved into the lowermost position when they are moved downwards.

The term "pin" as used herein relates to any fixation element, including screws or pins.

In a second embodiment, the separation station (230) comprises at least one fixture (231) comprising at least one magnet (232), a number of magnets equal to a number of vessels (103) in a row (123). The separation station (230) comprises a number of fixtures (231) equal to the number of rows (123) of the multiwell plate (101) hereinbefore described. For example, six fixtures (231) are mounted on the separation station (230). At least one magnet (232) is mounted on one fixture (231). For example, the number of magnets (232) equals the number of vessels (103) in one row (123). For example, eight magnets (232) are mounted on one fixture (231). For example, one type of magnet (232) is comprised on said fixture (231). For example, the magnet (232) is mounted on one side oriented towards the vessels with which the magnet interacts.

The fixture (231) is mounted on a base (233). For example, said mount is flexible. The base (233) comprises springs (234) mounted thereon. The number of springs (234) is at least one spring per fixture (231) mounted on said base (233). The base further comprises a chamfer (236) which limits the movement of the spring and, consequently, the fixture (231) comprising the magnets (232). For example, any one of said springs (234) is constructed and arranged to interact with a fixture (231). For examples, said spring (234) is a yoke spring. Said interaction controls the horizontal movement of the fixtures (231). Furthermore, the separation station (230) comprises a frame (235). The base (233) with fixtures (231) is connected to the frame (235) by a moving mechanism as described hereinbefore for the magnets (232) of the first embodiment.

For example, said base (233) and fixture (231) is constructed and arranged to move vertically (in Z-direction).

The multiwell plate (101) hereinbefore described is inserted into the separation station (230). The fixture (231) comprising the magnets (232) is moved vertically. Any one fixture (232) is, thus, moved into a space (121) between two rows (123) of vessels (103). The vertical movement brings the magnets (232) mounted on a fixture (231) into contact with the vessels (103). The Z-position is chosen depending on the volume of liquid (215) inside the vessels (103). For large volumes, the magnets (232) contact the vessels (103) in a center position (120) where the vessels (103) are of an almost rectangular shape. For small volumes of liquid (215) where the major part of the liquid (215) is located below the center part (120) of the vessels (103), the magnets (232) contact the conical part (111) of the vessels (103).

A spring is attached to the base (233) of any one frame (231) (FIG. 9 a), b)). The spring presses the magnets (232) against the vessels (103). This ensures a contact between magnets (232) and vessels (103) during magnetic separation. For example, the magnet (232) contacts the vessel (103) on the side wall (109) located underneath the inlet (105). This has the advantage that liquid which is added by pipetting flows over the sequestered magnetic particles and ensures that particles are resuspended and that all samples in all vessels are treated identically.

This embodiment is particularly suited to separate a liquid (215) comprised in a multiwell plate (101) as hereinbefore described, from magnetic particles (216) when different levels of liquid (215) are contained in the vessels (103) of said multiwell plate (101).

A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components. The wash buffer may, for example, contain ethanol and/or chaotropic agents in a buffered solution or solutions with an acidic pH without ethanol and/or chaotropic agents as described above. Often the washing solution or other solutions are provided as stock solutions which have to be diluted before use.

The washing in the process according to the invention requires a more or less intensive contact of the solid support material and the nucleic acids immobilized thereon with the wash buffer. Different methods are possible to achieve this, e.g. shaking the wash buffer with the solid support material in or along with the respective vessel or vessels. Another advantageous method is aspirating and dispensing the suspension comprising wash buffer and solid support material one or more times. This method may be carried out using a pipet, wherein said pipet comprises a disposable pipet tip into which said suspension is aspirated and from which it is dispensed again. Such a pipet tip can be used several times before being discarded and replaced. Disposable pipet tips useful for the invention may have a volume of at least 10 µl, or at least 15 µl, or at least 100 µl, or at least 500 µl, or at least 1 ml, or about 1 ml. Pipets used in the context of the invention can also be pipetting needles.

Thus, an aspect of the invention is the process described above, wherein said washing in step d. comprises aspirating and dispensing the wash buffer comprising the solid support material.

For downstream processing of the isolated nucleic acids, it can be advantageous to separate them from the solid support material before subjecting them to amplification.

Therefore, an aspect of the invention is the process described above, wherein said process further comprises in step d. the step of eluting the purified nucleic acids from the solid support material with an elution buffer after washing said solid support material.

An "elution buffer" in the context of the invention is a suitable liquid for separating the nucleic acids from the solid support. Such a liquid may e.g. be distilled water or aqueous salt solutions, such as e.g. Tris buffers like Tris HCl, or HEPES, or other suitable buffers known to the skilled artisan. The pH value of such an elution buffer can be alkaline or neutral. Said elution buffer may contain further components such as e.g. chelators like EDTA, which stabilizes the isolated nucleic acids by inactivation of degrading enzymes.

The elution can be carried out at elevated temperatures, such that an embodiment of the invention is the process described above, wherein step d. is carried out at a temperature between 70° C. and 90° C., or at a temperature of 80° C.

"Amplification reagents", in the context of the invention, are chemical or biochemical components that enable the amplification of nucleic acids. Such reagents comprise, but are not limited to, nucleic acid polymerases, buffers, mononucleotides such as nucleoside triphosphates, oligonucleotides e.g. as oligonucleotide primers, salts and their respective solutions, detection probes, dyes, and more.

As is known in the art, a "nucleoside" is a base-sugar combination. The base portion of the nucleoside is normally a heterocyclic base. The two most common classes of such heterocyclic bases are purines and pyrimidines.

"Nucleotides" are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. A nucleotide is the monomeric unit of an "oligonucleotide", which can be more generally denoted as an "oligomeric compound", or a "polynucleotide", more generally denoted as a "polymeric compound". Another general expression for the aforementioned is deoxyribonucleic acid (DNA) and ribonucleic acid (RNA).

According to the invention, an "oligomeric compound" is a compound consisting of "monomeric units" which may be nucleotides alone or non-natural compounds (see below), more specifically modified nucleotides (or nucleotide analogs) or non-nucleotide compounds, alone or combinations thereof.

"Oligonucleotides" and "modified oligonucleotides" (or "oligonucleotide analogs") are subgroups of oligomeric compounds. In the context of this invention, the term "oligonucleotide" refers to components formed from a plurality of nucleotides as their monomeric units. The phosphate groups are commonly referred to as forming the internucleoside backbone of the oligonucleotide. The normal linkage or backbone of RNA and DNA is a 3' to 5' phosphodiester linkage. Oligonucleotides and modified oligonucleotides (see below) useful for the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang S. A. et al., Methods in Enzymology 68 (1979) 90-98, the phosphodiester method disclosed by Brown E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Scr. 25 (1985) 280-282 and the solid support method disclosed in U.S. Pat. No. 4,458,066.

In the process described above, the oligonucleotides may be chemically modified, i.e. the primer and/or the probe comprise a modified nucleotide or a non-nucleotide compound. The probe or the primer is then a modified oligonucleotide.

"Modified nucleotides" (or "nucleotide analogs") differ from a natural nucleotide by some modification but still consist of a base, a pentofuranosyl sugar, a phosphate portion, base-like, pentofuranosyl sugar-like and phosphate-like portion or combinations thereof. For example, a label may be attached to the base portion of a nucleotide whereby a modified nucleotide is obtained. A natural base in a nucleotide may also be replaced by e.g. a 7-deazapurine whereby a modified nucleotide is obtained as well.

A "modified oligonucleotide" (or "oligonucleotide analog"), belonging to another specific subgroup of oligomeric compounds, possesses one or more nucleotides and one or more modified nucleotides as monomeric units. Thus, the term "modified oligonucleotide" (or "oligonucleotide analog") refers to structures that function in a manner substantially similar to oligonucleotides and can be used interchangeably in the context of the present invention. From a synthetical point of view, a modified oligonucleotide (or an oligonucleotide analog) can for example be made by chemical modification of oligonucleotides by appropriate modification of the phosphate backbone, ribose unit or the nucleotide bases (Uhlmann and Peyman, Chemical Reviews 90 (1990) 543; Velma S., and Eckstein F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester internucleoside linkages; deaza- or azapurines and -pyrimidines in place of natural purine and pyrimidine bases, pyrimidine bases having substituent groups at the 5 or 6 position; purine bases having altered substituent groups at the 2, 6 or 8 positions or 7 position as 7-deazapurines; bases carrying alkyl-, alkenyl-, alkinyl or aryl-moieties, e.g. lower alkyl groups such as methyl, ethyl, propyl, butyl, tert-butyl, pentyl, hexyl, heptyl, octyl, nonyl, decyl, or aryl groups like phenyl, benzyl, naphtyl; sugars having substituent groups at, for example, their 2' position; or carbocyclic or acyclic sugar analogs. Other modifications consistent with the spirit of this invention are known to those skilled in the art. Such modified oligonucleotides (or oligonucleotide analogs) are best described as being functionally interchangeable with, yet structurally different from, natural oligonucleotides. In more detail, exemplary modifications are disclosed in Velina S., and Eckstein F., Annu. Rev. Biochem. 67 (1998) 99-134 or WO 02/12263. In addition, modification can be made wherein nucleoside units are joined via groups that substitute for the internucleoside phosphate or sugar phosphate linkages. Such linkages include those disclosed in Velma S., and Eckstein F., Annu. Rev. Biochem. 67 (1998) 99-134. When other than phosphate linkages are utilized to link the nucleoside units, such structures have also been described as "oligonucleosides".

A "nucleic acid" as well as the "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined.

The term "primer" is used herein as known to the expert skilled in the art and refers to oligomeric compounds, primarily to oligonucleotides, but also to modified oligonucleotides that are able to prime DNA synthesis by a template-dependent DNA polymerase, i.e. the 3'-end of the e.g. primer provides a free 3'-OH group whereto further nucleotides may be attached by a template-dependent DNA polymerase establishing 3'- to 5'-phosphodiester linkage whereby deoxynucleoside triphosphates are used and whereby pyrophosphate is released.

A "probe" also denotes a natural or modified oligonucleotide. As known in the art, a probe serves the purpose to detect an analyte or amplificate. In the case of the process described above, probes can be used to detect the amplificates of the target nucleic acids. For this purpose, probes typically carry labels.

"Labels", often referred to as "reporter groups", are generally groups that make a nucleic acid, in particular oligonucleotides or modified oligonucleotides, as well as any nucleic acids bound thereto distinguishable from the remainder of the sample (nucleic acids having attached a label can also be termed labeled nucleic acid binding compounds, labeled probes or just probes). Exemplary labels according to the invention are fluorescent labels, which are e.g. fluorescent dyes such as a fluorescein dye, a rhodamine dye, a cyanine dye, and a coumarin dye. Exemplary fluorescent dyes according to the invention are FAM, HEX, JA270, CAL635, Coumarin343, Quasar705, Cyan500, CY5.5, LC-Red 640, LC-Red 705.

In the context of the invention, any primer and/or probe may be chemically modified, i.e. the primer and/or the probe comprise a modified nucleotide or a non-nucleotide compound. The probe or the primer is then a modified oligonucleotide.

A method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min. In order to not expose the respective polymerase like e.g. the Z05 DNA Polymerase to such high temperatures for too long and thus risking a loss of functional enzyme, it can be preferred to use short denaturation steps.

In an embodiment of the invention, the denaturation step is up to 30 sec, or up to 20 sec, or up to 10 sec, or up to 5 sec, or about 5 sec.

If the double-stranded template nucleic acid is denatured by heat, the reaction mixture is allowed to cool to a temperature that promotes annealing of each primer to its target sequence on the target nucleic acids.

The temperature for annealing can be from about 35° C. to about 70° C., or about 45° C. to about 65° C.; or about 50° C. to about 60° C., or about 55° C. to about 58° C. Annealing times can be from about 10 sec to about 1 min (e.g., about 20 sec to about 50 sec; about 30 sec to about 40 sec). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention the process described above comprises annealing at different temperatures, for example first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 sec to about 5 min, or about 15 sec to 2 min, or about 20 sec to about 1 min, or about 25 sec to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) can be repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Within the scope of the invention, a PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification can be preferred, as the time-to-result is reduced and leads to a possible earlier diagnosis.

Other nucleic acid amplification methods to be used in the context of the invention comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qb-amplification (for a review see e.g. Whelen A. C. and Persing D. H., Annu. Rev. Microbiol. 50 (1996) 349-373; Abramson R. D. and Myers T. W., Curr Opin Biotechnol 4 (1993) 41-47).

The internal control nucleic acid used in the present invention may exhibit the following properties relating to its sequence:
  a melting temperature from 55° C. to 90° C., or from 65° C. to 85° C., or from 70° C. to 80° C., or about 75° C.
  a length of up to 500 bases or base pairs, or from 50 to 300 bases or base pairs, or from 100 to 200 bases or base pairs, or about 180 bases or base pairs
  a GC content from 30% to 70%, or from 40% to 60%, or about 50%.

In the context of the invention, a "sequence" is the primary structure of a nucleic acid, i.e. the specific arrangement of the single nucleobases of which the respective nucleic acids consists. It has to be understood that the terra "sequence" does not denote a specific type of nucleic acid such as RNA or DNA, but applies to both as well as to other types of nucleic acids such as e.g. PNA or others. Where nucleobases correspond to each other, particularly in the case of uracil (present in RNA) and thymine (present in DNA), these bases can be considered equivalent between RNA and DNA sequences, as well-known in the pertinent art.

Clinically relevant nucleic acids are often DNA which can be derived e.g. from DNA viruses like e.g. Hepatitis B Virus (HBV), Cytomegalovirus (CMV) and others, or bacteria like e.g. *Chlamydia trachomatis* (CT), *Neisseria gonorrhoeae* (NG) and others. In such cases, it can be advantageous to use an internal control nucleic acid consisting of DNA, in order to reflect the target nucleic acids properties.

Therefore, an aspect of the invention is the method described above, wherein said internal control nucleic acid is DNA.

On the other hand, numerous nucleic acids relevant for clinical diagnostics are ribonucleic acids, like e.g. the nucleic acids from RNA viruses such as for example Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV) and others. The present invention can be readily applied to such nucleic acids. In this case, it can be advantageous to use an internal control nucleic acid consisting of RNA, in order to reflect the target nucleic acids properties. If both RNA and DNA are to be analyzed in the process described supra, the internal control nucleic acid can be RNA, as the internal control nucleic acid mimics the most sensitive target of an assay involving multiple targets, and RNA targets usually have to be more closely controlled.

Thus, an aspect of the invention is the method described above, wherein said internal control nucleic acid is RNA.

Since RNA is more prone to degradation than DNA due to influences such as alkaline pH, ribonucleases etc., internal control nucleic acids made of RNA may be provided as armored particles. Armored particles such as especially armored RNA are described e.g. in EP910643. In brief, the RNA, which can be produced chemically or heterologously e.g. by bacteria such as e.g. *E. coli*, is at least partially encapsulated in a viral coat protein. The latter confers resistance of the RNA towards external influences, in particular ribonucleases. It must be understood that internal control DNA can also be provided as an armored particle. Both armored RNA and DNA are useful as internal control nucleic acids in the context of the invention. In an embodiment, RNA control nucleic acids are armored with the MS2 coat protein in *E. coli*. In a further embodiment, DNA control nucleic acids are armored using lambda phage GT11.

Therefore, an aspect of the invention is the method described above, wherein said internal control nucleic acid is an armored nucleic acid.

Typically, in amplification-based nucleic acid diagnostics, RNA templates are transcribed into DNA prior to amplification and detection.

Hence, an aspect of the invention is the process described above, wherein said amplification reagents comprise a polymerase with reverse transcriptase activity, said process further comprising between step e. and step f. the step of incubating in said reaction vessels said purified nucleic acids with said one or more amplification reagents for a period of time and under conditions suitable for transcription of RNA by said polymerase with reverse transcriptase activity to occur.

A "polymerase with reverse transcriptase activity" is a nucleic acid polymerase capable of synthesizing DNA based on an RNA template. It is also capable of the formation of a double-stranded DNA once the RNA has been reverse transcribed into a single strand cDNA. In an embodiment of the invention, the polymerase with reverse transcriptase activity is thermostable.

In an embodiment, the process according to the invention comprises incubating a sample containing an RNA template with an oligonucleotide primer sufficiently complementary to said RNA template to hybridize with the latter, and a thermostable DNA polymerase in the presence of at least all four natural or modified deoxyribonucleoside triphosphates, in an appropriate buffer comprising a metal ion buffer which, in an embodiment, buffers both the pH and the metal ion concentration. This incubation is performed at a temperature sufficient for said primer to hybridize to said RNA template and said DNA polymerase to catalyze the polymerization of said deoxyribonucleoside triphosphates to form a cDNA sequence complementary to the sequence of said RNA template.

As used herein, the term "cDNA" refers to a complementary DNA molecule synthesized using a ribonucleic acid strand (RNA) as a template. The RNA may e.g. be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

A primer suitable for annealing to an RNA template may also be suitable for amplification by PCR. For PCR, a second primer, complementary to the reverse transcribed cDNA strand, provides an initiation site for the synthesis of an extension product.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT/PCR reaction, following reverse transcription and prior to amplification one or more of the reaction components such as the amplification reagents are e.g. adjusted, added, or diluted, for which the reaction vessel has to be opened, or at least its contents have to be manipulated. Both homogeneous and non-homogeneous embodiments are comprised by the scope of the invention.

Reverse transcription is an important step in an RT/PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, the RT incubation can be carried out at more than one different temperature.

Therefore, an aspect of the invention is the process described above, wherein said incubation of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplificates.

Thus, an aspect of the invention is the process described above, wherein the period of time for incubation of the polymerase with reverse transcriptase activity is up to 30 minutes, 20 minutes, 15 minutes, 12.5 minutes, 10 minutes, 5 minutes, or 1 minute.

A further aspect of the invention is the process described above, wherein the polymerase with reverse transcriptase activity and comprising a mutation is selected from the group consisting of
a) a CS5 DNA polymerase
b) a CS6 DNA polymerase
c) a *Thermotoga maritima* DNA polymerase
d) a *Thermus aquaticus* DNA polymerase
e) a *Thermus thermophilus* DNA polymerase
f) a *Thermus flavus* DNA polymerase
g) a *Thermus filiformis* DNA polymerase
h) a *Thermus* sp. sps17 DNA polymerase
i) a *Thermus* sp. Z05 DNA polymerase
j) a *Thermotoga neapolitana* DNA polymerase
k) a *Termosipho africanus* DNA polymerase
l) a *Thermus caldophilus* DNA polymerase Particularly suitable for these requirements are enzymes carrying a mutation in the polymerase domain that enhances their reverse transcription efficiency in tenns of a faster extension rate.

Therefore, an aspect of the invention is the process described above, wherein the polymerase with reverse transcriptase activity is a polymerase comprising a mutation conferring an improved nucleic acid extension rate and/or an improved reverse transcriptase activity relative to the respective wildtype polymerase.

In an embodiment, in the process described above, the polymerase with reverse transcriptase activity is a polymerase comprising a mutation conferring an improved reverse transcriptase activity relative to the respective wildtype polymerase.

Polymerases carrying point mutations that render them particularly useful in the context of the invention are disclosed in WO 2008/046612. In particular, polymerases to be used in the context of the present invention can be mutated DNA polymerases comprising at least the following motif in the polymerase domain:

T-G-R-L-S-S-$X_{b7}$-$X_{b8}$-P-N-L-Q-N; wherein $X_{b7}$ is an amino acid selected from S or T and wherein $X_{b8}$ is an amino acid selected from G, T, R, K, or L, wherein the polymerase comprises 3'-5' exonuclease activity and has an improved nucleic acid extension rate and/or an improved reverse transcription efficiency relative to the wildtype DNA polymerase, wherein in said wildtype DNA polymerase $X_{b8}$ is an amino acid selected from D, E or N.

One example is mutants of thermostable DNA polymerase from *Thermus* species Z05 (described e.g. in U.S. Pat. No. 5,455,170), said variations comprising mutations in the polymerase domain as compared with the respective wildtype enzyme Z05. An embodiment for the method according to the invention is a mutant Z05 DNA polymerase wherein the amino acid at position 580 is selected from the group consisting of G, T, R, K and L.

For reverse transcription using a thermostable polymerase, $Mn^{2+}$ can be the divalent cation and is typically included as a salt, for example, manganese chloride (MnCl2), manganese acetate (Mn(OAc)2), or manganese sulfate (MnSO4). If MnCl2 is included in a reaction containing 50 mM Tricine buffer, for example, the MnCl2 is generally present at a concentration of 0.5-7.0 mM; 0.8-1.4 mM is preferred when 200 mM of each dGTP, dATP, dUTP, and, dCTP are utilized; and 2.5-3.5 mM MnCl2 is most preferred. Further, the use of $Mg^{2+}$ as a divalent cation for reverse transcription is also in the context of the present invention.

Since it is in the scope of the invention to reverse-transcribe RNA target nucleic acids into cDNA while preserving the DNA target nucleic acids so both cDNA and DNA can be used for subsequent amplification, the internally controlled process described above is particularly useful for the simultaneous amplification of target nucleic acids derived from both organisms having an RNA or organisms having a DNA genome. This advantage considerably increases the spectrum of different organisms, especially pathogens, that can be analyzed under identical physical conditions.

Therefore, an aspect of the invention is the process described above, wherein the at least two target nucleic acids comprise RNA and DNA.

An "organism", as used herein, means any living single- or multicellular life form. In the context of the invention, a virus is an organism.

Especially due to an appropriate temperature optimum, enzymes like Tth polymerase or, for example, the mutant Z05 DNA polymerase mentioned above are suited to carry out the subsequent step of amplification of the target nucleic acids. Exploiting the same enzyme for both reverse transcription an amplification contributes to the ease of carrying out the process and facilitates its automation, since the fluid sample does not have to be manipulated between the RT and the amplification step.

Therefore, in an embodiment, in the process described above the same polymerase with reverse transcriptase activity is used for reverse transcription and for the amplification in step f. For example, the enzyme is the mutant Z05 DNA polymerase described supra.

In order not to expose the polymerase or other components of the reaction mixture used in the context of the invention to elevated temperatures for times longer than necessary, in an embodiment, steps above 90° C. are up to 20 sec, or up to 15 sec, or up to 10 sec, or up to 5 sec or 5 sec long. This also reduces the time-to-result and cuts down the overall required time of the assay.

In such a homogeneous setup, it can be of considerable advantage to seal the reaction vessels prior to initiating the RT and the amplification, thereby reducing the risk of contamination. Sealing can be e.g. achieved by applying a foil that can be transparent, a cap, or by oil added to the reaction vessels and forming a lipophilic phase as a sealing layer at the top of the fluid.

Thus, an aspect of the invention is the process described above, further comprising after step e. the step of sealing the at least two reaction vessels.

For the ease of handling and to facilitate automation, the at least two reaction vessels can be combined in an integral arrangement, so they can be manipulated together.

Consequently, an aspect of the invention is the process described above, wherein the at least two reaction vessels are combined in the same integral arrangement.

Integral arrangements can e.g. be vials or tubes reversibly or irreversibly attached to each other or arranged in a rack. For example, the integral arrangement is a multiwell plate.

The target of the amplification step can be an RNA/DNA hybrid molecule. The target can be a single-stranded or double-stranded nucleic acid. Although the most widely used PCR procedure uses a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule. At this point, successive cycles of amplification proceed as described above.

Since nucleic acid amplification, especially but not only in the case of PCR, is very efficient if carried out as a cycling reaction, an aspect of the invention is the process described above, wherein the amplification reaction in step f. consists of multiple cycling steps.

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid.

The amplified target nucleic acids can be detected during or after the amplification reaction in order to evaluate the result of the analysis. Particularly for detection in real time, it is advantageous to use nucleic acid probes.

Thus, an aspect of the invention is the process described above, wherein a cycling step comprises an amplification step and a hybridization step, said hybridization step comprising hybridizing the amplified nucleic acids with probes.

It can be favorable to monitor the amplification reaction in real time, i.e. to detect the target nucleic acids and/or their amplificates during the amplification itself.

Therefore, an aspect of the invention is the process described above, wherein the probes are labeled with a donor fluorescent moiety and a corresponding acceptor fluorescent moiety.

The methods set out above can be based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection can be followed by quantitating the FRET. For example, detection is performed after each cycling step. For example, detection is performed in real time. By using commercially available real-time PCR instrumentation (e.g., LightCycler™ or TaqMan®), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, CY5, JA270, Cyan and CY5.5. During the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as a mutant Z05 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, in a method according to the invention is the method described above using FRET, wherein said probes comprise a nucleic acid sequence that permits secondary structure formation, wherein said secondary structure formation results in spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in an embodiment, said donor and acceptor fluorescent moieties are within no more than 5 nucleotides of each other on said probe.

In a further embodiment, said acceptor fluorescent moiety is a quencher.

As described above, in the TaqMan format, during the annealing step of the PCR reaction, the labeled hybridization probe binds to the target nucleic acid (i.e., the amplification product) and is degraded by the 5'- to 3'-exonuclease activity of the Taq or another suitable polymerase as known by the skilled artisan, such as a mutant Z05 polymerase, during the subsequent elongation phase.

Thus, in an embodiment, in the process described above, amplification employs a polymerase enzyme having 5'- to 3'-exonuclease activity.

It is further advantageous to carefully select the length of the amplicon that is yielded as a result of the process described above. Generally, relatively short amplicons increase the efficiency of the amplification reaction. Thus, an aspect of the invention is the process described above, wherein the amplified fragments comprise up to 450 bases, up to 300 bases, up to 200 bases, or up to 150 bases.

The internal control nucleic acid used in the present invention can serve as a "quantitative standard nucleic acid" which is apt to be and used as a reference in order to quantify, i.e. to determine the quantity of the target nucleic acids. For this purpose, one or more quantitative standard nucleic acids undergo all possible sample preparation steps along with the target nucleic acids. Moreover, a quantitative standard nucleic acid is processed throughout the method within the same reaction mixture. It must generate, directly or indirectly, a detectable signal both in the presence or absence of the target nucleic acid. For this purpose, the concentration of the quantitative standard nucleic acid has to be carefully optimized in each test in order not to interfere with sensitivity but in order to generate a detectable signal also e.g. at very high target concentrations. In terms of the limit of detection (LOD, see below) of the respective assay, the concentration range for the "quantitative standard nucleic acid" is 20-5000×LOD, 20-1000×LOD, or 20-5000×LOD. The final concentration of the quantitative standard nucleic acid in the reaction mixture is dependent on the quantitative measuring range accomplished.

"Limit of detection" or "LOD" means the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The Probit Analysis can be applied at distinct "hitrates". As known in the art, a "hitrate" is commonly expressed in percent [%] and indicates the percentage of positive results at a specific concentration of an analyte. Thus for example, an LOD can be determined at 95% hitrate, which means that the LOD is calculated for a setting in which 95% of the valid results are positive.

In an embodiment, the process described above provides an LOD of 1 to 100 cp/ml or 0.5 to 50 IU/ml, or 1 to 75 cp/ml or 0.5 to 30 IU/ml, or 1 to 25 cp/ml or 1 to 20 IU/ml.

With respect to some examples of possible target nucleic acids from certain viruses, the process described above provides the following LODs:
  HIV: up to 60 cp/ml, up to 50 cp/ml, up to 40 cp/ml, up to 30 cp/ml, up to 20 cp/ml, or up to 15 cp/ml
  HBV: up to 10 IU/ml, up to 7.5 IU/ml, or up to 5 IU/ml
  HCV: up to 10 IU/ml, up to 7.5 IU/ml, or up to 5 IU/ml
  WNV I: up to 20 cp/ml, up to 15 cp/ml, or up to 10 cp/ml
  WNV II: up to 20 cp/ml, up to 15 cp/ml, up to 10 cp/ml, or up to 5 cp/ml
  JEV: up to 100 cp/ml, up to 75 cp/ml, up to 50 cp/ml, or up to 30 cp/ml
  SLEV: up to 100 cp/ml, up to 75 cp/ml, up to 50 cp/ml, up to 25 cp/ml, or up to 10 cp/ml.

An example of how to perform calculation of quantitative results in the TaqMan format based on an internal control nucleic acid serving as a quantitative standard nucleic acid is described in the following: A titer is calculated from input data of instrument-corrected fluorescence values from an entire PCR run. A set of samples containing a target nucleic acid and an internal control nucleic acid serving as a quantitative standard nucleic acid undergo PCR on a thermocycler using a specified temperature profile. At selected temperatures and times during the PCR profile samples are illuminated by filtered light and the filtered fluorescence data are collected for each sample for the target nucleic acid and the internal control nucleic acid. After a PCR run is complete, the fluorescence readings are processed to yield one set of dye concentration data for the internal control nucleic acid and one set of dye concentration data for the target nucleic acid. Each set of dye concentration data is processed in the same manner. After several plausibility checks, the elbow values (CT) are calculated for the internal control nucleic acid and the target nucleic acid. The elbow value is defined as the point where the fluorescence of the target nucleic acid or the internal control nucleic acid crosses a predefined threshold (fluorescence concentration). Titer determination is based on the assumptions that the target nucleic acid and the internal control nucleic acid are amplified with the same efficiency and that at the calculated elbow value equal amounts of amplicon copies of target nucleic acid and internal control nucleic acid are amplified and detected. Therefore, the (CTQS−CTtarget) is linear to log(target conc/QS conc). In this context, QS denotes the internal control nucleic acid serving as a quantitative standard nucleic acid. The titer T can then be calculated for instance by using a polynomial calibration formula as in the following equation:

$$T' = 10(a(CTQS-CTtarget)2 + b(CTQS-CTtarget) + c)$$

The polynomial constants and the concentration of the quantitative standard nucleic acid are known, therefore the only variable in the equation is the difference (CTQS−CTtarget).

Further, in the sense of the invention, the internal control nucleic acid can serve as a "qualitative internal control nucleic acid". A "qualitative internal control nucleic acid" is particularly useful for confirming the validity of the test result of a qualitative detection assay: Even in the case of a negative result, the qualitative internal control must be detected, otherwise the test itself is considered to be inoperative. However, in a qualitative setup, it does not necessarily have to be detected in case of a positive result. As a consequence, its concentration must be relatively low. It has to be carefully adapted to the respective assay and its sensitivity. For example, the concentration range for the qualitative internal nucleic acid, i.e. the second control nucleic acid, will comprise a range of 1 copy per reaction to 1000 copies per reaction. In relation to the respective assay's limit of detection (LOD), its concentration is between the LOD of an assay and the 25 fold value of the LOD, or between the LOD and 10×LOD. Or, it is between 2× and 10×LOD. Or, it is between 5× and 10×LOD. Or, it is 5× or 10×LOD.

The internal control nucleic acid as used in the present invention is not restricted to a particular sequence. It can be advantageous to add different internal control nucleic acids to a fluid samples, but to use only one of them for amplification e.g. by adding only primers for one of said internal control nucleic acids. In such embodiments, the internal control nucleic acid to be amplified in a certain experiment can be chosen by the person skilled in the art, thus increasing flexibility of the analysis to be carried out. In particularly advantageous embodiments, said different internal control nucleic acids can be comprised by a single nucleic acid construct, e.g. a plasmid or a different suitable nucleic acid molecule.

Therefore, an aspect of the invention is the process described above, wherein more than one internal control nucleic acid is added in step a., but only one of said internal control nucleic acids is amplified in step f.

The results described above may be adulterated and, for example, comprise false-positives, in the case of cross-contamination with nucleic acids from sources other than the fluid sample. In particular, amplificates of former experiments may contribute to such undesired effects. One particular method for minimizing the effects of cross-contamination of nucleic acid amplification is described in U.S. Pat. No. 5,035,996. The method involves the introduction of unconventional nucleotide bases, such as dUTP, into the amplified product and exposing carryover products to enzymatic and/or physicochemical treatment to render the product DNA incapable of serving as a template for subsequent amplifications. Enzymes for such treatments are known in the art. For example, uracil-DNA glycosylase, also known as uracil-N-glycosylase or UNG, will remove uracil residues from PCR products containing that base. The enzyme treatment results in degradation of the contaminating carryover PCR product and serves to "sterilize" the amplification reaction.

Thus, an aspect of the invention is the process described above, further comprising between step d) and step e) the steps of
treating the fluid sample with an enzyme under conditions in which products from amplifications of cross-contaminating nucleic acids from other samples are enzymatically degraded;
inactivating said enzyme.

For example, the enzyme is uracil-N-glycosylase.

In a process according to the invention, all steps are automated. "Automated" means that the steps of a process are suitable to be carried out with an apparatus or machine capable of operating with little or no external control or influence by a human being. Only the preparation steps for the method may have to be done by hand, e.g. storage containers have to be filled and put into place, the choice of samples has to be performed by a human being and further steps known to the expert in the field, e.g. the operation of a controlling computer. The apparatus or machine may e.g. automatically add liquids, mix the samples or carry out incubation steps at specific temperatures. Typically, such a machine or apparatus is a robot controlled by a computer which carries out a program in which the single steps and commands are specified.

A further aspect of the invention is an analytical system (440) for isolating and simultaneously amplifying at least two target nucleic acids that may be present in a fluid sample, said analytical system comprising the following modules:
a separation station (230) comprising a solid support material, said separation station being constructed and arranged to separate and purify a target nucleic acid comprised in a fluid sample
an amplification station (405) comprising at least two reaction vessels, said reaction vessels comprising amplification reagents, at least a first purified target nucleic acid in at least a first reaction vessel and at least a second purified target nucleic acid in at least a second reaction vessel, wherein the second target nucleic acid is absent from the first reaction vessel, an internal control nucleic acid and a polymerase with reverse transcriptase activity, said polymerase further comprising a mutation conferring an improved nucleic acid extension rate and/or an improved reverse transcriptase activity relative to the respective wildtype polymerase.

An "analytical system" is an arrangement of components such as instruments interacting with each other with the ultimate aim to analyze a given sample.

The advantages of said analytical system are the same as described supra with respect to the process according to the invention.

The analytical system (440, FIG. 11) of the present invention is a system (440) comprising a module (401) for isolating and/or purifying an analyte. Further, the system (440) additionally comprises a module (403) for analyzing said analyte to obtain a detectable signal. The detectable signal can be detected in the same module (401, 402, 403) or, alternatively, in a separate module. The term "module" as used herein relates to any spatially defined location within the analyzer (400). Two modules (401, 403) can be separated by walls, or can be in open relationship. Any one module (401, 402, 403) can be either autonomously controlled, or control of the module (401, 402, 403) can be shared with other modules. For example, all modules are controlled centrally. Transfer between modules (401, 402, 403) can be manual, or automated. Thus, a number of different embodiments of automated analyzers (400) are encompassed by the present invention.

The "separation station" is described supra.

An "amplification station" comprises a temperature-controlled incubator for incubating the contents of at least two reaction vessels. It further comprises a variety of reaction vessels like tubes or plates, in which a reaction for the analysis of the sample such as PCR takes place. The outer limits or walls of such vessels are chemically inert such that they do not interfere with the amplification reaction taking place within. For the ease of handling and to facilitate automation, the at least two reaction vessels can be combined in an integral arrangement, so they can be manipulated together.

Consequently, an aspect of the invention is the analytical system described above, wherein the at least two reaction vessels are combined in an integral arrangement.

Integral arrangements can e.g. be vials or tubes reversibly or irreversibly attached to each other or arranged in a rack. For example, the integral arrangement is a multiwell plate.

For example, said multiwell plate is held in a holding station. In an embodiment, one handler transports a multiwell vessel from a holding station to an air-lock (460), and a second handler transports said multiwell plate from said airlock to said amplification station, wherein both handlers interact with said multiwell plate by a form-locking interaction.

In an embodiment, the analytical system is fully automated.

In one embodiment, at least two reaction vessels combined in an integral arrangement are transported between stations of the system.

In a second embodiment, the purified target nucleic acid is transferred from said separation station to said amplification station. For example, a pipettor comprising pipets with attached pipet tips transfers the liquid comprising the purified nucleic acid.

In a third embodiment, the purified nucleic acid is transferred from said separation station to a reaction vessel in an integral arrangement held in a holding station. For example, said reaction vessel in an integral arrangement is then transferred from said holding station to said amplification station.

The analytical system according to the invention further comprises a pipetting unit. Said pipetting unit comprises at least one pipet, or multiple pipets. In an embodiment, said multiple pipets are combined in one or more integral arrangements, within which the pipets can be manipulated individually. Pipets used in the context of the invention can be pipets comprising pipet tips as described supra. In another embodiment, the pipets are pipetting needles.

Alternatively, a reaction vessel or arrangement of reaction vessels used for sample preparation in the separation station and containing the fluid comprising the purified target nucleic acids may be transferred from the separation station to the amplification station.

For this purpose, the analytical system according to the invention further comprises a transfer unit, said transfer unit comprising a robotic device, said device comprising a handler.

For the reasons set out above in the context of the process according to the invention, the following are further aspects of the invention:

The analytical system (440) described above wherein at least one reaction vessel comprises an RNA target nucleic acid and a DNA target nucleic acid.

The analytical system (440) described above, wherein at least one reaction vessel comprises an RNA target nucleic acid, and at least one other reaction vessel comprises a DNA target nucleic acid.

For example, the analytical system (440) described above further comprises one or more elements selected from the group consisting of:
  a detection module (403) for detecting signals evoked by an analyte
  a sealer (410)
  a storage module (1008) for reagents and/or disposables.
  a control unit (1006) for controlling system components.

A "detection module" (403) can e.g. be an optical detection unit for detecting the result or the effect of the amplification procedure. An optical detection unit may comprise a light source, e.g. a xenon lamp, optics such as mirrors, lenses, optical filters, fiber optics for guiding and filtering the light, one or more reference channels, or a CCD camera or a different camera.

A "sealer" (410) is constructed and arranged to seal any vessels used in connection with the analytical system according to the invention. Such a sealer can, for example, seal tubes with appropriate caps, or multiwell plates with foil, or other suitable sealing materials.

A "storage module" (1008) stores the necessary reagents to bring about a chemical or biological reaction important for analysis of the fluid sample. It can also comprise further components useful for the method of the invention, e.g. disposables such as pipet tips or vessels to be used as reaction vessels within the separation station and/or the amplification station.

For example, the analytical system according to the invention further comprises a control unit for controlling system components.

Such a "control unit" (1006) may comprise software for ensuring that the different components of said analytical system work and interact correctly and with the correct timing, e.g. moving and manipulating components such as pipets in a coordinated manner. The control unit may also comprise a processor running a real-time operating system (RTOS), which is a multi-tasking operating system intended for real-time applications. In other words the system processor is capable of managing real-time constraints, i.e. operational deadlines from event to system response regardless of system load. It controls in real time that different units within the system operate and respond correctly according to given instructions.

In an embodiment, the present invention relates to an analytical system (440) for processing an analyte, comprising
a. a first position comprising first receptacles (1001) in linear arrangement comprising liquid samples (1010), a processing plate (101) comprising receptacles (103) in n×m arrangement for holding a liquid sample (1011), a first pipetting device (700) comprising at least two pipetting units (702) in linear arrangement, wherein said pipetting units (702) are coupled to pipette tips (3, 4), and a tip rack (70) comprising pipette tips (3, 4) in an a×(n×m) arrangement;
b. a second position comprising a holder (201, 128) for said processing plate (101), a holder (330) for a multiwell plate, a holder (470) for said tip rack (70) and a second pipetting device (35), said second pipetting device (35) comprising pipetting units (702) in an n×m arrangement for coupling to pipette tips (3, 4) (FIG. 12). The term "holder" as used herein relates to any arrangement capable of receiving a rack or a processing plate.

The advantages of the analytical system (440) of the present invention are as described above for the method of the present invention.

For example, the position of said pipetting units (702) of the first pipetting device (700) are variable. Exemplary embodiments of said first pipetting device (700) are described hereinafter.

In one embodiment, the tip rack (70) comprises pipette tips (3, 4) in an a×(n×m) arrangement. For example, a first type (4) and a second type (3) of pipette tips are comprised in the tip rack (70). In this embodiment, the first type of pipette tips (4) is arranged in an n×m arrangement, and the second type of pipette tips (3) is arranged in the n×m arrangement. In this context, "n" denotes the number of rows and m the number of columns, wherein n is 6 and m is 8. For example, the first type of pipette tips (4) has a different volume than the second type of pipette tips (3), or, the volume of the first type of pipette tips (4) is more than 500 ul, and the volume of the second type of pipette tips (3) is less than 500 ul. In this embodiment, a=2. However, embodiments of the invention with more than two types of pipette tips, and thus a>2 are also included in the present invention.

In one aspect, the analytical system (440) of the present invention comprises a control unit (1006) for allocating sample types and individual tests to individual positions of said processing plate (101). For example, said positions are separate cells (401, 402).

In one aspect of the invention, the system additionally comprises a transfer system (480) for transferring said process plate (101) and said rack (70) between first (402) and second (401) positions. Embodiments of said transfer system (480) are conveyor belts or, one or more handler.

Furthermore, for example said pipette units of said second pipetting device (35) are engaged to pipette tips (3, 4) which were used in the first position (402).

An embodiment of the system (440) of the present invention additionally comprises a third station (403) comprising a temperature-controlled incubator for incubating said analyte with reagents necessary to obtain a detectable signal. Further embodiments of this system are described hereinafter.

More optimal control of the allocation of samples and tests to the n×m arrangement is achieved with a first processor (1004) which is comprised in said first position (402) to which said control unit (1006) transfers instructions for allocating sample types and individual tests to specific positions in the n×m arrangement of vessels (103) of the process plate (101), and a second processor (1005) which is comprised in said second position (401) to which said control unit (1006) transfers instructions for allocating sample types and individual tests to specific positions in the n×m arrangement of vessels (103) of the process plate.

For example, said system additionally comprises a first processor located in said first position, and a second processor located in said second position.

For example, said first processor (1004) controls said first pipetting device (700) and said second processor (1005) controls said second pipetting device (35).

All other embodiments and specific descriptions of embodiments of the analytical system according to the invention are those mentioned for the process according to the invention.

Arrows pointing down denote addition of a component or reagent to each respective well of the deepwell plate mentioned above, arrows pointing up their respective removal. These actions were performed manually in steps 2, 3, 4, 21 and 22, by the process head of the apparatus in steps 10, 14, 16, 18, and 24, and by the reagent head of the apparatus in steps 5, 6, 7, 11, 15 and 19.

It has to be understood that the volumes used can be adjusted flexibly within the spirit of the invention, for example at least about up to 30% of the disclosed values. In particular, in the case of step 2, the sample volume can be variable in order to take into account the different types of fluid samples which may require more or less starting material for obtaining proper results, as known by the artisan. For example, the range is from about 100 ul to about 850 ul. Or, it is about 100 ul, about 500 ul or about 850 ul. For example, the volume in the respective vessels is adjusted to an identical total volume with the diluent in step 3. For example, as in the scheme shown in FIG. 1, the total volume adds up to about 850 ul.

FIG. 2*a-g* Growth curves of the amplifications of the target nucleic acids derived from HIV, HBV and CT carried out on a LightCycler480 (Roche Diagnostics GmbH, Mannheim, DE) as described in Example 1. The "Signal" indicated on the y-axis is a normalized fluorescent signal. The x-axis shows the number of the respective PCR cycle.

The growth curves of HIV and HBV are shown along with the growth curves of the corresponding internal control nucleic acid. The respective target nucleic acid curves are represented by straight lines, the control nucleic acid curves by dotted lines.

FIG. 2*a*: Qualitative HIV assay, measured in the channel for detection of the target probe.

Figure 2B:
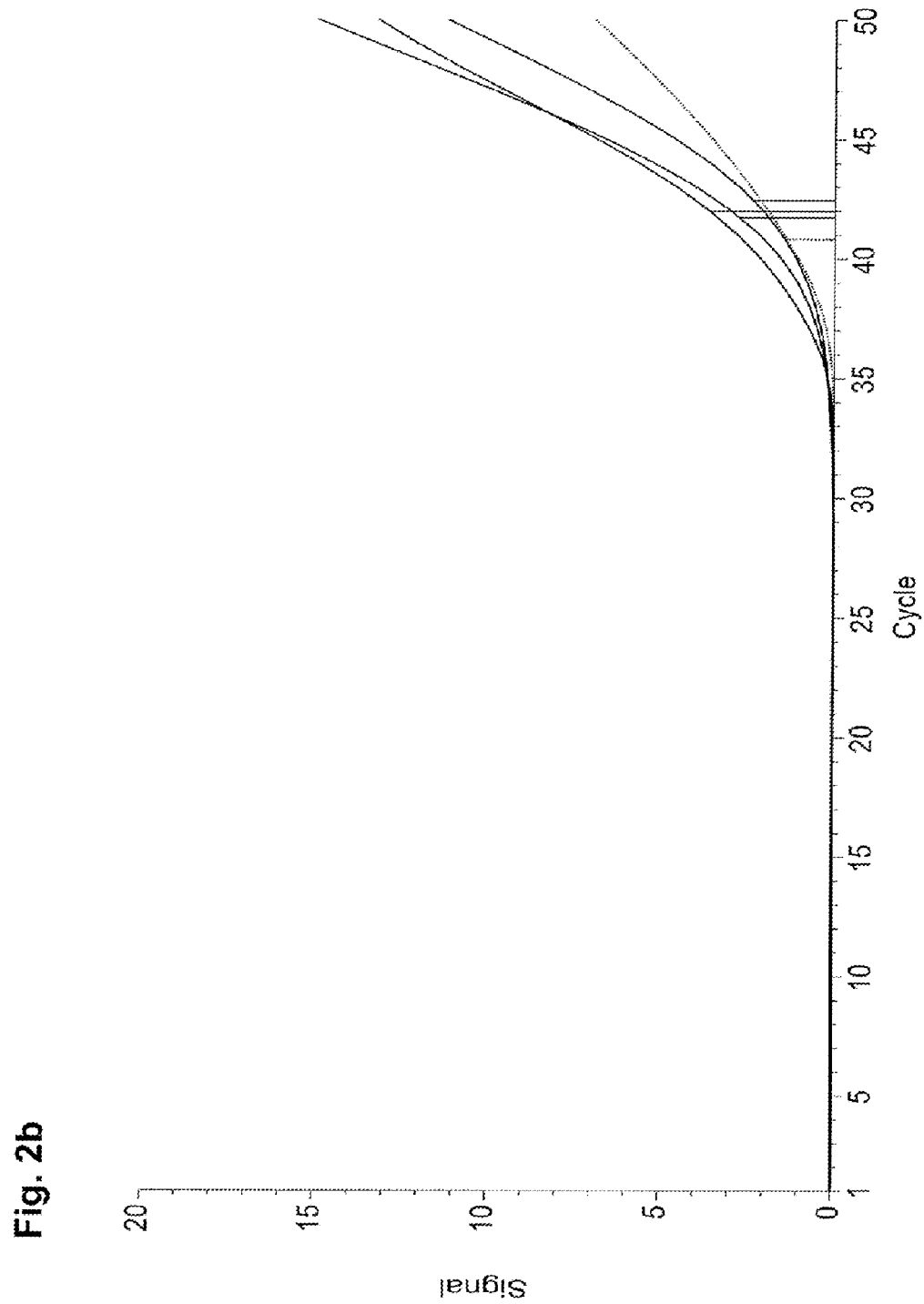

FIG. 2*b*: Qualitative HIV assay, measured in the channel for detection of the control probe.

FIG. 2*c*: Quantitative HIV assay, measured in the channel for detection of the target probe.

FIG. 2*d*: Quantitative HIV assay, measured in the channel for detection of the control probe.

Figure 2E:
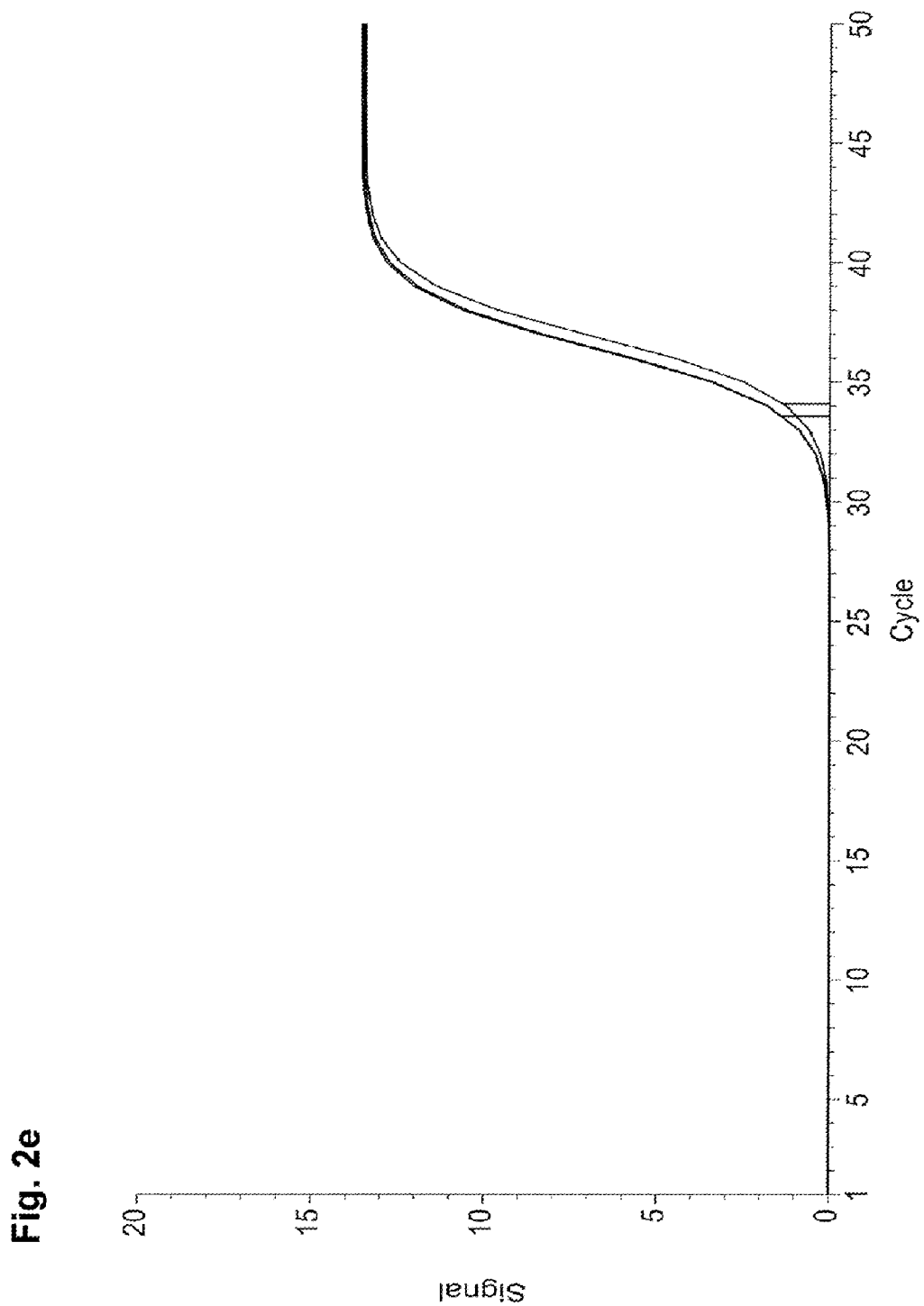

FIG. 2*e*: Quantitative HBV assay, measured in the channel for detection of the target probe.

Figure 2F:
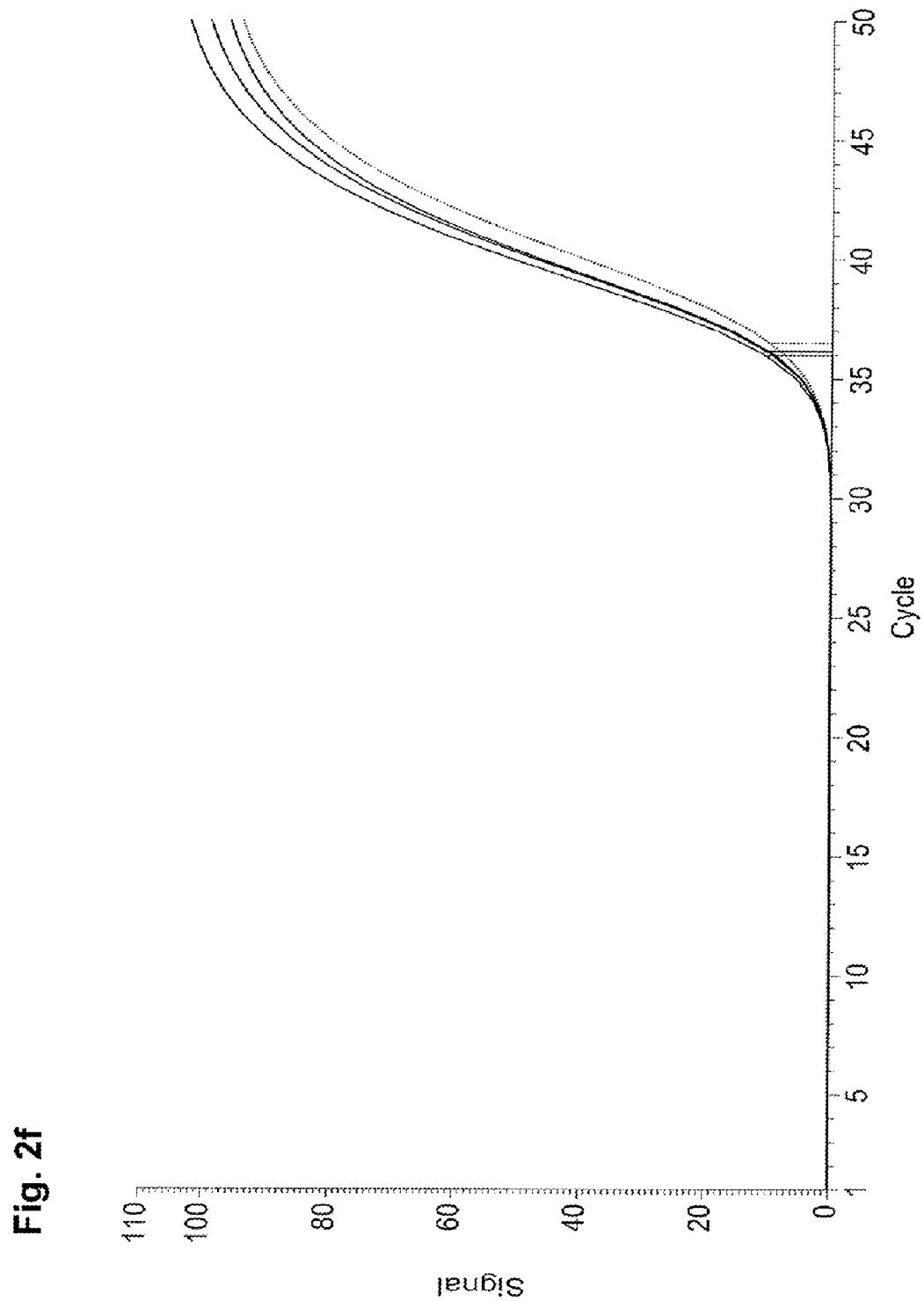

FIG. 2*f*: Quantitative HBV assay, measured in the channel for detection of the control probe.

FIG. 2*g*: CT assay, measured in the channel for detection of the target probe.

FIG. 3: Perspective view of the processing plate.

FIG. 4: Perspective view of the processing plate from the opposite angle.

FIG. 5: Top view of the processing plate.

Figure 6:
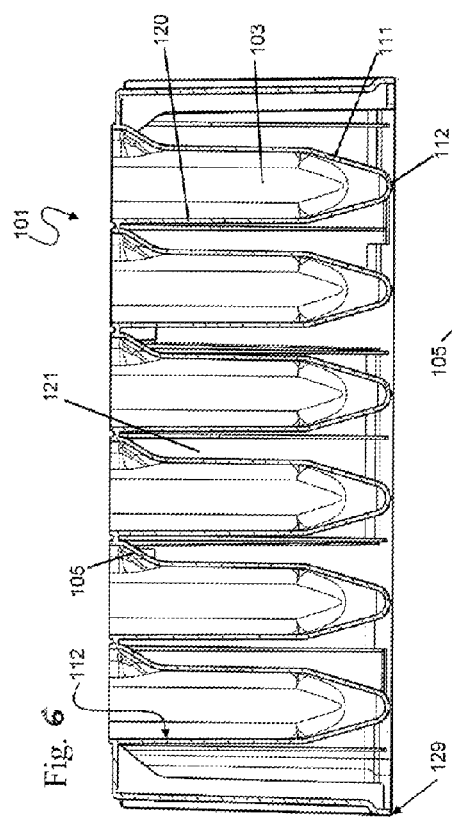

FIG. 6: Cross-sectional view along the longer side of the processing plate.

Figure 7:
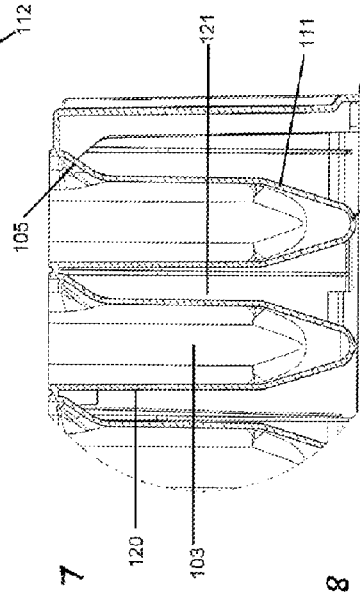

FIG. 7: A partial view of the cross-sectional view.

Figure 8:
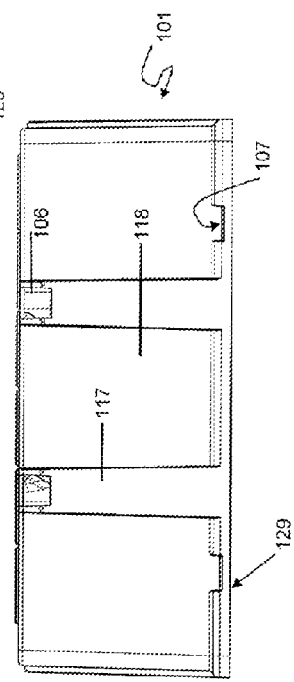

FIG. 8: Perspective view of the longer side of the processing plate.

Figure 9:
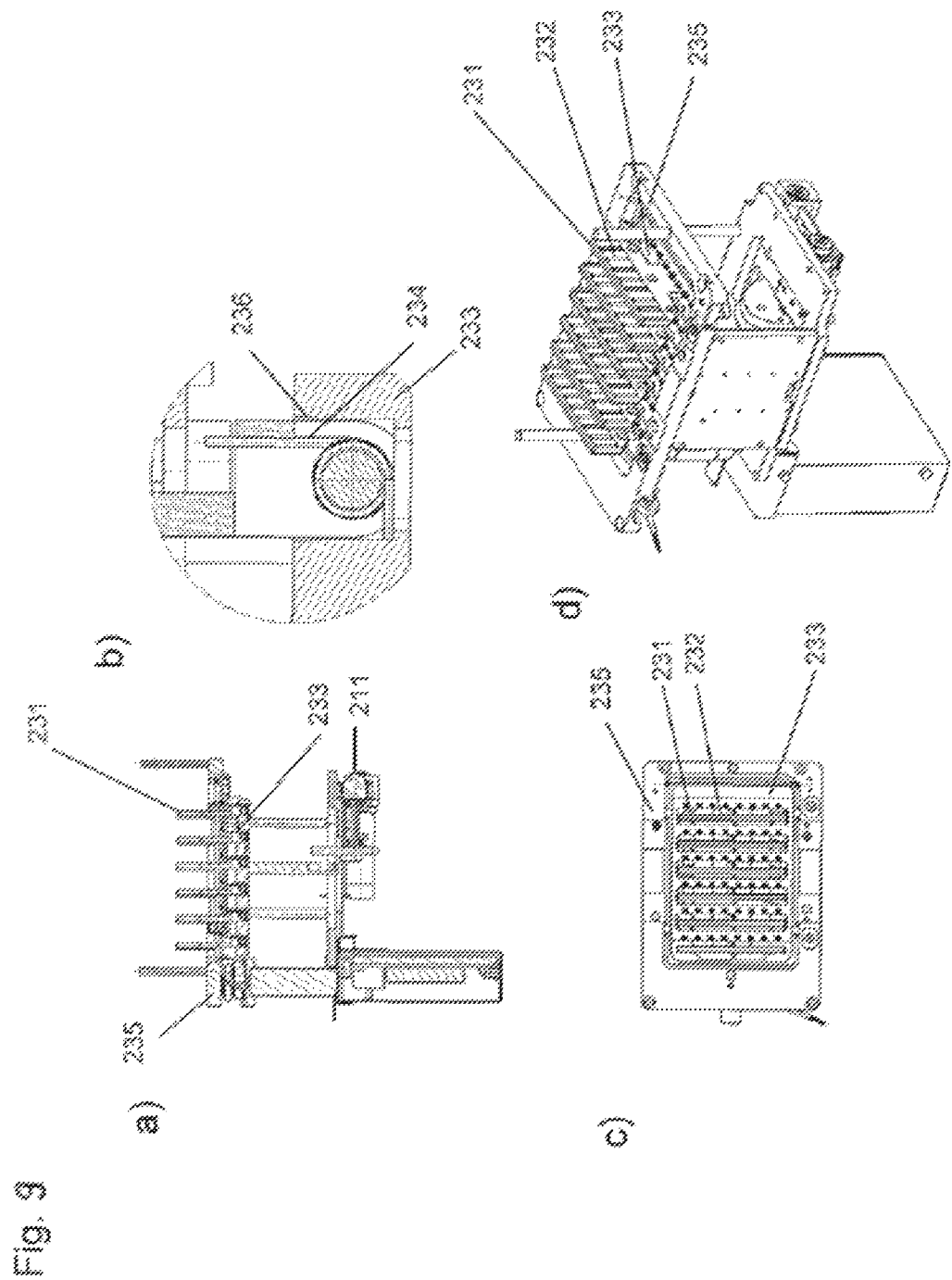

FIG. 9: *a*) to *d*) show different views of the second embodiment of the magnetic separation station.

Figure 10:
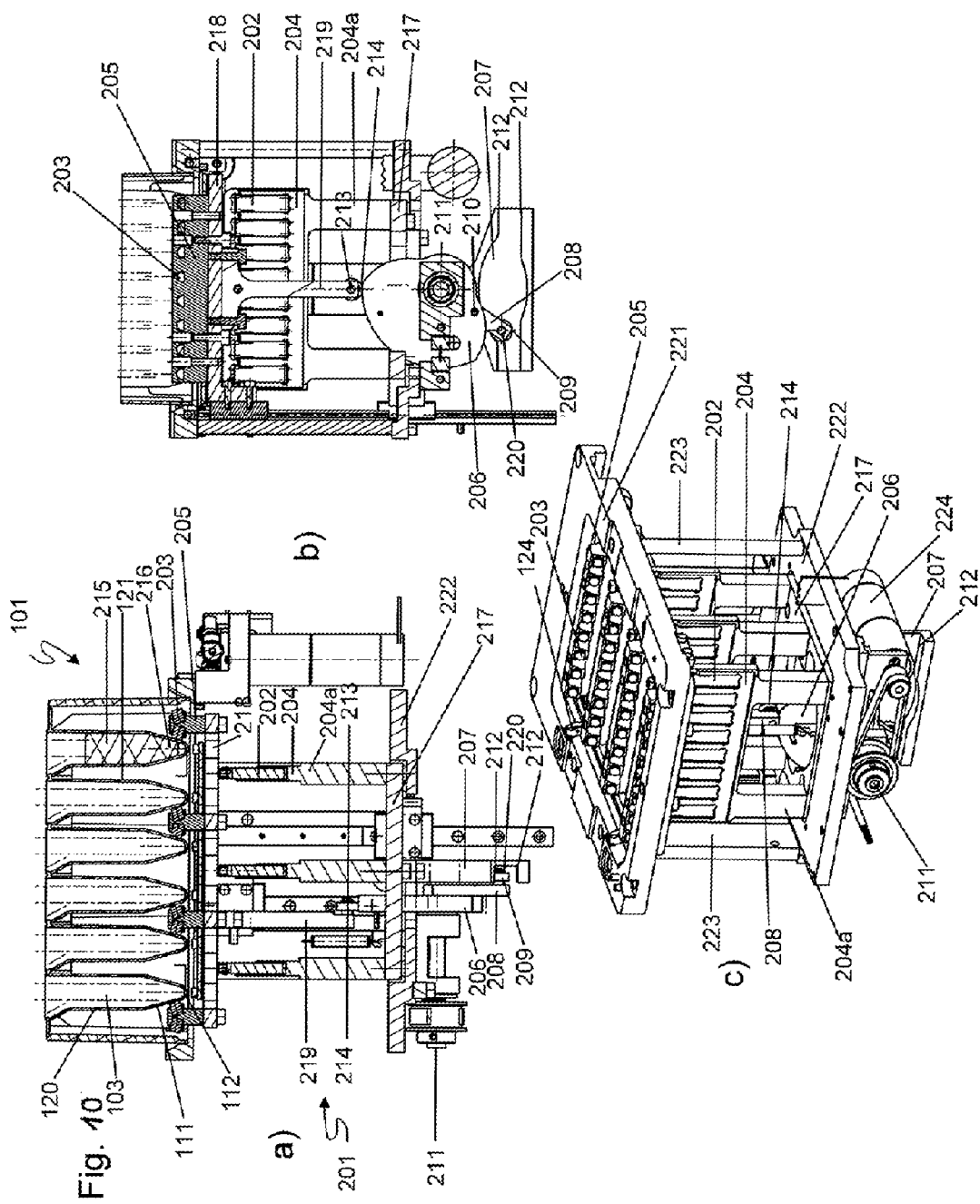

FIG. 10: (*a*) to (*c*) show a view of the first embodiment of the magnetic separation station holding the Processing plate, with the first type of magnets in the uppermost Z-position, and the second type of magnets in the lowermost Z-position.

Figure 11:
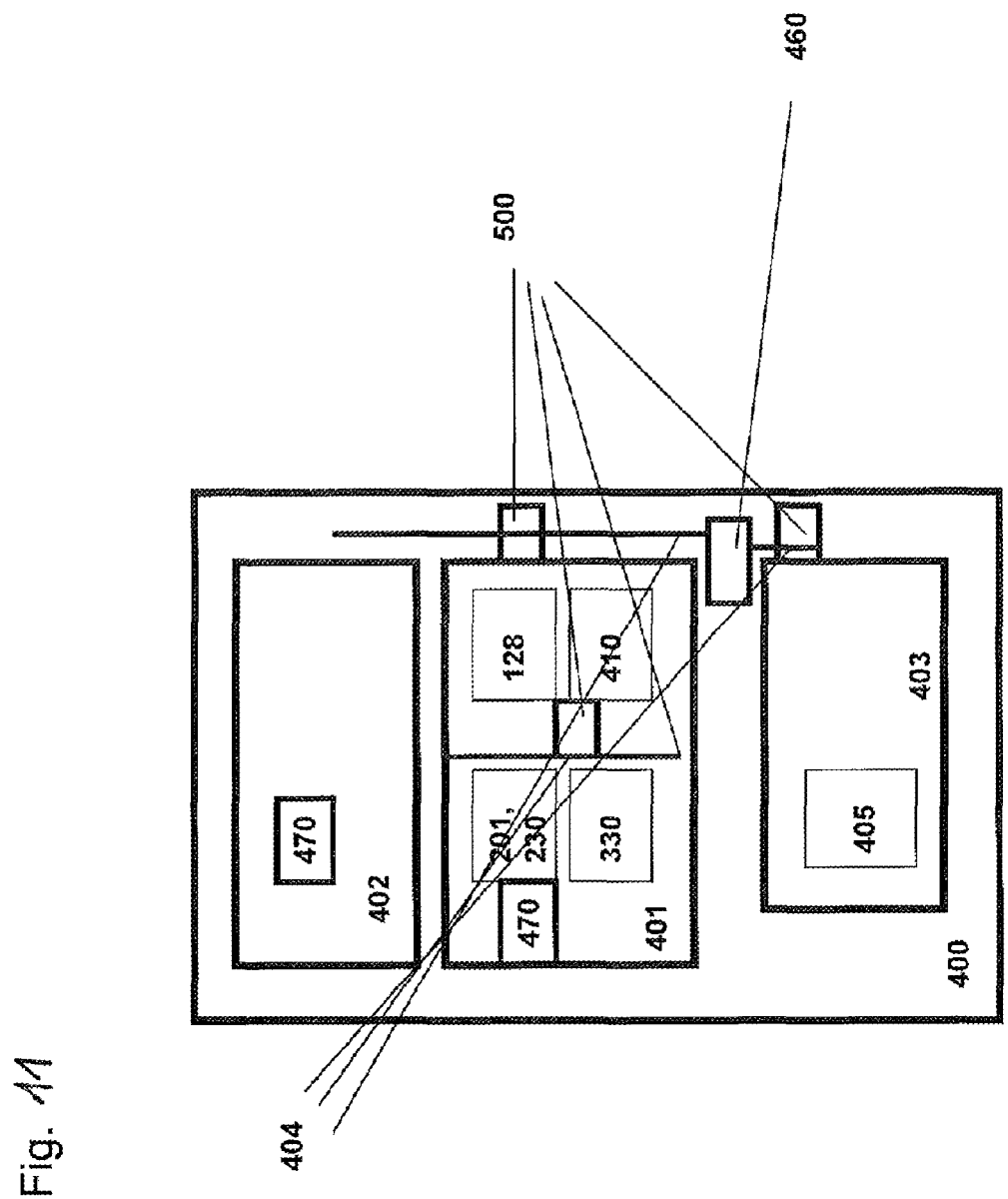

FIG. 11: Schematic drawings of an analyzer comprising different stations, modules or cells.

Figure 12:
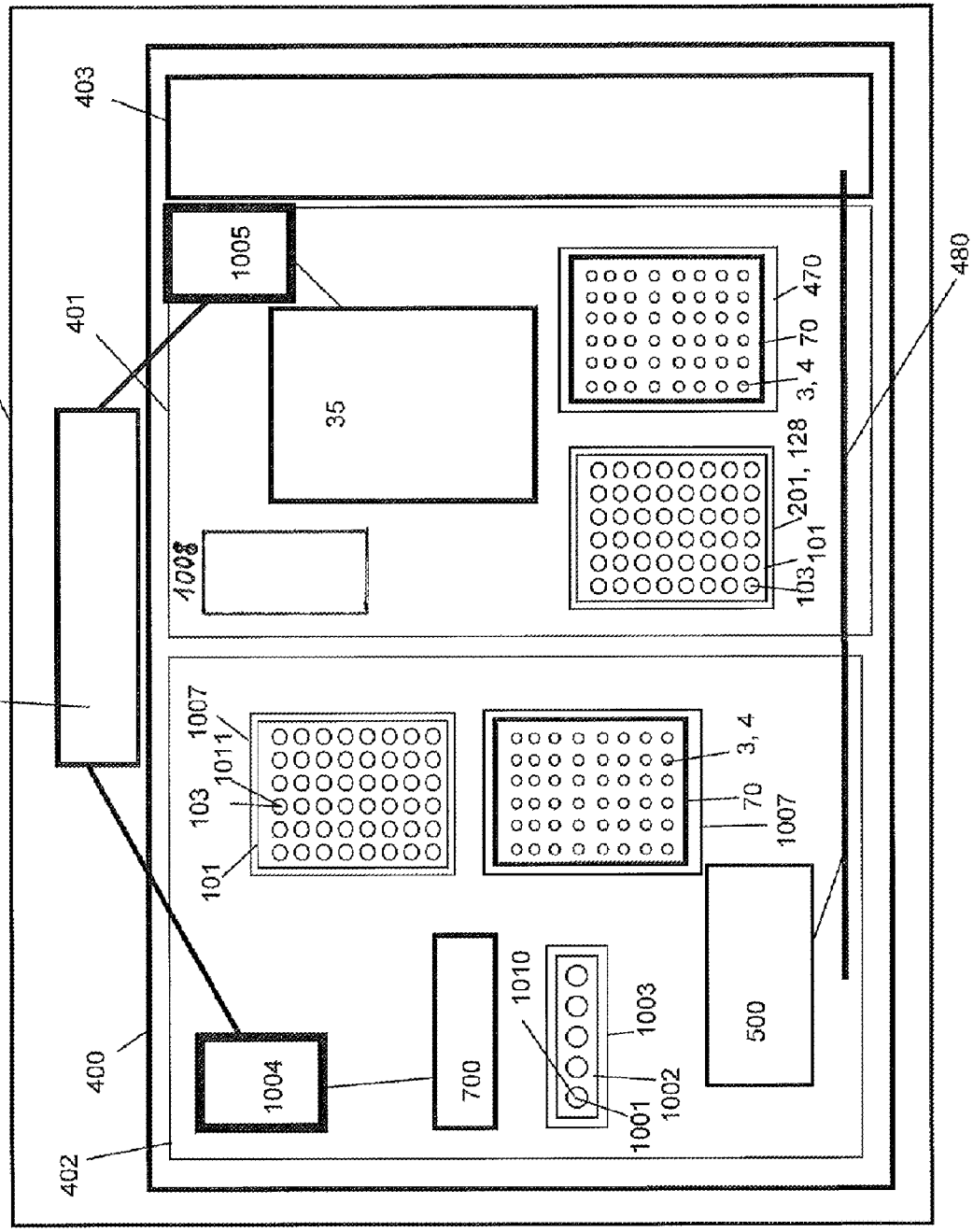

FIG. 12: Shows an analytical system of the present invention.

Figure 13:
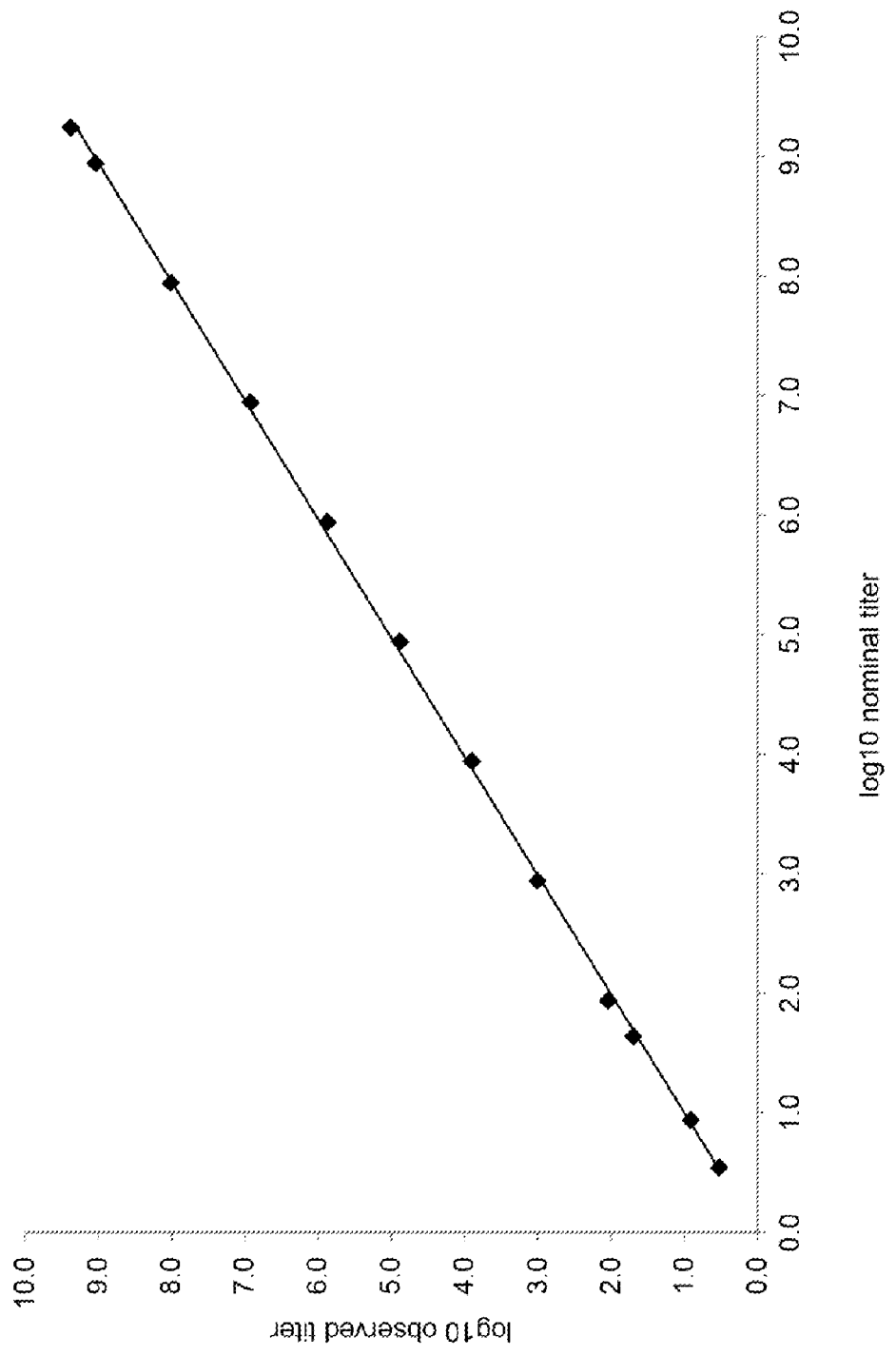

FIG. 13: Linearity of the quantitative HBV assay in EDTA plasma according to the data in Example 2.

Figure 14:
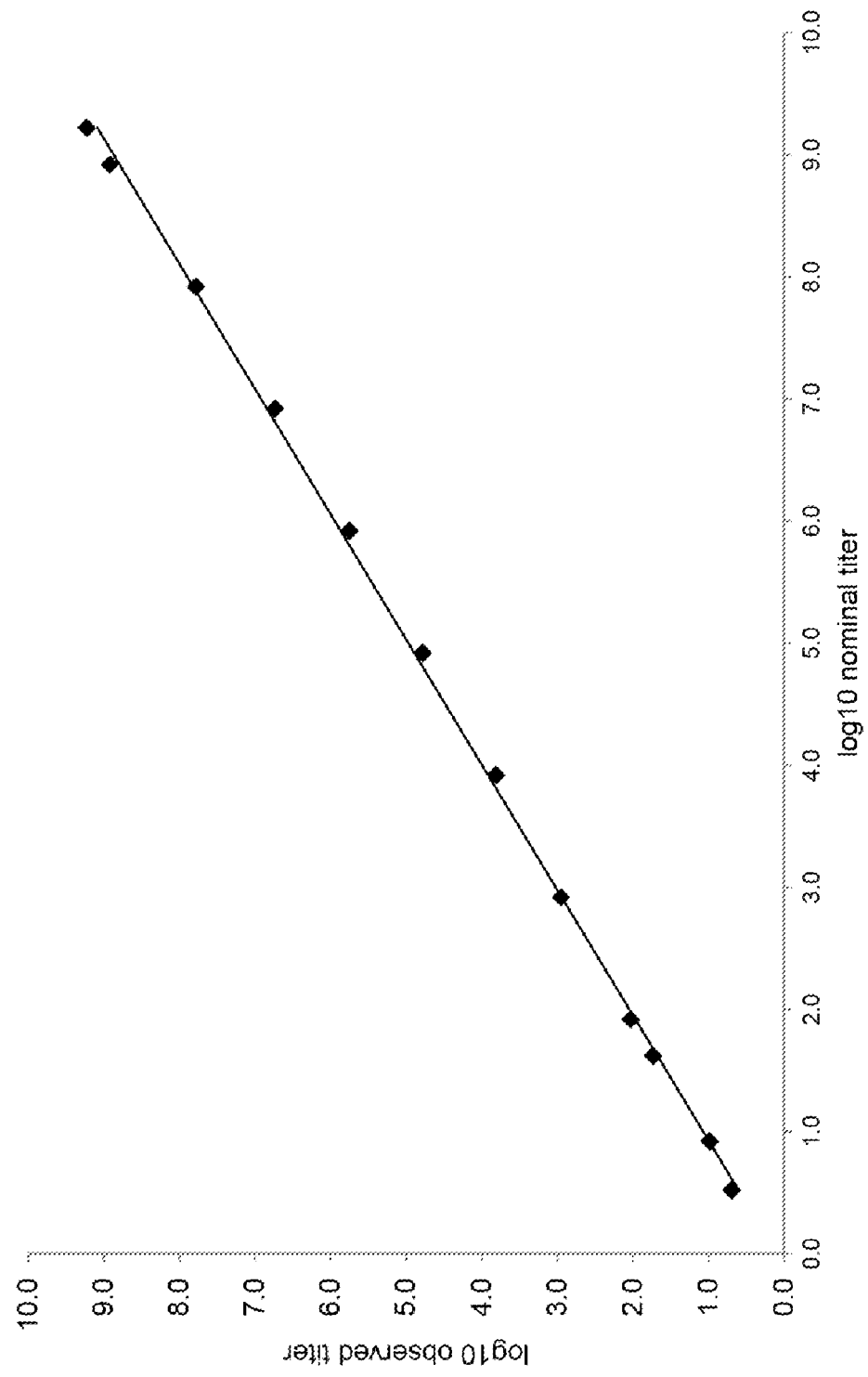

FIG. 14: Linearity of the quantitative HBV assay in serum according to the data in Example 2.

Figure 15:
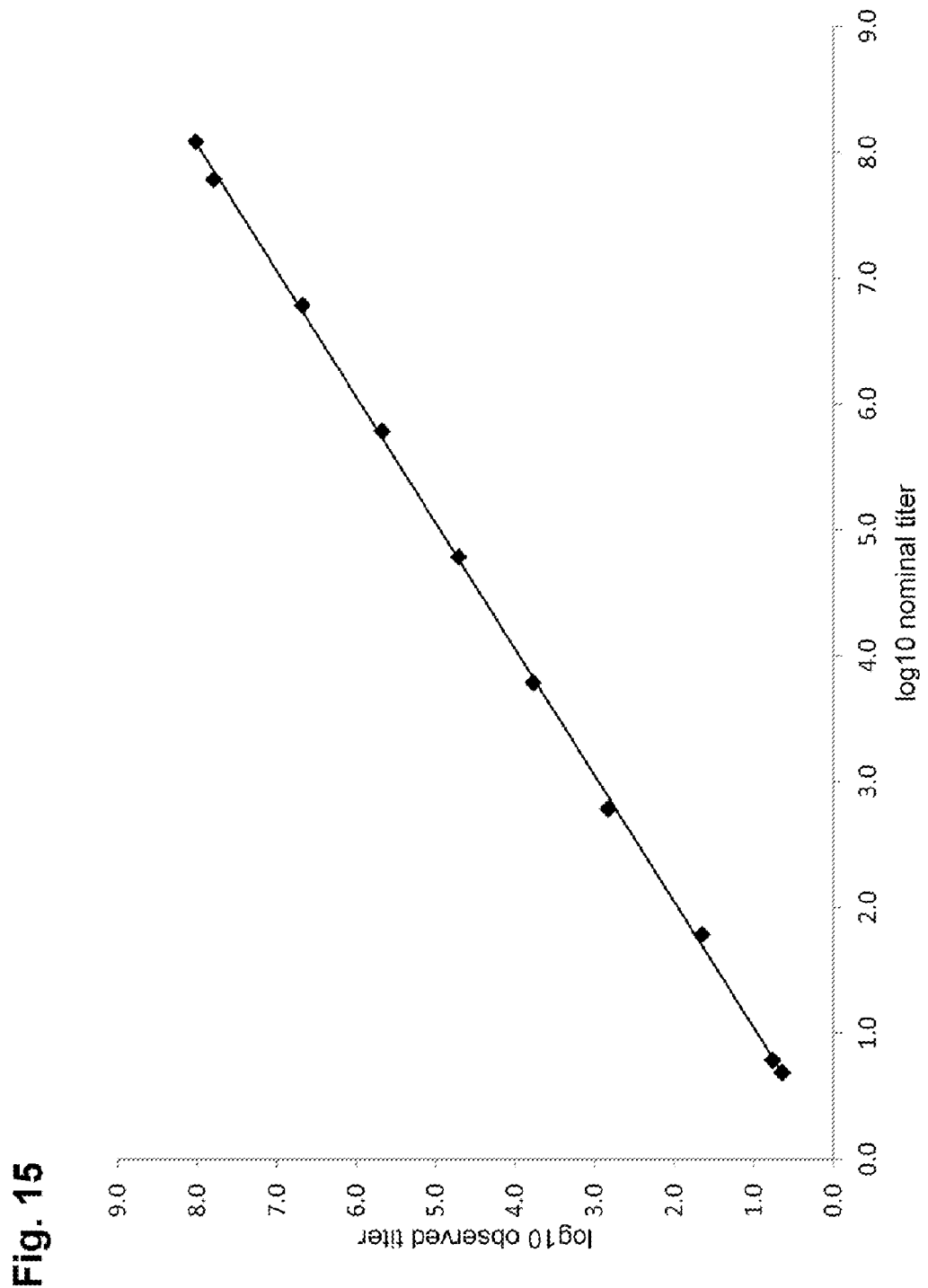

FIG. 15: Linearity of the quantitative HCV assay in EDTA plasma according to the data in Example 2.

Figure 16:
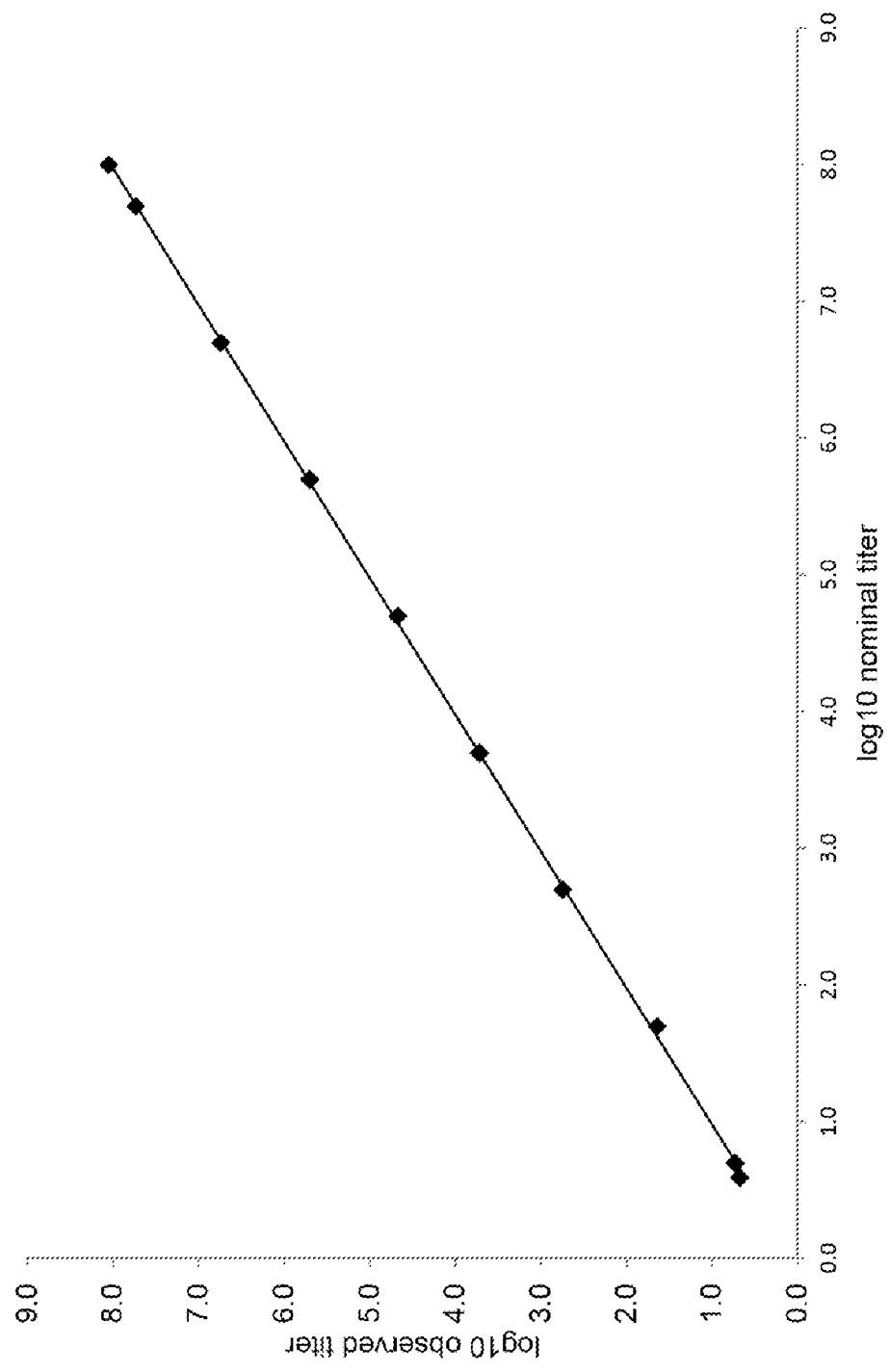

FIG. 16: Linearity of the quantitative HCV assay in serum according to the data in Example 2.

Figure 17:
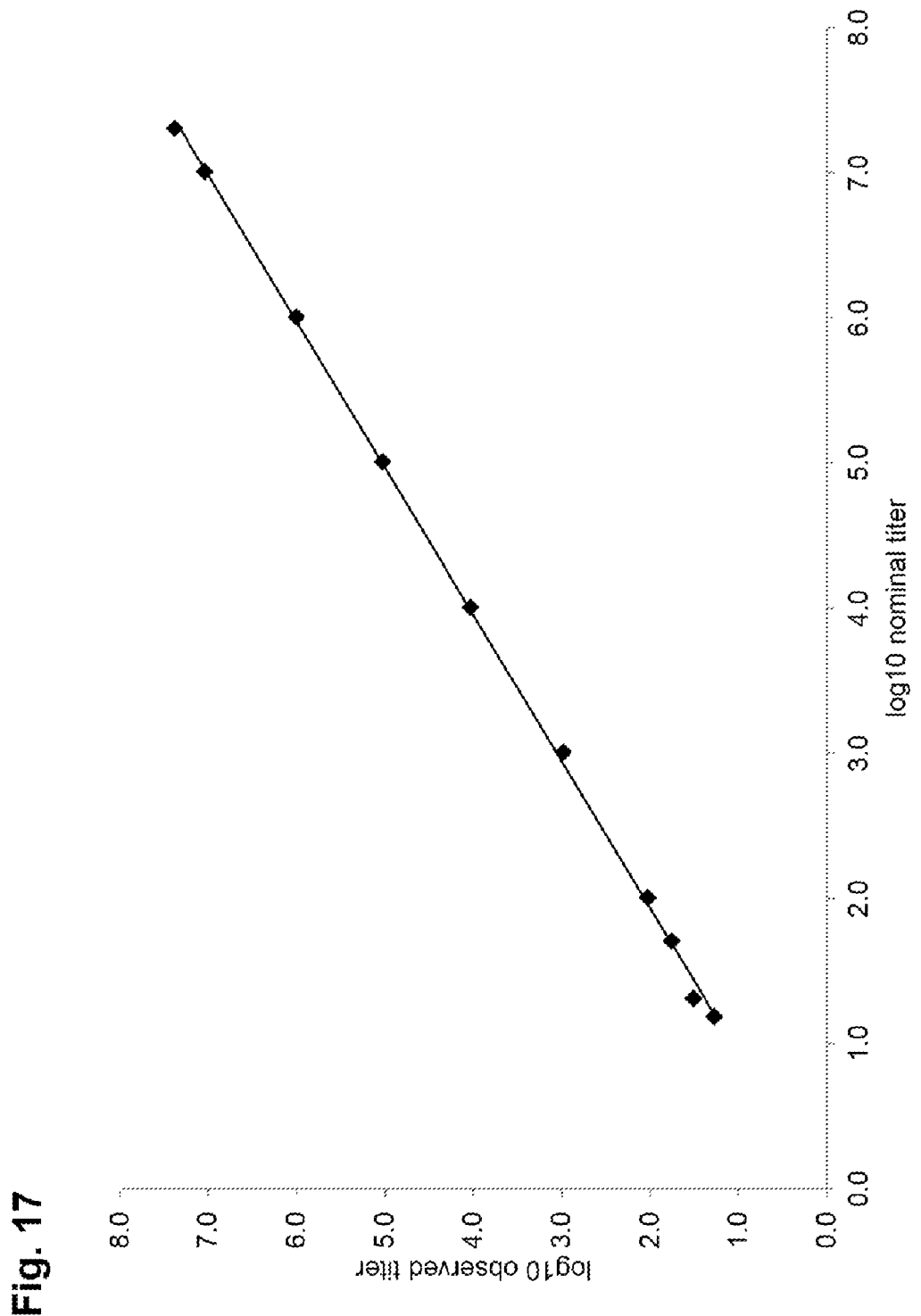

FIG. 17: Linearity of the quantitative HIV assay in EDTA plasma according to the data in Example 2.

EXAMPLES

The following examples are offered to illustrate, but not to limit the claimed invention.

Example 1

This example describes a process for isolating and simultaneously amplifying at least a first and a second target nucleic acid using a single generic internal control nucleic acid.

In brief, in the depicted embodiment, realtime PCR is carried out simultaneously and under identical conditions on a panel of several different targets comprising bacteria (*Chlamydia trachomatis*, CT) as well as a DNA virus (HBV) and an RNA virus (HIV). All samples were processed and analyzed within the same experiment, i.e. on the same deepwell plate (for sample preparation) or multiwell plate (for amplification and detection), respectively.

The following samples were prepared and subsequently analyzed:

| Reagent | Manufacturer: |
| --- | --- |
| HIV-1M Secondary Standard, 50'000 cp/ML | Roche |
| HBV Secondary Standard, 400 IU/ml | Roche |
| CT (DNA POS CTL pCHL-1) | Roche |

Suitable standards or other types of targets are available to the skilled artisan.

The instruments listed in the following table were used according to the instructions of the respective manufacturer:

| Instrument | Manufacturer |
| --- | --- |
| Hamilton Star | Hamilton Medical AG (Bonaduz, CH) |
| Light Cycler 480 | Roche Diagnostics GmbH (Mannheim, DE) |
| Chameleon Sealer | K biosystems (Essex, UK) |
| Compressor | K biosystems (Essex, UK) |

For sample preparation the following reagents were used as diluents:

| Reagent | Manufacturer: |
| --- | --- |
| PreservCyt | Thin Prep |
| K3 EDTA Plasma, PCR neg. | Roche |

The following dilutions were prepared in advance and stored overnight (plasma dilutions at −60 to −90° C., PreservCyt dilutions at 2-8° C.):

| Target | Concentration | Matrix |
| --- | --- | --- |
| HBV | 50 IU/ml | K3 EDTA plasma |
| HIV-1M | 100 cp/ml | K3 EDTA plasma |
| CT | 2.5 fg/ml | PreservCyt |

Each respective sample (500 ul) and each respective specimen diluent (350 ul) were pipetted manually into a deepwell plate, wherein each sample was added to three different wells for triplicate analysis. To each well containing an HIV or HBV sample, 50 ul of an internal control nucleic acid were manually added. For the qualitative HIV assay, an RNA serving as a qualitative control was added (100 armored particles/sample). For the quantitative HIV assay, an RNA serving as a quantitative standard was added (500 armored particles/sample). For the quantitative HBV assay, a DNA serving as a quantitative standard was added (1E4 copies/sample). The sequence of said control nucleic acids was identical in all cases and selected from the group of SEQ ID NOs 45-48.

The respective control nucleic acid was stored in the following buffer:

| IC/IQS - Storage Buffer | Conc. or pH |
| --- | --- |
| Tris (mM) | 10 |
| EDTA (mM) | 0.1 |
| Sodium Azide (w/v, %) | 0.05 |
| Poly rA RNA (mg/l) | 20 |
| pH | 8 |

Figure 1:
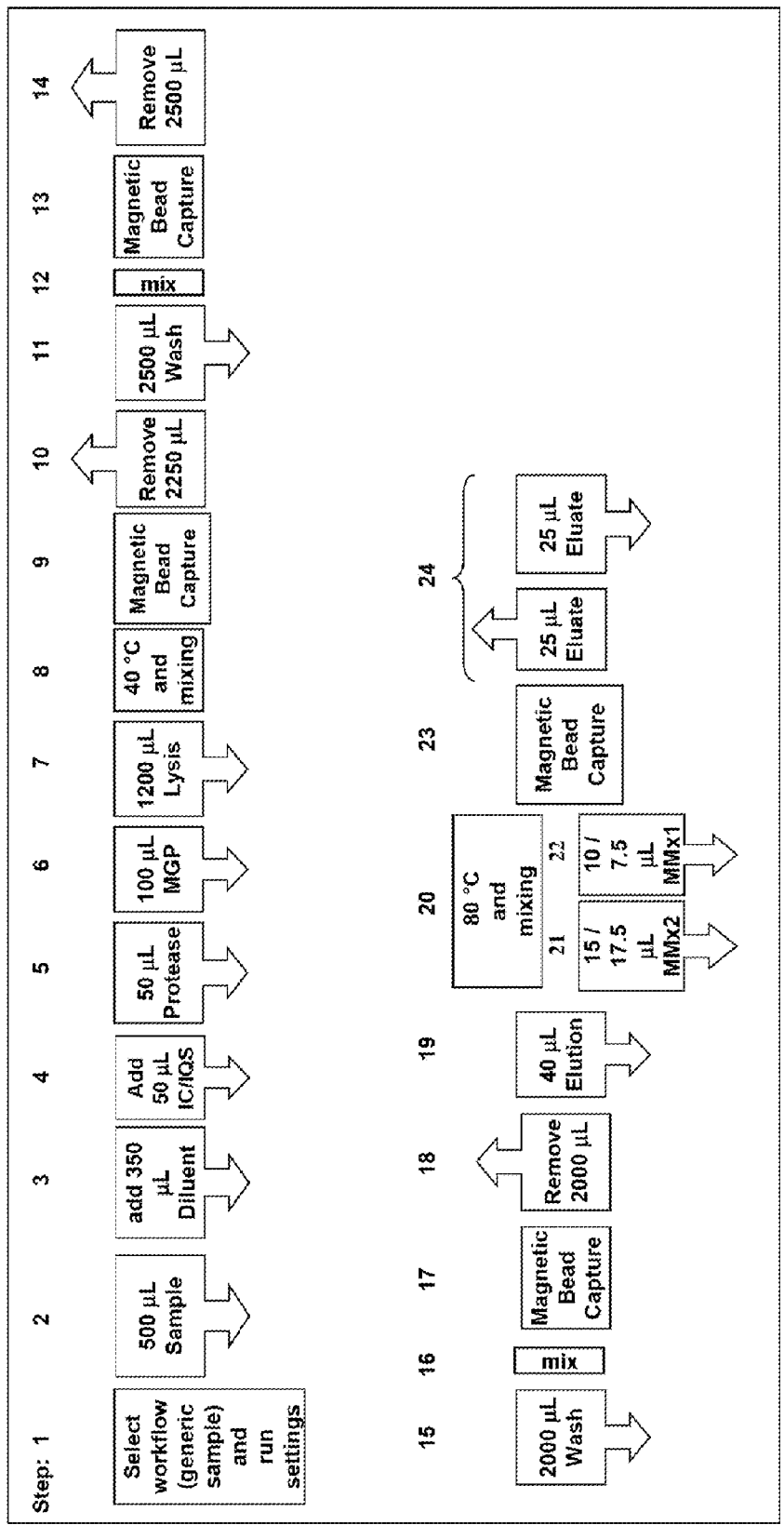
FIG. 1: Schematic depiction of the sample preparation workflow as used in an embodiment of the invention.

Sample preparation was performed on a Hamilton Star (Hamilton, Bonaduz, CH), following the workflow according to the scheme depicted in FIG. 1 and using the following reagents:

| Protease reagent | Conc. or pH |
| --- | --- |
| Tris (mM) | 10 |
| EDTA (mM) | 1 |
| Calcium Chloride (mM) | 5 |
| Calcium Acetate (mM) | 5 |
| Esperase (mg/ml) | 80 |
| Glycerin (w/v, %) | 50 |
| pH | 5.5 |

| MGP Reagent | Conc. or pH |
| --- | --- |
| MPG Powder (mg/ml) | 60 |
| Tris (mM) | 30 |
| Methylparaben (w/v, %) | 0.1 |
| Sodium Azide (w/v, %) | 0.095 |
| pH | 8.5 |

| Lysis Reagent | Conc. or pH |
| --- | --- |
| Guanidine Thiocyanate (M) | 4 |
| Sodium Citrate (mM) | 50 |
| Polydocanol (w/v, %) | 5 |
| Dithiotreitol (w/v, %) | 2 |
| pH | 5.8 |

| Wash buffer | Conc. or pH |
| --- | --- |
| Sodium Citrate (mM) | 7.5 |
| Methylparaben (w/v, %) | 0.1 |
| pH | 4.1 |

| Elution buffer | Conc. or pH |
|---|---|
| Tris (mM) | 30 |
| Methylparaben (w/v, %) | 0.2 |
| pH | 8.5 |

After the final step, the process head of the Hamilton Star apparatus added the respective mastermixes (Mmxs) containing amplification reagents to each well, mixed the fluids containing the isolated nucleic acids with the Mmx and transferred each resulting mixture to a corresponding well of a microwell plate in which the amplification was carried out.

The following mastermixes (each consisting of the two reagents R1 and R2) were used:

For HIV:

| | Concentration/50 μl-PCR [μM] |
|---|---|
| R1 Reagent | |
| Water (PCR grade) | |
| Mn(Ac)$_2$ * 4H$_2$O (pH 6.1 adjusted with Acetic Acid) | 3'000 |
| NaN3/Ri, buffered with 10 mM Tris at pH 7 [%] | 0.018 |
| R2 Reagent | |
| DMSO [%] | 5.000% |
| NaN3/Ri, buffered with 10 mM Tris at pH 7 [%] | 0.027% |
| Potassium acetate pH 7.0 | 110'000 |
| Glycerol [%] | 3.000% |
| Tricine pH 8.0 | 50'000 |
| Igepal [%] | 0.024% |
| dGTP | 337.5 |
| dATP | 337.5 |
| dCTP | 337.5 |
| dUTP | 675 |
| Primers/probes selected from SEQ ID NOs 1-35 | 0.1-0.15 |
| SEQ ID NO 42 | 0.1 |
| SEQ ID NO 43 | 0.1 |
| SEQ ID NO 44 | 0.1 |
| Uracil-N-Glycosylase | 10 (U/reaction) |
| Z05-D Polymerase | 40 (U/reactionn) |
| NTQ21-46A - Aptamer | 0.222 |
| Water | |

For HBV:

| | Concentration/50 μl-PCR | |
|---|---|---|
| R2 Reagent | | |
| H20 | 100 | % |
| Tricine 7.7 | 40 | mM |
| Tween | 0.03 | % (v/v) |
| Glycerol | 5 | % (v/v) |
| KOH | 25.2 | mM |
| KOAc | 121.8 | mM |
| NTQ21-46A (Aptamer) | 0.2625 | uM |
| dGTP | 0.42 | uM |
| dATP | 0.42 | uM |
| dCTP | 0.42 | uM |
| dUTP | 0.84 | uM |
| SEQ ID NO 36 | 1.2 | uM |
| SEQ ID NO 37 | 0.1 | uM |
| SEQ ID NO 38 | 1.2 | uM |
| SEQ ID NO 42 | 0.6 | uM |
| SEQ ID NO 43 | 0.6 | uM |
| SEQ ID NO 44 | 0.15 | uM |
| Z05D Polymerase | 35 | (U/reaction) |
| Uracil-N-Glycosylase | 2 | (U/reaction) |
| Sodium Azide | 0.027 | % (m/v) |
| R1 Reagent | | |
| H20 | 100 | % |
| MgOAc | 2.5 | mM |
| MnOAc pH 6.1 | 2.5 | mM |
| Sodium Azide | 0.018 | % (m/v) |

For CT:

| | Concentration/50 μl-PCR | |
|---|---|---|
| R1 Reagent | | |
| Water (PCR grade) | | |
| Mn(Ac)$_2$ (pH 6.5 in 0.002% (V/V) Glacial Acetic Acid) | 2.7 | mM |
| NaN3 | 0.0135% | (W/V) |
| R2 Reagent | | |
| NaN3/Ri, buffered with 10 mM Tris at pH 7 [%] | 0.0315% | |
| Potassium acetate | 112.4 | mM |
| Glycerol [%] | 3.5% | |
| Tricine | 61 | mM |
| Potassium hydroxide | 28.4 | mM |
| dGTP | 525 | uM |
| dATP | 525 | uM |
| dCTP | 525 | uM |
| dUTP | 1.05 | mM |
| SEQ ID NO 39 | 750 | nM |
| SEQ ID NO 40 | 600 | nM |
| SEQ ID NO 41 | 116 | nM |
| Aptamer NTQ-46A | 175 | nM |
| Uracil-N-Glycosylase | 5 | U/reaction |
| Z05-D Polymerase | 31 | U/reaction |

For amplification and detection, the microwell plate was sealed with an automated plate sealer (see above), and the plate was transferred to a LightCycler 480 (see above).

The following PCR profile was used:

| Thermo cycling profile | | | | | | |
|---|---|---|---|---|---|---|
| Program Name | Target (° C.) | Acquisition Mode | Hold (hh:mm:ss) | Ramp Rate (° C./s) | Cycles | Analysis Mode |
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd | 91 | None | 00:00:05 | 4.4 | 45 | Quantification |

-continued

Thermo cycling profile

| Program Name | Target (° C.) | Acquisition Mode | Hold (hh:mm:ss) | Ramp Rate (° C./s) | Cycles | Analysis Mode |
|---|---|---|---|---|---|---|
| Measurement | 58 | Single | 00:00:25 | 2.2 | | |
| Cooling | 40 | None | 00:02:00 | 2.2 | 1 | None |

Detection Format (Manual)

| Filter Combination | Integration Time (sec) |
|---|---|
| 435-470 | 1 |
| 495-525 | 0.5 |
| 540-580 | 0.5 |
| 610-645 | 0.5 |
| 680-700 | 1 |

The Pre-PCR program comprises initial denaturing and incubation at 55, 60 and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription.

PCR cycling is divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Using this profile on all samples comprised on the microwell plate mentioned above, amplification and detection was achieved in all samples, as depicted in FIG. 2. This shows that the sample preparation prior to amplification was also successfully carried out.

The results for the qualitative and quantitative HIV internal controls and the quantitative HBV internal control are depicted separately in FIG. 2 for the sake of clarity. It can be seen that the controls were also successfully amplified in all cases. The quantitation of the HIV and HBV targets in the quantitative setup were calculated by comparison with the internal control nucleic acid serving as a quantitative standard.

Example 2

The generic amplification process described hereinabove was carried out on a variety of different target nucleic acids in separate experiments but under identical conditions. Isolation of the respective nucleic acid was carried out as described under Example 1.

The respective generic internal control nucleic acid was selected from SEQ ID NOs 45-49 and was armored RNA for RNA targets and lambda-packaged DNA for DNA targets. For qualitative RNA assays, 300 particles were added per sample, for quantitative RNA assays 3000 and for all DNA assays 500.

The following PCR profile was used on all targets:

| | Target [° C.] | Acquisition Mode | Plateau [hh:mm:ss] | Measure [hh:mm:ss] | Ramp Rate [° C./s] |
|---|---|---|---|---|---|
| Pre-PCR | UNG-Step | 50 | none | 00:02:00 | 00:00:00 | 2.2 |
| | UNG/Template Denaturation | 94 | none | 00:00:05 | 00:00:00 | 4.4 |
| | RT-Step | 55 | none | 00:02:00 | 00:00:00 | 2.2 |
| | | 60 | none | 00:06:00 | 00:00:00 | 4.4 |
| | | 65 | none | 00:04:00 | 00:00:00 | 4.4 |
| 1st Measurement | | 95 | none | 00:00:05 | 00:00:00 | 4.4 |
| | | 55 | single | 00:00:30 | 00:00:08 | 2.2 |
| 2nd Measurement | | 91 | none | 00:00:05 | 00:00:00 | 4.4 |
| | | 58 | single | 00:00:25 | 00:00:08 | 2.2 |
| Cooling | | 40 | none | 00:02:00 | 00:00:00 | 2.2 |

| Name | Cycles |
|---|---|
| Pre-PCR | 1 |
| 1st Measurement | 5 |
| 2nd Measurement | 45 |
| Cooling | 1 |

In detail, the following experiments were performed:
1. Qualitative multiplex analysis of HBV, HCV and HIV
a. Mastermix
R1:

| | Conc. in 50 ul-PCR (uM) |
|---|---|
| Mn(Ac)2 * 4H2O (pH 6.1 adjusted with Acetic Acid) | 3'300 |
| NaN3/Ri, buffered with 10 mM Tris at pH 7 | 0.018 |
| | pH: 6.41 |

R2:

| Reagent | Conc. in 50 ul-PCR (uM) |
|---|---|
| DMSO (%) | 5.4 |
| NaN3/Ri, buffered with 10 mM Tris at pH 7 | 0.027 |
| KOAc (pH 7.0) | 120'000 |
| Glycerol (%) | 3 |
| Tween 20 (%) | 0.015 |
| Tricine pH 8.0 | 60'000 |
| NTQ21-46A - Aptamer | 0.2222 |
| Uracil-N-Glycosylase (U/uL) | 0.2 |
| dGTP | 400.0 |
| dATP | 400.0 |
| dCTP | 400.0 |
| dUTP | 800.0 |
| ZO5-D Polymerase (U/ul)* | 0.9 |
| Primers/probes selected from SEQ ID NOs 1-35 | 0.125-0.3 |
| SEQ ID NO 36 | 0.100 |
| SEQ ID NO 37 | 0.100 |
| SEQ ID NO 38 | 0.150 |
| Primers/probes selected from SEQ ID NOs 60-76 | 0.050-0.250 |
| SEQ ID NO 42 | 0.200 |

-continued

| Reagent | Conc. in 50 ul-PCR (uM) |
|---|---|
| SEQ ID NO 43 | 0.200 |
| SEQ ID NO 44 | 0.100 |

Analytical Sensitivity/LOD

For each detected virus (HIV-1 group M, HIV-1 group O, HIV-2, HBV and HCV), at several concentrations/levels at and around the anticipated LOD for EDTA-plasma. One panel per virus and concentration was tested with at least 20 valid replicates per concentration. The LOD was determined by PROBIT analysis (see Table 1-5).

HIV

TABLE 1

HIV-1 Group M Hit rates and Probit LOD from individual panel

| Concentration | Number of replicates | Number of positives | Hit rate |
|---|---|---|---|
| 32 cp/mL | 21 | 21 | 100% |
| 16 cp/mL | 21 | 21 | 100% |
| 8 cp/mL | 21 | 21 | 100% |
| 4 cp/mL | 21 | 20 | 95% |
| 2 cp/mL | 21 | 15 | 71% |
| 1 cp/mL | 21 | 9 | 43% |
| 0 cp/mL (neg. control) | 12 | 0 | 0% |
| LOD by PROBIT analysis (95% hitrate) | | | 4.06 cp/mL |
| 95% confidence interval for LOD by PROBIT analysis | | | 2.85-9.24 cp/mL |

Titer of WHO Standard for HIV-1 Group M was converted to IU/mL.

$$\text{Titer}\left(\text{in}\frac{IU}{mL}\right) = \frac{\text{Titer}\left(\text{in}\frac{cp}{mL}\right)}{0.6}$$

Therefore HIV-1 Group M LOD in IU/mL is
LOD by PROBIT analysis (95% hitrate): 6.77 IU/mL
95% confidence interval for LOD by PROBIT analysis: 4.75-15.4 IU/mL

TABLE 2

HIV-1 Group O Hit rates and Probit LOD from individual panel

| Concentration | Number of replicates | Number of positives | Hit rate |
|---|---|---|---|
| 60 cp/mL | 21 | 21 | 100% |
| 30 cp/mL | 20 | 20 | 100% |
| 20 cp/mL | 21 | 21 | 100% |
| 14 cp/mL | 21 | 19 | 90% |
| 7 cp/mL | 21 | 15 | 71% |
| 4.5 cp/mL | 21 | 12 | 57% |
| 0 cp/mL (neg. control) | 12 | 0 | 0% |
| LOD by PROBIT analysis (95% hitrate) | | | 14.9 cp/mL |
| 95% confidence interval for LOD by PROBIT analysis | | | 10.9-31.5 cp/mL |

Titer of Primary Standard for HIV-1 Group O was reassigned to CBER HIV-1 Group 0 panel; calculation factor is 0.586.

Therefore HIV-1 Group O LOD is
LOD by PROBIT analysis (95% hitrate): 8.8 cp/mL
95% confidence interval for LOD by PROBIT analysis: 6.4-18.5 cp/mL

TABLE 3

HIV-2 Hit rates and Probit LOD from individual panel

| Concentration | Number of replicates | Number of positives | Hit rate |
|---|---|---|---|
| 4 cp/mL | 21 | 21 | 100% |
| 2 cp/mL | 21 | 21 | 100% |
| 1 cp/mL | 21 | 20 | 95% |
| 0.5 cp/mL | 21 | 13 | 62% |
| 0.25 cp/mL | 21 | 13 | 62% |
| 0.125 cp/mL | 21 | 7 | 33% |
| 0 cp/mL (neg. control) | 12 | 0 | 0% |
| LOD by PROBIT analysis (95% hitrate) | | | 1.29 cp/mL |
| 95% confidence interval for LOD by PROBIT analysis | | | -3.11 cp/mL |

Titer of Primary Standard for HIV-2 was reassigned to CBER HIV-2 panel; calculation factor is 26.7.

Therefore HIV-2 LOD is
LOD by PROBIT analysis (95% hitrate): 34.44 cp/mL
95% confidence interval for LOD by PROBIT analysis: 21.89-83.04 cp/mL

HBV

TABLE 4

HBV Hit rates and Probit LOD from individual panel

| Concentration | Number of replicates | Number of positives | Hit rate |
|---|---|---|---|
| 7.6 IU/mL | 21 | 21 | 100% |
| 3.8 IU/mL | 21 | 21 | 100% |
| 1.9 IU/mL | 21 | 20 | 95% |
| 0.95 IU/mL | 21 | 14 | 67% |
| 0.6 IU/mL | 19 | 12 | 63% |
| 0.4 IU/mL | 21 | 12 | 57% |
| 0 IU/mL (neg. control) | 12 | 0 | 0% |
| LOD by PROBIT analysis (95% hitrate) | | | 2.27 IU/mL |
| 95% confidence interval for LOD by PROBIT analysis | | | 1.48-6.54 IU/mL |

HCV

TABLE 5

HCV Hit rates and Probit LOD from individual panel

| Concentration | Number of replicates | Number of positives | Hit rate |
|---|---|---|---|
| 24 IU/mL | 21 | 21 | 100% |
| 12 IU/mL | 21 | 21 | 100% |
| 6 IU/mL | 21 | 21 | 100% |
| 3 IU/mL | 21 | 17 | 81% |
| 1.5 IU/mL | 21 | 14 | 67% |
| 0.75 IU/mL | 21 | 9 | 43% |
| 0 IU/mL (neg. control) | 18 | 0 | 0% |
| LOD by PROBIT analysis (95% hitrate) | | | 4.76 IU/mL |
| 95% confidence interval for LOD by PROBIT analysis | | | 3.14-11.61 IU/mL |

2. Qualitative Analysis of WNV

Mastermix
R1:

| Reagent | Conc. in 50 ul-PCR (uM) |
|---|---|
| Mn(Ac)2 * 4H2O (pH 6.1 adjusted with Acetic Acid) | 3'300 |
| NaN3/Ri, buffered with 10 mM Tris at pH 7 | 0.018 |
| | pH: 6.41 |

R2:

| Reagent | Conc. in 50 ul-PCR (uM) |
|---|---|
| DMSO (%) | 5.4 |
| NaN3/Ri, buffered with 10 mM Tris at pH 7 | 0.027 |
| K acetate pH 7.0 | 120'000 |
| Glycerol (%) | 3 |
| Tween 20 (%) | 0.015 |
| Tricine pH 8.0 | 60'000 |
| NTQ21-46A - Aptamer | 0.2222 |
| Uracil-N-Glycosylase (U/uL) | 0.2 |
| dGTP | 400.0 |
| dATP | 400.0 |
| dCTP | 400.0 |
| dUTP | 800.0 |
| ZO5-D Polymerase (U/ul)* | 0.9 |
| Primers/probes selected from SEQ ID NOs 53-59 | 0.08-0.4 |
| SEQ ID NO 42 | 0.150 |
| SEQ ID NO 43 | 0.150 |
| SEQ ID NO 44 | 0.100 |

Analytical Sensitivity/LOD

For the viruses (WNV, SLEV and JEV) an independent panel was prepared as a dilution series of the respective Standard including several concentrations/levels at and around the anticipated LOD. One panel per virus and concentration was tested with at least 20 valid replicates per concentration. The LOD was determined by PROBIT analysis.

TABLE 6

WNV Hit rates and Probit LOD from individual panel

| Concentration | Number of replicates | Number of positives | Hit rate |
|---|---|---|---|
| 20 cp/mL | 21 | 21 | 100% |
| 12 cp/mL | 21 | 21 | 100% |
| 8 cp/mL | 21 | 21 | 100% |
| 5 cp/mL | 21 | 17 | 81% |
| 2.5 cp/mL | 21 | 15 | 71.4% |
| 0.5 cp/mL | 21 | 1 | 4.8% |
| 0 cp/mL (neg. control) | 12 | 0 | 0% |
| LOD by PROBIT analysis (95% hitrate) | | | 6.57 cp/mL |
| 95% confidence interval for LOD by PROBIT analysis | | | 4.74-11.03 cp/mL |

TABLE 7

SLEV Hit rates and Probit LOD from individual panel

| Concentration | Number of replicates | Number of positives | Hit rate |
|---|---|---|---|
| 140 cp/mL | 21 | 21 | 100% |
| 100 cp/mL | 21 | 20 | 95.2% |
| 70 cp/mL | 21 | 20 | 95.2% |
| 40 cp/mL | 21 | 17 | 81.0% |
| 20 cp/mL | 21 | 11 | 52.4% |
| 10 cp/mL | 21 | 6 | 28.6% |
| 0 cp/mL (neg. control) | 12 | 0 | 0% |
| LOD by PROBIT analysis (95% hitrate) | | | 78.9 cp/mL |
| 95% confidence interval for LOD by PROBIT analysis | | | 55.4-145.7 cp/mL |

TABLE 8

JEV Hit rates and Probit LOD from individual panel

| Concentration | Number of replicates | Number of positives | Hit rate |
|---|---|---|---|
| 20 cp/mL | 21 | 20 | 95.2% |
| 12 cp/mL | 21 | 20 | 95.2% |
| 8 cp/mL | 21 | 18 | 85.7% |
| 5 cp/mL | 21 | 17 | 81.0% |
| 2.5 cp/mL | 21 | 14 | 66.7% |
| 0.5 cp/mL | 21 | 2 | 9.52% |
| 0 cp/mL (neg. control) | 12 | 0 | 0% |
| LOD by PROBIT analysis (95% hitrate) | | | 13.55 cp/mL |
| 95% confidence interval for LOD by PROBIT analysis | | | 8.78-27.7 cp/mL |

3. Quantitative Analysis of HBV Mastermix

R1:

| Reagent | Final Conc. in 50 ul-PCR (uM) |
|---|---|
| Mn(Ac)2 * 4H2O (pH 6.1 adjusted with Acetic Acid) | 3'300 |
| NaN3/Ri, buffered with 10 mM Tris at pH 7 | 0.018 |
| | pH: 6.41 |

R2:

| Reagent | Final Conc. in 50 ul-PCR (uM) |
|---|---|
| Glycerol (%, w/v) | 3% |
| Tricine | 60 mM |
| DMSO (%, v/v) | 5.4% |
| KOAc | 120 mM |
| Tween 20 (v/v) | 0.015% |
| Aptamer NTQ21-46 A | 0.222 µM |
| ZO5D Polymerase | 0.9 U/µL (45 U/rxn) |
| Uracil-N-Glycosylase | 0.2 U/µL (10 U/rxn) |
| Sodium Azide (w/v) | 0.027% |
| dCTPs | 400 µM |
| dGTPs | 400 µM |
| dATPs | 400 µM |
| dUTPs | 800 µM |
| SEQ ID NO 36 | 1.2 µM |
| SEQ ID NO 37 | 1.2 µM |
| SEQ ID NO 50 | 0.6 µM |
| SEQ ID NO 51 | 0.6 µM |
| SEQ ID NO 38 | 0.1 µM |
| SEQ ID NO 52 | M |

Analytical Sensitivity/LOD

Four dilution panels were prepared with HBV Secondary Standard (representing Genotype A), i.e., two in HBV negative serum for sample input volumes of 200 µL and 500 µL, and two in HBV negative EDTA-plasma for sample input volumes of 200 µL and 500 µL. Each panel included 7 concentration levels at and around the anticipated LOD. One panel per matrix was tested with ≥21 replicates per concentration level. At least 20 replicates needed to be valid. The LOD was determined by PROBIT analysis at 95% hit rate and by ≥95% hit rate analysis.

TABLE 9

LOD analysis for 200 μL input volume in EDTA-plasma. *

| Concentration | Number of replicates | Number of positives | Hit rate |
| --- | --- | --- | --- |
| 25 IU/mL | 41 | 41 | 100% |
| 15 IU/mL | 41 | 39 | 95.1% |
| 10 IU/mL | 41 | 40 | 97.6% |
| 7 IU/mL | 41 | 40 | 97.6% |
| 4 IU/mL | 24 | 20 | 83.3% |
| 1 IU/mL | 24 | 4 | 16.7% |
| 0 IU/mL (neg. control) | 24 | 0 | 0% |
| LOD by PROBIT analysis (95% hitrate) | | | 8.2 IU/mL |
| 95% confidence interval for LOD by PROBIT analysis | | | 4.8-26.0 IU/mL |

* Additional replicates were tested to narrow the observed 95% confidence interval.

TABLE 10

LOD analysis for 500 μL input volume in EDTA-plasma.

| Concentration | Number of replicates | Number of positives | Hit rate |
| --- | --- | --- | --- |
| 10 IU/mL | 21 | 21 | 100% |
| 7 IU/mL | 21 | 21 | 100% |
| 4 IU/mL | 21 | 21 | 100% |
| 2.5 IU/mL | 21 | 20 | 95.2% |
| 1 IU/mL | 21 | 14 | 66.7% |
| 0.2 IU/mL | 21 | 1 | 4.8% |
| 0 IU/mL (neg. control) | 21 | 0 | 0% |
| LOD by PROBIT analysis (95% hitrate) | | | 2.3 IU/mL |
| 95% confidence interval for LOD by PROBIT analysis | | | 1.6-4.2 IU/mL |

TABLE 11

LOD analysis for 200 μL input volume in serum.

| Concentration | Number of replicates | Number of positives | Hit rate |
| --- | --- | --- | --- |
| 25 IU/mL | 21 | 21 | 100% |
| 15 IU/mL | 21 | 20 | 95.2% |
| 10 IU/mL | 21 | 21 | 100% |
| 7 IU/mL | 21 | 20 | 95.2% |
| 4 IU/mL | 21 | 15 | 71.4% |
| 1 IU/mL | 21 | 8 | 38.1% |
| 0 IU/mL (neg. control) | 21 | 0 | 0% |
| LOD by PROBIT analysis (95% hitrate) | | | 9.4 IU/mL |
| 95% confidence interval for LOD by PROBIT analysis | | | 6.2-19.0 IU/mL |

TABLE 12

LOD analysis for 500 μL input volume in serum.

| Concentration | Number of replicates | Number of positives | Hit rate |
| --- | --- | --- | --- |
| 10 IU/mL | 21 | 21 | 100% |
| 7 IU/mL | 21 | 21 | 100% |
| 4 IU/mL | 21 | 21 | 100% |
| 2.5 IU/mL | 21 | 16 | 76.2% |
| 1 IU/mL | 21 | 16 | 76.2% |
| 0.2 IU/mL | 21 | 7 | 33.3% |
| 0 IU/mL (neg. control) | 21 | 0 | 0% |
| LOD by PROBIT analysis (95% hitrate) | | | 4.1 IU/mL |
| 95% confidence interval for LOD by PROBIT analysis | | | 2.4-10.0 IU/mL |

Summary LOD:

EDTA-plasma: The PROBIT analysis at 95% hit rate resulted in an LOD of 8.2 IU/mL for 200 μL sample input volume and 2.3 IU/mL for 500 μL sample input volume for EDTA-plasma.

The 95% confidence interval range for these concentrations was 4.8-26.0 IU/mL for 200 μl sample input volume and 1.6-4.2 IU/mL for 500 μL sample input volume.

Serum: The PROBIT analysis at 95% hit rate resulted in an LOD of 9.02 IU/mL for 200 μL sample input volume and 4.1 IU/mL for 500 μL sample input volume for serum.

The 95% confidence interval range for these concentrations was 6.2-19.0 IU/mL for 200 μL sample input volume and 2.4-10.0 IU/mL for 500 μL sample input volume.

Linearity

One EDTA-plasma panel and one serum panel were prepared by using HBV genotype A (provided by RMD Research Pleasanton, linearized plasmid, pHBV-PC_ADW2). Each of the panels was analyzed at 12 concentration levels for the determination of the expected dynamic range (4–2E+09 IU/mL) of the assay. All concentration levels/panel members (PM) were tested in 21 replicates.

This study was done with a sample input volume of 500 μL. The concentration levels were selected as follows: One level below expected Lower Limit of Quantitation (LLOQ), one at expected LLOQ, one above expected LLOQ, several concentrations at intermediates levels, at expected Upper Limit of Quantitation (ULOQ) and one above expected ULOQ:

PM 12—2.0E+09 IU/mL—above expected ULOQ
PM 11—1.0E+09 IU/mL—at expected ULOQ
PM 10—1.0E+08 IU/mL—below expected ULOQ
PM 9—1.0E+07 IU/mL—intermediate concentration level
PM 8—1.0E+06 IU/mL—intermediate concentration level
PM 7—1.0E+05 IU/mL—intermediate concentration level
PM 6—1.0E+04 IU/mL—intermediate concentration level
PM 5—1.0E+03 IU/mL—intermediate concentration level
PM 6a—2.0E+02 IU/mL—intermediate concentration level (PM 6 diluted to 2.0E+02 IU/mL, used for titer assignment of serum panel)
PM 4—1.0E+02 IU/mL—intermediate concentration level (also used for titer assignment of plasma panel)
PM 3—5.0E+01 IU/mL—above expected LLOQ
PM 2—1.0E+01 IU/mL—at expected LLOQ
PM 1—4.0E+00 IU/mL below expected LLOQ For every valid sample of the linearity panel, the observed HBV DNA titer was transformed to log 10 titer and the mean log 10 titer was calculated per concentration level.

TABLE 13

Linearity in EDTA Plasma

| Nominal Titer (IU/mL) | Assigned Titer (IU/mL) | Assigned Log10 Titer | Mean Log 10 Titer observed | Replicates |
| --- | --- | --- | --- | --- |
| 4.00E+00 | 3.50E+00 | 0.54 | 0.52 | 17 |
| 1.00E+01 | 8.70E+00 | 0.94 | 0.91 | 21 |
| 5.00E+01 | 4.40E+01 | 1.64 | 1.69 | 21 |
| 1.00E+02 | 8.70E+01 | 1.94 | 2.04 | 21 |
| 1.00E+03 | 8.70E+02 | 2.94 | 3.01 | 21 |
| 1.00E+04 | 8.70E+03 | 3.94 | 3.9 | 21 |
| 1.00E+05 | 8.70E+04 | 4.94 | 4.88 | 21 |
| 1.00E+06 | 8.70E+05 | 5.94 | 5.87 | 21 |
| 1.00E+07 | 8.70E+06 | 6.94 | 6.92 | 21 |
| 1.00E+08 | 8.70E+07 | 7.94 | 8.01 | 21 |
| 1.00E+09 | 8.70E+08 | 8.94 | 9.04 | 21 |
| 2.00E+09 | 1.70E+09 | 9.24 | 9.38 | 21 |

A graphical depiction of this result is shown in FIG. 13.

TABLE 14

Linearity in Serum

| Nominal Titer (IU/mL) | Assigned Titer (IU/mL) | Assigned Log10 Titer | Mean Log 10 Titer observed | Replicates |
|---|---|---|---|---|
| 4.00E+00 | 3.30E+00 | 0.52 | 0.7 | 21 |
| 1.00E+01 | 8.30E+00 | 0.92 | 0.99 | 21 |
| 5.00E+01 | 4.10E+01 | 1.62 | 1.73 | 21 |
| 1.00E+02 | 8.30E+01 | 1.92 | 2.03 | 21 |
| 1.00E+03 | 8.30E+02 | 2.92 | 2.93 | 21 |
| 1.00E+04 | 8.30E+03 | 3.92 | 3.8 | 21 |
| 1.00E+05 | 8.30E+04 | 4.92 | 4.78 | 21 |
| 1.00E+06 | 8.30E+05 | 5.92 | 5.75 | 21 |
| 1.00E+07 | 8.30E+06 | 6.92 | 6.73 | 21 |
| 1.00E+08 | 8.30E+07 | 7.92 | 7.78 | 21 |
| 1.00E+09 | 8.30E+08 | 8.92 | 8.92 | 21 |
| 2.00E+09 | 1.70E+09 | 9.22 | 9.22 | 21 |

A graphical depiction of this result is shown in FIG. 14.

Summary Linearity:

The linear range, defined as the concentration range for which the log 10 deviation of the mean log 10 observed titers is within ±0.3 of the log 10 nominal titer was determined as: 3.5E+00 IU/mL-1.7E+09 IU/mL for EDTA-plasma and 3.3E+00 IU/mL-1.7E+09 IU/mL for serum. The Lower Limit of Quantitation was found to be: 4.0E+00 IU/mL for EDTA-plasma and serum.

4. Quantitative Analysis of HCV

Mastermix

R1:

| Reagent | Final Conc. in 50 ul-PCR (uM) |
|---|---|
| Mn(Ac)2 * 4H2O (pH 6.1 adjusted with Acetic Acid) | 3'300 |
| NaN3/Ri, buffered with 10 mM Tris at pH 7 | 0.018 |
| | pH: 6.41 |

R2:

| Reagent | Final Conc. in 50 ul-PCR |
|---|---|
| Glycerol (%, w/v) | 3% |
| Tricine | 60 mM |
| DMSO (%, v/v) | 5.4% |
| KOAc | 120 mM |
| Tween 20 (v/v) | 0.015% |
| NTQ21-46 A | 0.222 µM |
| Z05D | 0.9 U/µL (45 U/rxn) |
| UNG | 0.2 U/µL (10 U/rxn) |
| Sodium Azide (w/v) | 0.027 |
| dCTPs | 400 µM |
| dGTPs | 400 µM |
| dATPs | 400 µM |
| dUTPs | 800 µM |
| Primers/probes selected from SEQ ID NOs 60-76 | 0.1 µM |
| SEQ ID NO 42 | 0.3 µM |
| SEQ ID NO 43 | 0.3 µM |
| SEQ ID NO 44 | µM |

Analytical Sensitivity/LOD

A dilution panel was prepared with Roche HCV Secondary Standard in HCV negative EDTA plasma and serum using a sample input volumes of 200 µl and 500 µL. Each concentration level was tested with 21 replicates. At least ≥20 replicates have to be valid. The LOD was determined by PROBIT analysis at 95% hit rate and by ≥95% hit rate analysis.

TABLE 15

Hit rates and Probit with 200 µL sample process input volume for EDTA-plasma

| Concentration | Number of replicates | Number of positives | Hit rate |
|---|---|---|---|
| 55 IU/mL | 21 | 21 | 100% |
| 38 IU/mL | 21 | 21 | 100% |
| 25 IU/mL | 21 | 20 | 95% |
| 12.5 IU/mL | 21 | 19 | 90% |
| 6 IU/mL | 21 | 15 | 71% |
| 3 IU/mL | 21 | 6 | 29% |
| 0 IU/mL (neg. control) | 21 | 0 | 0% |
| LOD by PROBIT analysis (95% hitrate) | | | 17.4 IU/mL |
| 95% confidence interval for LOD by PROBIT analysis | | | 12.1-34.3 IU/mL |

TABLE 16

Hit rates and Probit with 500 µL sample process input volume for EDTA-plasma

| Concentration | Number of replicates | Number of positives | Hit rate |
|---|---|---|---|
| 22 IU/mL | 21 | 21 | 100% |
| 15 IU/mL | 21 | 21 | 100% |
| 10 IU/mL | 20 | 20 | 100% |
| 5 IU/mL | 21 | 19 | 76% |
| 2.5 IU/mL | 21 | 15 | 71% |
| 1 IU/mL | 21 | 6 | 57% |
| 0 IU/mL (neg. control) | 21 | 0 | 0% |
| LOD by PROBIT analysis (95% hitrate) | | | 9.0 IU/mL |
| 95% confidence interval for LOD by PROBIT analysis | | | 5.5-25.4 IU/mL |

TABLE 17

Hit rates and Probit with 200 µL sample process input volume for serum

| Concentration | Number of replicates | Number of positives | Hit rate |
|---|---|---|---|
| 55 IU/mL | 21 | 21 | 100% |
| 38 IU/mL | 21 | 21 | 100% |
| 25 IU/mL | 21 | 20 | 95% |
| 12.5 IU/mL | 21 | 18 | 86% |
| 6 IU/mL | 21 | 13 | 62% |
| 3 IU/mL | 21 | 6 | 29% |
| 0 IU/mL (neg. control) | 21 | 0 | 0% |
| LOD by PROBIT analysis (95% hitrate) | | | 20.2 IU/mL |
| 95% confidence interval for LOD by PROBIT analysis | | | 14.0-39.3 IU/mL |

TABLE 18

Hit rates and Probit with 500 µL sample process input volume for serum

| Concentration | Number of replicates | Number of positives | Hit rate |
|---|---|---|---|
| 22 IU/mL | 21 | 21 | 100% |
| 15 IU/mL | 21 | 21 | 100% |
| 10 IU/mL | 21 | 20 | 95% |
| 5 IU/mL | 21 | 18 | 86% |
| 2.5 IU/mL | 21 | 12 | 57% |
| 1 IU/mL | 21 | 4 | 19% |
| 0 IU/mL (neg. control) | 21 | 0 | 0% |
| LOD by PROBIT analysis (95% hitrate) | | | 8.2 IU/mL |
| 95% confidence interval for LOD by PROBIT analysis | | | 5.8-15.0 IU/mL |

Summary LOD:
1. The PROBIT analysis at 95% Hit rate resulted in an LOD of 17.4 IU/mL for 200 μL sample process input volume and 9.0 IU/mL for 500 μL sample process input volume for EDTA plasma. The 95% confidence interval for these concentrations is 12.1-34.3 IU/mL for 200 μL sample process input volume and 5.5-25.4 IU/mL for 500 μL sample process input volume.
2. The values of the PROBIT analysis at 95% Hit rate is 20.2 IU/mL for 200 μL sample process input volume and 8.2 IU/mL for 500 μsample process input volume for serum. The 95% confidence interval for these concentrations is 14.0-39.3 IU/mL for 200 μL sample process input volume and 5.8-15.0 IU/mL for 500 μL sample process input volume.

Linearity

One preparation of an EDTA-plasma panel and one preparation of a serum panel of HCV aRNA traceable to the HCV WHO Standard were analyzed. The linearity panels were prepared by serial dilution and analyzed at 10 different concentrations. The study was done with 500 μL sample process input volume. The concentrations were selected as follows: One level below expected Lower Limit of Quantification (LLoQ), one at LLoQ, one above LLOQ, several concentrations at intermediates levels, at expected Upper Limit of Quantification (ULoQ) and one at or above ULoQ. For all concentrations 21 replicates were tested.

PM 1—2.0E+08 IU/mL—above expected ULoQ
PM 2—1.0E+08 IU/mL—at expected ULoQ
PM 3—1.0E+07 IU/mL—below expected ULoQ
PM 4—1.0E+06 IU/mL—intermediate concentration level
PM 5 1.0E+05 IU/mL—intermediate concentration level
PM 6—1.0E+04 IU/mL—intermediate concentration level for titer assignment
PM 7—1.0E+03 IU/mL—intermediate concentration level
PM 8—1.0E+02 IU/mL—above expected LLoQ
PM 9—1.0E+01 IU/mL—at expected LLoQ
PM 10—8.0E+00 IU/mL—below expected LLoQ

TABLE 19

Linearity in EDTA Plasma

| Nominal Titer (IU/mL) | Assigned Titer (IU/mL) | Assigned Log10 Titer | Mean Log 10 Titer observed | Replicates |
|---|---|---|---|---|
| 8.00E+00 | 4.87E+00 | 0.7 | 0.6 | 15 |
| 1.00E+01 | 6.09E+00 | 0.8 | 0.8 | 17 |
| 1.00E+02 | 6.09E+01 | 1.8 | 1.7 | 21 |
| 1.00E+03 | 6.09E+02 | 2.8 | 2.8 | 21 |
| 1.00E+04 | 6.09E+03 | 3.8 | 3.8 | 21 |
| 1.00E+05 | 6.09E+04 | 4.8 | 4.7 | 21/20 |
| 1.00E+06 | 6.09E+05 | 5.8 | 5.6 | 21/20 |
| 1.00E+07 | 6.09E+06 | 6.8 | 6.7 | 21 |
| 1.00E+08 | 6.09E+07 | 7.8 | 7.8/7.7 | 21/18 |
| 2.00E+08 | 1.22E+08 | 8.1 | 8 | 21/20 |

A graphical depiction of this result is shown in FIG. 15.

TABLE 20

Linearity in Serum

| Nominal Titer (IU/mL) | Assigned Titer (IU/mL) | Assigned Log10 Titer | Mean Log 10 Titer observed | Replicates |
|---|---|---|---|---|
| 8.00E+00 | 3.90E+00 | 0.6 | 0.7 | 10 |
| 1.00E+01 | 4.96E+00 | 0.7 | 0.7 | 14 |
| 1.00E+02 | 4.96E+01 | 1.7 | 1.6 | 21 |
| 1.00E+03 | 4.96E+02 | 2.7 | 2.8 | 21 |
| 1.00E+04 | 4.96E+03 | 3.7 | 3.7 | 21 |
| 1.00E+05 | 4.96E+04 | 4.7 | 4.7 | 21 |
| 1.00E+06 | 4.96E+05 | 5.7 | 5.7 | 21 |
| 1.00E+07 | 4.96E+06 | 6.7 | 6.7 | 21 |
| 1.00E+08 | 4.96E+07 | 7.7 | 7.7 | 21 |
| 2.00E+08 | 9.92E+07 | 8 | 8.1 | 21 |

A graphical depiction of this result is shown in FIG. 16.

Summary Linearity:

The linear range, defined as the concentration range for which the log 10 deviation of the mean log 10 observed titers is within ±0.3 of the log 10 nominal titer was determined as: 4.87E+00 IU/mL-1.22E+08 IU/mL for EDTA-plasma and 3.90E+00 IU/mL-9.92E+07 IU/mL for serum.

5. Quantitative Analysis of HIV

Mastermix

R1:

| Reagent | Final Conc. in 50 ul-PCR (uM) |
|---|---|
| Mn(Ac)2 * 4H2O (pH 6.1 adjusted with Acetic Acid) | 3'300 |
| NaN3/Ri, buffered with 10 mM Tris at pH 7 | 0.018 |
| | pH: 6.41 |

R2:

| Reagent | Final Conc. in 50 ul-PCR |
|---|---|
| Glycerol (%, w/v) | 3% |
| Tricine | 60 mM |
| DMSO (%, v/v) | 5.4% |
| KOAc | 120 mM |
| Tween 20 (v/v) | 0.02% |
| Aptamer NTQ21-46 A | 0.222 μM |
| ZO5D Polymerase | 0.9 U/μL (45 U/rxn) |
| UNG | 0.2 U/μL(10 U/rxn) |
| Sodium Azide (w/v) | 0.027 |
| dCTPs | 400 μM |
| dGTPs | 400 μM |
| dATPs | 400 μM |
| dUTPs | 800 μM |
| Primers/probes selected from SEQ ID NOs 1-35 | 0.1 μM-0.3 μM |
| SEQ ID NO 50 | 0.3 μM |
| SEQ ID NO 51 | 0.3 μM |
| SEQ ID NO 52 | μM |

Analytical Sensitivity/LOD

A dilution panel was prepared with HIV-1M Secondary Standard in HIV-1 negative EDTA plasma for sample input volumes of 200 μL and 500 μL. Each concentration level was tested with 21 replicates. At least ≥20 replicates have to be valid. The LOD was determined by PROBIT analysis at 95% hit rate and by ≥95% hit rate analysis.

TABLE 21

LOD analysis for 200 μL input volume in EDTA-plasma

| Concentration | Number of replicates | Number of positives | Hit rate |
|---|---|---|---|
| 200 cp/mL | 21 | 21 | 100% |
| 100 cp/mL | 21 | 21 | 100% |
| 80 cp/mL | 21 | 21 | 100% |
| 50 cp/mL | 21 | 20 | 95.2% |
| 30 cp/mL | 21 | 18 | 85.7% |
| 20 cp/mL | 21 | 17 | 81.0% |
| 10 cp/mL | 21 | 8 | 38.1% |
| 0 cp/mL (neg. control) | 21 | 0 | 0% |
| LOD by PROBIT analysis (95% hitrate) | | | 41.8 cp/mL |
| 95% confidence interval for LOD by PROBIT analysis | | | 30.9-74.9 cp/mL |

TABLE 22

LOD analysis for 500 μL input volume

| Concentration | Number of replicates | Number of positives | Hit rate |
|---|---|---|---|
| 30 cp/mL | 21 | 21 | 100% |
| 25 cp/mL | 21 | 20 | 95.2% |
| 20 cp/mL | 21 | 21 | 100% |
| 13.5 cp/mL | 21 | 18 | 85.7% |
| 9 cp/mL | 21 | 13 | 61.9% |
| 6 cp/mL | 21 | 9 | 42.9% |
| 0 cp/mL (neg. control) | 21 | 0 | 0% |
| LOD by PROBIT analysis (95% hitrate) | | | 18.9 cp/mL |
| 95% confidence interval for LOD by PROBIT analysis | | | 14.9-29.4 cp/mL |

Summary LOD
1. The PROBIT analysis at 95% hit rate resulted in an LOD of 41.8 cp/mL for 200 μL input volume and 18.9 cp/mL for 500 μL input volume.
2. The 95% confidence interval range for these concentrations was 30.9-74.9 cp/mL for 200 μL input volume and 14.9-29.4 cp/mL for 500 μL input volume.

Linearity

The samples used in the Linearity/Dynamic Range/Accuracy study consisted of a dilution panel of an HIV-1 cell culture supernatant material, HIV-1 group M subtype B.

The linearity panel was prepared by serial dilution. This panel was analyzed at 10 concentration levels.

The concentrations were selected as follows: One level below expected Lower Limit of Quantitation (LLoQ), one at LLoQ, one above LLoQ, several concentrations at intermediate levels, at expected Upper Limit of Quantitation (ULoQ) and one above ULoQ. For all concentrations 21 replicates were tested. The linearity study was done with 500 μL input volume):

PM 1—2.0E+07 cp/mL—above expected ULoQ
PM 2—1.0E+07 cp/mL—at expected ULoQ
PM 3—1.0E+06 cp/mL—below expected ULoQ
PM 4—1.0E+05 cp/mL—intermediate concentration level
PM 5 3.0E+04 cp/mL—intermediate concentration level for titer assignment
PM 6—1.0E+04 cp/mL—intermediate concentration level
PM 7—1.0E+03 cp/mL—intermediate concentration level
PM 8—1.0E+02 cp/mL—intermediate concentration level
PM 9—5.0E+01 cp/mL—above expected LLoQ
PM 10—2.0E+01 cp/mL—at expected LLoQ
PM 11—1.5E+01 cp/mL below expected LLoQ

TABLE 23

Linearity in EDTA Plasma

| Nominal Titer (cp/mL) | Assigned Titer (cp/mL) | Assigned Log10 Titer | Mean Log 10 Titer observed | Replicates |
|---|---|---|---|---|
| 1.50E+01 | 1.50E+01 | 1.2 | 1.3 | 21 |
| 2.00E+01 | 2.00E+01 | 1.3 | 1.5 | 21 |
| 5.00E+01 | 5.10E+01 | 1.7 | 1.8 | 21 |
| 1.00E+02 | 1.00E+02 | 2 | 2 | 21 |
| 1.00E+03 | 1.00E+03 | 3 | 3 | 21 |
| 1.00E+04 | 1.00E+04 | 4 | 4 | 21 |
| 1.00E+05 | 1.00E+05 | 5 | 5 | 21 |
| 1.00E+06 | 1.00E+06 | 6 | 6 | 21 |
| 1.00E+07 | 1.00E+07 | 7 | 7 | 21 |
| 2.00E+07 | 2.00E+07 | 7.3 | 7.4 | 21 |

A graphical depiction of this result is shown in FIG. 17.

Summary Linearity

The linear range, defined as the concentration range for which the log 10 deviation of the mean log 10 observed titers is within ±0.3 of the log 10 nominal titer was determined as 1.5E+01 cp/mL-2.0E+07 cp/mL It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for controlled amplification of at least a first and a second target nucleic acid from a plurality of biological samples, comprising:

a) adding an internal control nucleic acid to each of the plurality of biological samples in a number of reaction vessels corresponding to the number of biological samples, wherein the internal control nucleic acid is identical for each of the plurality of biological samples, and wherein the sequence of the internal control nucleic acid is different from the sequences of the target nucleic acids;
b) purifying target nucleic acids from the plurality of biological samples and the internal control nucleic acid simultaneously in the reaction vessels;
c) adding amplification reagents to the reaction vessels, wherein the amplification reagents for the first target nucleic acid comprise at least one set of primers specific for the first target nucleic acid and at least one set of primers specific for the internal control nucleic acid, and the amplification reagents for the second target nucleic acid comprise at least one set of primers specific for the second target nucleic acid and at least one set of primers specific for the internal control nucleic acid, wherein the primers specific for the internal control nucleic acid are different from the primers specific for the first and second target nucleic acids, and wherein the amplification reagents further comprise a polymerase with reverse transcriptase activity;
d) incubating in the reaction vessels the target nucleic acids and the amplification reagents for a period of time and under conditions suitable for transcription of RNA by said polymerase with reverse transcriptase activity to occur, wherein the incubation of the polymerase with reverse transcriptase activity comprises the following steps in sequence: a first temperature of 55° C., followed by a second temperature of 60° C., followed by a third temperature of 65° C.;
e) incubating the reaction vessels simultaneously under identical conditions sufficient for amplification to occur; and
f) detecting and measuring signals generated by the amplification; wherein the signals generated by the amplification of the internal control nucleic acid are indicative of an amplification occurring in the reaction vessels even in the absence of signals generated by the amplification of the at least first and second target nucleic acids.

2. The method of claim 1, further comprising: g) determining the quantity of the at least first and second target nucleic acid.

3. The method of claim 1, wherein the internal control nucleic acid is DNA.

4. The method of claim 1, wherein the internal control nucleic acid is RNA.

5. The method of claim 1, wherein the internal control nucleic acid is an armored nucleic acid.

6. The method of claim 1, wherein the sequence of the internal control nucleic acid is derived from a plant genome.

7. The method of claim 1, wherein the sequence of the internal control nucleic acid is scrambled.

8. The method of claim 1, wherein the internal control nucleic acid is selected from the group consisting of SEQ ID NOS: 45-48.

9. The method of claim 1, wherein the amplification reagents for the first target nucleic acid further comprise at least one probe specific for the first target nucleic acid and at least one probe specific for the internal control nucleic acid, and the amplification reagents for the second target nucleic acid further comprise at least one probe specific for the second target nucleic acid and at least one probe specific for the internal control nucleic acid, and wherein the probe specific for the internal control nucleic acid is different from the probes specific for the first and second target nucleic acids.

10. The method of claim 1, wherein a single reaction vessel comprises amplification reagents for the first and the second target nucleic acids.

11. The method of claim 8, wherein the internal control nucleic acid comprises SEQ ID NO: 45.

12. The method of claim 8, wherein the internal control nucleic acid comprises SEQ ID NO: 46.

13. The method of claim 8, wherein the internal control nucleic acid comprises SEQ ID NO: 47.

14. The method of claim 8, wherein the internal control nucleic acid comprises SEQ ID NO: 48.

* * * * *

SEQUENCE LISTING

<160> NUMBER OF SEQ ID NOS: 76

<210> SEQ ID NO 1
<211> LENGTH: 29
<212> TYPE: DNA
<213> ORGANISM: Artificial Sequence
<220> FEATURE:
<223> OTHER INFORMATION: primer/probe

<400> SEQUENCE: 1
agtgggggga catcaagcag ccatgcaaa                                     29

<210> SEQ ID NO 2
<211> LENGTH: 30
<212> TYPE: DNA
<213> ORGANISM: Artificial Sequence

```
<220> FEATURE:
<223> OTHER INFORMATION: primer/probe

<400> SEQUENCE: 2
agtgggggga catcaagcag ccatgcaaat                                        30

<210> SEQ ID NO 3
<211> LENGTH: 23
<212> TYPE: DNA
<213> ORGANISM: Artificial Sequence
<220> FEATURE:
<223> OTHER INFORMATION: primer/probe

<400> SEQUENCE: 3
gctttcagcc cagaagtaat acc                                               23

<210> SEQ ID NO 4
<211> LENGTH: 25
<212> TYPE: DNA
<213> ORGANISM: Artificial Sequence
<220> FEATURE:
<223> OTHER INFORMATION: primer/probe

<400> SEQUENCE: 4
ggacacatca agcagccatg caaat                                             25

<210> SEQ ID NO 5
<211> LENGTH: 20
<212> TYPE: DNA
<213> ORGANISM: Artificial Sequence
<220> FEATURE:
<223> OTHER INFORMATION: primer/probe

<400> SEQUENCE: 5
agagaaccaa ggggaagtga                                                   20

<210> SEQ ID NO 6
<211> LENGTH: 28
<212> TYPE: DNA
<213> ORGANISM: Artificial Sequence
<220> FEATURE:
<223> OTHER INFORMATION: primer/probe

<400> SEQUENCE: 6
ataatccacc tatcccagta ggagaaat                                          28

<210> SEQ ID NO 7
<211> LENGTH: 29
<212> TYPE: DNA
<213> ORGANISM: Artificial Sequence
<220> FEATURE:
<223> OTHER INFORMATION: primer/probe

<400> SEQUENCE: 7
agtgggggga caccaggcag caatgcaaa                                         29

<210> SEQ ID NO 8
<211> LENGTH: 20
<212> TYPE: DNA
<213> ORGANISM: Artificial Sequence
<220> FEATURE:
<223> OTHER INFORMATION: primer/probe

<400> SEQUENCE: 8
catagcagga actactagta                                                   20
```

<210> SEQ ID NO 9
<211> LENGTH: 30
<212> TYPE: DNA
<213> ORGANISM: Artificial Sequence
<220> FEATURE:
<223> OTHER INFORMATION: primer/probe

<400> SEQUENCE: 9
ggtactagta gttcctgcta tgtcacttcc                                    30

<210> SEQ ID NO 10
<211> LENGTH: 25
<212> TYPE: DNA
<213> ORGANISM: Artificial Sequence
<220> FEATURE:
<223> OTHER INFORMATION: primer/probe

<400> SEQUENCE: 10
ctatgtcact tccccttggt tctct                                         25

<210> SEQ ID NO 11
<211> LENGTH: 30
<212> TYPE: DNA
<213> ORGANISM: Artificial Sequence
<220> FEATURE:
<223> OTHER INFORMATION: primer/probe

<400> SEQUENCE: 11
ggtactagta gttcctgcta tatcacttcc                                    30

<210> SEQ ID NO 12
<211> LENGTH: 20
<212> TYPE: DNA
<213> ORGANISM: Artificial Sequence
<220> FEATURE:
<223> OTHER INFORMATION: primer/probe

<400> SEQUENCE: 12
tccttgtctt atgtccagaa                                               20

<210> SEQ ID NO 13
<211> LENGTH: 28
<212> TYPE: DNA
<213> ORGANISM: Artificial Sequence
<220> FEATURE:
<223> OTHER INFORMATION: primer/probe

<400> SEQUENCE: 13
tttggtcctt gtcttatgtc cagaatgc                                      28

<210> SEQ ID NO 14
<211> LENGTH: 28
<212> TYPE: DNA
<213> ORGANISM: Artificial Sequence
<220> FEATURE:
<223> OTHER INFORMATION: primer/probe

<400> SEQUENCE: 14
tactagtagt tcctgctatg tcacttcc                                      28

<210> SEQ ID NO 15
<211> LENGTH: 23
<212> TYPE: DNA
<213> ORGANISM: Artificial Sequence
<220> FEATURE:
<223> OTHER INFORMATION: primer/probe

```
<400> SEQUENCE: 15
tgtgttatga tggtgtttaa atc                                          23

<210> SEQ ID NO 16
<211> LENGTH: 20
<212> TYPE: DNA
<213> ORGANISM: Artificial Sequence
<220> FEATURE:
<223> OTHER INFORMATION: primer/probe

<400> SEQUENCE: 16
actctaaagg gttcctttgg                                              20

<210> SEQ ID NO 17
<211> LENGTH: 33
<212> TYPE: DNA
<213> ORGANISM: Artificial Sequence
<220> FEATURE:
<223> OTHER INFORMATION: primer/probe

<400> SEQUENCE: 17
tctgcagctt cctcattgat ggtatctttt aac                               33

<210> SEQ ID NO 18
<211> LENGTH: 29
<212> TYPE: DNA
<213> ORGANISM: Artificial Sequence
<220> FEATURE:
<223> OTHER INFORMATION: primer/probe

<400> SEQUENCE: 18
tcagcattat cagaaggagc caccccaca                                    29

<210> SEQ ID NO 19
<211> LENGTH: 32
<212> TYPE: DNA
<213> ORGANISM: Artificial Sequence
<220> FEATURE:
<223> OTHER INFORMATION: primer/probe

<400> SEQUENCE: 19
tctgcagctt cctcattgag gtatcttta ac                                 32

<210> SEQ ID NO 20
<211> LENGTH: 41
<212> TYPE: DNA
<213> ORGANISM: Artificial Sequence
<220> FEATURE:
<223> OTHER INFORMATION: primer/probe

<400> SEQUENCE: 20
atcctgggat taaataaaat agtaagaatg tatagcccta c                      41

<210> SEQ ID NO 21
<211> LENGTH: 29
<212> TYPE: DNA
<213> ORGANISM: Artificial Sequence
<220> FEATURE:
<223> OTHER INFORMATION: primer/probe

<400> SEQUENCE: 21
accatcaatg agggaagctg cagaatggg                                    29

<210> SEQ ID NO 22
```

```
<211> LENGTH: 26
<212> TYPE: DNA
<213> ORGANISM: Artificial Sequence
<220> FEATURE:
<223> OTHER INFORMATION: primer/probe

<400> SEQUENCE: 22
tgactctggt aactagagat ccctca                                            26

<210> SEQ ID NO 23
<211> LENGTH: 30
<212> TYPE: DNA
<213> ORGANISM: Artificial Sequence
<220> FEATURE:
<223> OTHER INFORMATION: primer/probe

<400> SEQUENCE: 23
tgttcaaccc tggtatctag agatccctca                                        30

<210> SEQ ID NO 24
<211> LENGTH: 20
<212> TYPE: DNA
<213> ORGANISM: Artificial Sequence
<220> FEATURE:
<223> OTHER INFORMATION: primer/probe

<400> SEQUENCE: 24
ggctaactag ggacccactg                                                   20

<210> SEQ ID NO 25
<211> LENGTH: 18
<212> TYPE: DNA
<213> ORGANISM: Artificial Sequence
<220> FEATURE:
<223> OTHER INFORMATION: primer/probe

<400> SEQUENCE: 25
actagggaac ccactgct                                                     18

<210> SEQ ID NO 26
<211> LENGTH: 26
<212> TYPE: DNA
<213> ORGANISM: Artificial Sequence
<220> FEATURE:
<223> OTHER INFORMATION: primer/probe

<400> SEQUENCE: 26
tcagcaagcc gagtcctgcg tcgaga                                            26

<210> SEQ ID NO 27
<211> LENGTH: 27
<212> TYPE: DNA
<213> ORGANISM: Artificial Sequence
<220> FEATURE:
<223> OTHER INFORMATION: primer/probe

<400> SEQUENCE: 27
ccgctaagcc gagccctttg cgtcgga                                           27

<210> SEQ ID NO 28
<211> LENGTH: 17
<212> TYPE: DNA
<213> ORGANISM: Artificial Sequence
<220> FEATURE:
<223> OTHER INFORMATION: primer/probe

<400> SEQUENCE: 28
```
ggtctgaggg atctcta                                                    17

<210> SEQ ID NO 29
<211> LENGTH: 24
<212> TYPE: DNA
<213> ORGANISM: Artificial Sequence
<220> FEATURE:
<223> OTHER INFORMATION: primer/probe

<400> SEQUENCE: 29
ctgctagaga ttttccacac tgac                                            24

<210> SEQ ID NO 30
<211> LENGTH: 23
<212> TYPE: DNA
<213> ORGANISM: Artificial Sequence
<220> FEATURE:
<223> OTHER INFORMATION: primer/probe

<400> SEQUENCE: 30
ggctccacgc ttgcttgctt aaa                                             23

<210> SEQ ID NO 31
<211> LENGTH: 18
<212> TYPE: DNA
<213> ORGANISM: Artificial Sequence
<220> FEATURE:
<223> OTHER INFORMATION: primer/probe

<400> SEQUENCE: 31
ggctccacgc ttgcttgc                                                   18

<210> SEQ ID NO 32
<211> LENGTH: 31
<212> TYPE: DNA
<213> ORGANISM: Artificial Sequence
<220> FEATURE:
<223> OTHER INFORMATION: primer/probe

<400> SEQUENCE: 32
ttcccaaagc aagaagggtc ctaacagacc a                                    31

<210> SEQ ID NO 33
<211> LENGTH: 28
<212> TYPE: DNA
<213> ORGANISM: Artificial Sequence
<220> FEATURE:
<223> OTHER INFORMATION: primer/probe

<400> SEQUENCE: 33
tctctagcag tggcgcccga acagggac                                        28

<210> SEQ ID NO 34
<211> LENGTH: 34
<212> TYPE: DNA
<213> ORGANISM: Artificial Sequence
<220> FEATURE:
<223> OTHER INFORMATION: primer/probe

<400> SEQUENCE: 34
accagagtca cacaacagac gggcacacac tact                                 34

<210> SEQ ID NO 35
<211> LENGTH: 31
<212> TYPE: DNA

```
<213> ORGANISM: Artificial Sequence
<220> FEATURE:
<223> OTHER INFORMATION: primer/probe

<400> SEQUENCE: 35
tcctagtcgc cgcctggtca ttcggtgttc a                                31

<210> SEQ ID NO 36
<211> LENGTH: 25
<212> TYPE: DNA
<213> ORGANISM: Artificial Sequence
<220> FEATURE:
<223> OTHER INFORMATION: primer/probe

<400> SEQUENCE: 36
catgcaactt tttcacctct gccta                                       25

<210> SEQ ID NO 37
<211> LENGTH: 27
<212> TYPE: DNA
<213> ORGANISM: Artificial Sequence
<220> FEATURE:
<223> OTHER INFORMATION: primer/probe

<400> SEQUENCE: 37
aactccacag tagctccaaa ttcttta                                     27

<210> SEQ ID NO 38
<211> LENGTH: 33
<212> TYPE: DNA
<213> ORGANISM: Artificial Sequence
<220> FEATURE:
<223> OTHER INFORMATION: primer/probe

<400> SEQUENCE: 38
ccaagctgtg ccttgggtgg ctttggggca tgg                              33

<210> SEQ ID NO 39
<211> LENGTH: 23
<212> TYPE: DNA
<213> ORGANISM: Artificial Sequence
<220> FEATURE:
<223> OTHER INFORMATION: primer/probe

<400> SEQUENCE: 39
gggattcctg taacaacaag tca                                         23

<210> SEQ ID NO 40
<211> LENGTH: 24
<212> TYPE: DNA
<213> ORGANISM: Artificial Sequence
<220> FEATURE:
<223> OTHER INFORMATION: primer/probe

<400> SEQUENCE: 40
tcttccccag aacaataaga acac                                        24

<210> SEQ ID NO 41
<211> LENGTH: 26
<212> TYPE: DNA
<213> ORGANISM: Artificial Sequence
<220> FEATURE:
<223> OTHER INFORMATION: primer/probe

<400> SEQUENCE: 41
ggcttgcaga gttctatagt gctatg                                      26
```

<210> SEQ ID NO 42
<211> LENGTH: 25
<212> TYPE: DNA
<213> ORGANISM: Artificial Sequence
<220> FEATURE:
<223> OTHER INFORMATION: primer/probe

<400> SEQUENCE: 42
ttgatagcaa tcggctatcg actaa                                           25

<210> SEQ ID NO 43
<211> LENGTH: 28
<212> TYPE: DNA
<213> ORGANISM: Artificial Sequence
<220> FEATURE:
<223> OTHER INFORMATION: primer/probe

<400> SEQUENCE: 43
gcttcgatac tcagtcatct cggtataa                                        28

<210> SEQ ID NO 44
<211> LENGTH: 27
<212> TYPE: DNA
<213> ORGANISM: Artificial Sequence
<220> FEATURE:
<223> OTHER INFORMATION: primer/probe

<400> SEQUENCE: 44
tctctcgcca tctcctaccg cattggc                                         27

<210> SEQ ID NO 45
<211> LENGTH: 269
<212> TYPE: DNA
<213> ORGANISM: Artificial Sequence
<220> FEATURE:
<223> OTHER INFORMATION: internal control nucleic acid

<400> SEQUENCE: 45
aattcaagct tagatctagc tttgcctgct tgatagcaat cggctatcga ctaatgactg     60
tcctggcggt ctctcgccat ctcctaccgc attggctcat aggtaagctc gctgtcaccc    120
agtacggagg tgccagtaga ttattagaga cagtcgccaa tcgatcgtta taccgagatg    180
actgagtatc gaagctacat tgtagccgca cataggacca cccatcttca tgttgaaaca    240
tgaggattac ccatgtggat ccaagcttg                                      269

<210> SEQ ID NO 46
<211> LENGTH: 235
<212> TYPE: DNA
<213> ORGANISM: Artificial Sequence
<220> FEATURE:
<223> OTHER INFORMATION: internal control nucleic acid

<400> SEQUENCE: 46
gggctgcagg tcgactctag attctaagaa tttgatgggc ttttctact aattactatt      60 agtatattgc catctttaac acttagaccg aagtgtgctg aagttccagt ggccggccca    120
gacctgggaa gttgcaagga cttaaacgaa tgcaagcgat catatcttga aaattataa    180 ccagaggatc gatgaaaaaa atttcttaga gctttggatc cccgggcgag ctccc         235

<210> SEQ ID NO 47
<211> LENGTH: 350
<212> TYPE: DNA

```
<213> ORGANISM: Artificial Sequence
<220> FEATURE:
<223> OTHER INFORMATION: internal control nucleic acid

<400> SEQUENCE: 47
cgactctaga tgaagggagc cttagaacgg ggctgcgcta gctggcatca aagtccgtca      60
gagctcaacc ctccaacgag gattcctgaa tactcgaaag tcagtgtgca gttactaaca     120
acagctgctc gacctcgggg tctcgaacaa tccatacctg ctatcgctgc cttcagacat     180
acggatgggc taggaggcaa gagctacctg tctcaacgaa ctatcggagt gggacccgat     240
gaagctgtca gcgccacttc cggcggtaag gctttaaaac gcgccgccg gttatcacgc      300 gcggggagca cagcgcggac tgacgtgctg ggaagcaccg gttaaggatc                350

<210> SEQ ID NO 48
<211> LENGTH: 470
<212> TYPE: DNA
<213> ORGANISM: Artificial Sequence
<220> FEATURE:
<223> OTHER INFORMATION: internal control nucleic acid

<400> SEQUENCE: 48
cgactctaga aactgggtag taactgcggg ggcgaatgat gcaggcttca gaaattaaac      60
tcaatagtat ccggtgtctc aatctttttc gggccaggcg gcggtggacg acagacaatt    120
ttacgatttt ggttccggtc acaaccgcgc catacatgtc aagaatgaag tgggcgaacg     180
ctagaaaact gacgccagca attaagtgag tcggggcgtg gtgactccca cgtaaaaagc    240
ccctaccccg caccgttacg aagtatcaaa acgggacgcg cacgaaccga cgattggtac    300
tgtataagcg gcccgacgaa ctcaaaatcc caagtgaatc tatgaaatct acatcgcgtt    360
tataatctac ggggtgtaaa cggatgagaa ttggccaaac ggaggcacac acgcgtgcaa    420
tgcgccgacc ctgagaaaag tatcatgtgc gtcggccaca ggatccccgg                470

<210> SEQ ID NO 49
<211> LENGTH: 350
<212> TYPE: DNA
<213> ORGANISM: Artificial Sequence
<220> FEATURE:
<223> OTHER INFORMATION: internal control nucleic acid

<400> SEQUENCE: 49
cgactctaga tgaagggagc cttagaacgg ggctgcgcta gctggcatca aagtccgtca      60
gagctcaacc ctccaacgag gattcctgaa tactcgaaag tcagtgtgca gttactaaca     120
acagctgctc gacctcgggg tctcgaacaa tccatacctg ctatcgctgc cttcagacat     180
acggatgggc taggaggcaa gagctacctg tctcaacgaa ctatcggagt gggacccgat     240
gaagctgtca gcgccacttc cggcggtaag gctttaaaac gcgccgccg gttatcacgc      300 gcggggagca cagcgcggac tgacgtgctg ggaagcaccg gttaaggatc                350

<210> SEQ ID NO 50
<211> LENGTH: 25
<212> TYPE: DNA
<213> ORGANISM: Artificial Sequence
<220> FEATURE:
<223> OTHER INFORMATION: primer/probe

<400> SEQUENCE: 50
acaaccgcgc catacatgtc aagaa                                            25
```

```
<210> SEQ ID NO 51
<211> LENGTH: 24
<212> TYPE: DNA
<213> ORGANISM: Artificial Sequence
<220> FEATURE:
<223> OTHER INFORMATION: primer/probe

<400> SEQUENCE: 51
gtcgggccgc ttatacagta ccaa                                            24

<210> SEQ ID NO 52
<211> LENGTH: 32
<212> TYPE: DNA
<213> ORGANISM: Artificial Sequence
<220> FEATURE:
<223> OTHER INFORMATION: primer/probe

<400> SEQUENCE: 52
gccagcaatt aagtgagtcg gggcgtggtg ac                                   32

<210> SEQ ID NO 53
<211> LENGTH: 52
<212> TYPE: DNA
<213> ORGANISM: Artificial Sequence
<220> FEATURE:
<223> OTHER INFORMATION: primer/probe

<400> SEQUENCE: 53
caacaaaaca gcatattgac acctgggagt agactaggag atcttctgct ct             52

<210> SEQ ID NO 54
<211> LENGTH: 30
<212> TYPE: DNA
<213> ORGANISM: Artificial Sequence
<220> FEATURE:
<223> OTHER INFORMATION: primer/probe

<400> SEQUENCE: 54
tctcctagtc tttcccaggt gtcaatatgc                                      30

<210> SEQ ID NO 55
<211> LENGTH: 27
<212> TYPE: DNA
<213> ORGANISM: Artificial Sequence
<220> FEATURE:
<223> OTHER INFORMATION: primer/probe

<400> SEQUENCE: 55
ctgccccagg aggactgggt aacaaa                                          27

<210> SEQ ID NO 56
<211> LENGTH: 23
<212> TYPE: DNA
<213> ORGANISM: Artificial Sequence
<220> FEATURE:
<223> OTHER INFORMATION: primer/probe

<400> SEQUENCE: 56
tcctagtcta tcccaggtgt caa                                             23

<210> SEQ ID NO 57
<211> LENGTH: 25
<212> TYPE: DNA
<213> ORGANISM: Artificial Sequence
<220> FEATURE:
<223> OTHER INFORMATION: primer/probe
```

```
<400> SEQUENCE: 57
gtaagccctc agaaccgtct cggaa                                          25

<210> SEQ ID NO 58
<211> LENGTH: 28
<212> TYPE: DNA
<213> ORGANISM: Artificial Sequence
<220> FEATURE:
<223> OTHER INFORMATION: primer/probe

<400> SEQUENCE: 58
ggactagagg ttagaggaga ccccgagg                                       28

<210> SEQ ID NO 59
<211> LENGTH: 28
<212> TYPE: DNA
<213> ORGANISM: Artificial Sequence
<220> FEATURE:
<223> OTHER INFORMATION: primer/probe

<400> SEQUENCE: 59
aaggactaga ggttagagga gaccccgc                                       28

<210> SEQ ID NO 60
<211> LENGTH: 21
<212> TYPE: DNA
<213> ORGANISM: Artificial Sequence
<220> FEATURE:
<223> OTHER INFORMATION: primer/probe

<400> SEQUENCE: 60
aaacccactc tatgtccggt c                                              21

<210> SEQ ID NO 61
<211> LENGTH: 21
<212> TYPE: DNA
<213> ORGANISM: Artificial Sequence
<220> FEATURE:
<223> OTHER INFORMATION: primer/probe

<400> SEQUENCE: 61
gtacgccgga attgccggaa a                                              21

<210> SEQ ID NO 62
<211> LENGTH: 21
<212> TYPE: DNA
<213> ORGANISM: Artificial Sequence
<220> FEATURE:
<223> OTHER INFORMATION: primer/probe

<400> SEQUENCE: 62
cctcaaagaa aaaccaaaag a                                              21

<210> SEQ ID NO 63
<211> LENGTH: 26
<212> TYPE: DNA
<213> ORGANISM: Artificial Sequence
<220> FEATURE:
<223> OTHER INFORMATION: primer/probe

<400> SEQUENCE: 63
gcagaaagcg tctagccatg gcgtta                                         26

<210> SEQ ID NO 64
<211> LENGTH: 24
```

```
<212> TYPE: DNA
<213> ORGANISM: Artificial Sequence
<220> FEATURE:
<223> OTHER INFORMATION: primer/probe

<400> SEQUENCE: 64
gcagaaagcg tctagccatg gcgt                                         24

<210> SEQ ID NO 65
<211> LENGTH: 21
<212> TYPE: DNA
<213> ORGANISM: Artificial Sequence
<220> FEATURE:
<223> OTHER INFORMATION: primer/probe

<400> SEQUENCE: 65
tggcgtctcc cacgcggctg g                                            21

<210> SEQ ID NO 66
<211> LENGTH: 21
<212> TYPE: DNA
<213> ORGANISM: Artificial Sequence
<220> FEATURE:
<223> OTHER INFORMATION: primer/probe

<400> SEQUENCE: 66
ctttccccag gacctgccgg t                                            21

<210> SEQ ID NO 67
<211> LENGTH: 25
<212> TYPE: DNA
<213> ORGANISM: Artificial Sequence
<220> FEATURE:
<223> OTHER INFORMATION: primer/probe

<400> SEQUENCE: 67
gcaagcaccc tataggcagt accac                                        25

<210> SEQ ID NO 68
<211> LENGTH: 24
<212> TYPE: DNA
<213> ORGANISM: Artificial Sequence
<220> FEATURE:
<223> OTHER INFORMATION: primer/probe

<400> SEQUENCE: 68
ctcgcaagca ccctatcagg cagt                                         24

<210> SEQ ID NO 69
<211> LENGTH: 28
<212> TYPE: DNA
<213> ORGANISM: Artificial Sequence
<220> FEATURE:
<223> OTHER INFORMATION: primer/probe

<400> SEQUENCE: 69
gcaagcaccc tatcaggcag taccacaa                                     28

<210> SEQ ID NO 70
<211> LENGTH: 27
<212> TYPE: DNA
<213> ORGANISM: Artificial Sequence
<220> FEATURE:
<223> OTHER INFORMATION: primer/probe

<400> SEQUENCE: 70
```

```
gcaagcaccc tatcaggcag taccaca                                          27

<210> SEQ ID NO 71
<211> LENGTH: 24
<212> TYPE: DNA
<213> ORGANISM: Artificial Sequence
<220> FEATURE:
<223> OTHER INFORMATION: primer/probe

<400> SEQUENCE: 71
ttgccggaaa gactgggtcc tttc                                             24

<210> SEQ ID NO 72
<211> LENGTH: 24
<212> TYPE: DNA
<213> ORGANISM: Artificial Sequence
<220> FEATURE:
<223> OTHER INFORMATION: primer/probe

<400> SEQUENCE: 72
ttgccggaaa gactgggtcc tttc                                             24

<210> SEQ ID NO 73
<211> LENGTH: 24
<212> TYPE: DNA
<213> ORGANISM: Artificial Sequence
<220> FEATURE:
<223> OTHER INFORMATION: primer/probe

<400> SEQUENCE: 73
ccagcccatc ccgaaagatc ggcg                                             24

<210> SEQ ID NO 74
<211> LENGTH: 18
<212> TYPE: DNA
<213> ORGANISM: Artificial Sequence
<220> FEATURE:
<223> OTHER INFORMATION: primer/probe

<400> SEQUENCE: 74
tgtccggtca tttgggcg                                                    18

<210> SEQ ID NO 75
<211> LENGTH: 33
<212> TYPE: DNA
<213> ORGANISM: Artificial Sequence
<220> FEATURE:
<223> OTHER INFORMATION: primer/probe

<400> SEQUENCE: 75
ccgggagagc catagtggtc tgcggaaccg gtg                                   33

<210> SEQ ID NO 76
<211> LENGTH: 28
<212> TYPE: DNA
<213> ORGANISM: Artificial Sequence
<220> FEATURE:
<223> OTHER INFORMATION: primer/probe

<400> SEQUENCE: 76
tctctcgccc atctcctacc gcattggc                                         28
```